US009164026B2

(12) United States Patent
Chakravarty et al.

(10) Patent No.: US 9,164,026 B2
(45) Date of Patent: Oct. 20, 2015

(54) PACKAGED CHIP FOR MULTIPLEXING PHOTONIC CRYSTAL MICROCAVITY COUPLED WAVEGUIDE AND PHOTONIC CRYSTAL SLOT WAVEGUIDE DEVICES FOR CHIP-INTEGRATED LABEL-FREE DETECTION AND ABSORPTION SPECTROSCOPY WITH HIGH THROUGHPUT, SENSITIVITY, SPECIFICITY, AND WIDE DYNAMIC RANGE

(71) Applicants: Swapnajit Chakravarty, Austin, TX (US); Amir Hosseini, Austin, TX (US); Ray T. Chen, Austin, TX (US)

(72) Inventors: Swapnajit Chakravarty, Austin, TX (US); Amir Hosseini, Austin, TX (US); Ray T. Chen, Austin, TX (US)

(73) Assignee: Omega Optics, Inc., Austin, TX (US)

( * ) Notice: Subject to any disclaimer, the term of this patent is extended or adjusted under 35 U.S.C. 154(b) by 77 days.

(21) Appl. No.: 14/165,554

(22) Filed: Jan. 27, 2014

(65) Prior Publication Data

US 2014/0140655 A1     May 22, 2014

Related U.S. Application Data

(63) Continuation-in-part of application No. 13/607,801, filed on Sep. 9, 2012, now Pat. No. 8,636,955, which is a continuation-in-part of application No. 12/462,311, filed on Aug. 3, 2009, now Pat. No. 8,293,177, and a continuation-in-part of application No. 12/806,840, filed on Aug. 23, 2010, now Pat. No. 8,282,882.

(51) Int. Cl.
| | |
|---|---|
| *G01N 21/00* | (2006.01) |
| *G01N 21/25* | (2006.01) |
| *G01N 21/77* | (2006.01) |
| *G01N 33/543* | (2006.01) |
| *G02B 6/122* | (2006.01) |
| *B82Y 20/00* | (2011.01) |
| *G02B 6/30* | (2006.01) |
| *G02B 6/34* | (2006.01) |
| *G02B 6/124* | (2006.01) |
| *G02B 6/28* | (2006.01) |
| *G02B 6/12* | (2006.01) |

(52) U.S. Cl.
CPC .............. *G01N 21/253* (2013.01); *B82Y 20/00* (2013.01); *G01N 21/7746* (2013.01); *G01N 33/54373* (2013.01); *G02B 6/1225* (2013.01); *G01N 2021/7789* (2013.01); *G02B 6/124* (2013.01); *G02B 6/2813* (2013.01); *G02B 6/30* (2013.01); *G02B 6/34* (2013.01); *G02B 2006/12154* (2013.01)

(58) Field of Classification Search
CPC ....................... G01N 21/7743; G01N 21/7746
USPC ................................. 422/82.11, 82.05, 82.09
See application file for complete search history.

*Primary Examiner* — Natalia Levkovich
(74) *Attorney, Agent, or Firm* — Taboada Law Firm, PLLC; John M. Taboada

(57) ABSTRACT

Systems and methods for chip-integrated label-free detection and absorption spectroscopy with high throughput, sensitivity, and specificity are disclosed. The invention comprises packaged chips for multiplexing photonic crystal microcavity waveguide and photonic crystal slot waveguide devices. The packaged chips comprise crossing waveguides to prevent leakage of fluids from the microfluidic channels from the trenches or voids around the light guiding waveguides. Other embodiments are described and claimed.

45 Claims, 61 Drawing Sheets

Along F-F'

Along G-G'

PACKAGED CHIP FOR MULTIPLEXING PHOTONIC CRYSTAL MICROCAVITY COUPLED WAVEGUIDE AND PHOTONIC CRYSTAL SLOT WAVEGUIDE DEVICES FOR CHIP-INTEGRATED LABEL-FREE DETECTION AND ABSORPTION SPECTROSCOPY WITH HIGH THROUGHPUT, SENSITIVITY, SPECIFICITY, AND WIDE DYNAMIC RANGE

I. CROSS REFERENCE TO RELATED APPLICATIONS

The application is a continuation-in-part application of U.S. patent application Ser. No. 13/607,801, titled "Packaged Chip for Multiplexing Photonic Crystal Waveguide and Photonic Crystal Slot Waveguide Devices for Chip-Integrated Label-Free Detection and Absorption Spectroscopy with High Throughput, Sensitivity, and Specificity", filed Sep. 9, 2012, which is a continuation-in-part application of U.S. patent application Ser. No. 12/462,311, titled "Photonic Crystal Microarray Device for Label-Free Multiple Analyte Sensing, Biosensing and Diagnostic Assay Chips", filed Aug. 3, 2009, now U.S. Pat. No. 8,293,177 and a continuation-in-part application of U.S. patent application Ser. No. 12/806,840, titled "Photonic Crystal Slot Waveguide Miniature On-Chip Absorption Spectrometer", filed Aug. 23, 2010, now U.S. Pat. No. 8,282,882, the contents of which are all hereby incorporated by reference.

II. BACKGROUND

1. Field of the Invention

This invention relates generally to the field of packaged chip integrated optical devices, for chip-integrated infrared optical absorption spectroscopy as well as chip-integrated label-free biomolecule microarray. The apparatus and method enables high throughput sensing as well as high specificity.

2. Background of the Invention

Label-free biosensors are particularly attractive since they avoid complex chemistries caused by steric hindrance of the labels. All methods of detection in lab-on-chip platforms at present transduce the specific binding of the biomolecule of interest to its specific conjugate biomolecule receptor bound to the device substrate, into an electrical, mechanical, or optical signal. Optical detection techniques are generally preferred due to their freedom from electromagnetic interference. While several platforms based on ring resonators, wire waveguides, and surface plasmon resonance (SPR) have been investigated, photonic crystal (PC) microcavities, in general, are more compact (of the order of a few square microns in surface area) and have higher sensitivity than other devices due to slow light effect and the larger optical mode overlap with the analyte within compact optical mode volume. Much of the research in the literature concerns single PC microcavity biosensors. Methods to array two-dimensional PC microcavities have primarily focused on the detection of a single bio-molecular probe binding to its specific conjugate target biomolecule on all microcavities. A method to array photonic crystal microcavities along a single photonic crystal waveguide was previously presented in U.S. Pat. No. 8,293, 177. Here, we disclose novel methods to array these PC microcavities using multimode interference optical power splitters which can be combined to create large chip-integrated microarrays in which all PC microcavity sensors, each coated with a different biomolecule target receptor, can be simultaneously interrogated with the same small quantity of probe sample, resulting in high throughout diagnostic assays. The multiplexed detection not only achieves high throughput detection, but the ability to measure many biomolecule interactions at the same instant of time allows one to do the actual test experiments and the control experiments and further multiplex these experiments to achieve higher statistical confidence regarding the specificity of the binding reactions. Sandwich assays can also be performed on the same platform to confirm binding specificity.

In addition, chip integrated optical absorption spectrometers are attractive since they allow chemical and biological analytes to be distinguished on a chip with near-infrared optical absorption signatures. Photonic crystal slot waveguide have been demonstrated as viable agents to perform chip-integrated optical absorption spectroscopy. However, in a photonic crystal slot waveguide, the wavelength range over which light is slowed down as it propagates down the photonic crystal waveguide is small. To increase the wavelength bandwidth over which slow light phenomenon is achieved and thus enable a wide bandwidth, infrared optical absorption spectrometer on chip, it is necessary to multiplex several photonic crystal slot waveguides. A method that couples light into all the photonic crystal slot waveguides simultaneously and thus measures the analyte absorption spectrum across a broad wavelength range on-chip is desired.

III. SUMMARY

One embodiment of the invention provides a sensor comprising a semiconductor material slab with high dielectric constant, supported on the bottom by a bottom cladding with dielectric constant lower than the slab. In some embodiments, a thin film (approximately 5 to 30 nanometers thick) of low index dielectric such as silicon dioxide or silicon nitride is present on the high index semiconductor slab material. Together, the semiconductor material with high dielectric constant and the thin film of low index dielectric on the high dielectric constant semiconductor material would comprise the slab. The bottom cladding is supported by the semiconductor substrate. The core in the slab is defined by the path via which light propagates in the slab. A multimode interference power splitter (MMI) is defined which splits the power from a single input ridge or rib waveguide into multiple (n) output ridge or rib waveguides where n=1, 2 . . . N. The MMI structure is a rectangular mesa defined in the slab, each MMI having a single input ridge or rib waveguide and several n=1, 2 . . . N output ridge or rib waveguides. The ridge waveguide on each output arm of the MMI in the first stage can further input light into a cascaded MMI in the second stage and succeeding stages. The number of cascaded stages is m where m=1, 2 . . . M. On each output arm of the $m^{th}$ cascaded MMI, a photonic crystal pattern is defined as a triangular lattice of holes, with a lattice constant $\alpha$, etched into the slab. The photonic crystal waveguide is defined by filling a single row of air holes, from input ridge waveguide transition to output ridge waveguide transition with the semiconductor slab material. This is equivalent to stating that a row of air holes from the input ridge waveguide to the output ridge waveguide is missing. Alternatively, when holes are etched in a triangular lattice into the slab, a row of the triangular lattice from the input ridge waveguide transition to output ridge waveguide transition is not etched. A photonic crystal microcavity is similarly defined by filing a few holes with semiconductor slab material. This is equivalent to stating that a few holes are missing. Alternatively, when holes are etched in a triangular lattice into the slab, a few holes of the triangular lattice are not etched in order to form a photonic crystal microcavity. The effect of holes etched into the slab is to lower the effective refractive index or dielectric constant of the slab. Thus when holes are not etched in the slab, the effective refractive index in that region is higher than the effective refractive index in the surrounding region where holes are etched in the slab. An optical microcavity is thus formed in the region of missing holes. Since the criteria for forming an optical microcavity is to create a region where the effective refractive index or dielectric constant is higher than in the surrounding region, an optical microcavity can also be formed by etching holes in the slab with a diameter smaller than the diameter of the other holes in the surrounding lattice. The region with the smaller holes has a smaller effective refractive index or dielectric constant than the surrounding region with larger holes etched into the slab. On each output arm of the MMI that has a photonic crystal waveguide, one or more (p) where p=1, 2 . . . P, photonic crystal microcavities are patterned at a distance of y lattice periods from the photonic crystal waveguide, where y=1, 2, 3, 4, 5, 6, or 7. Several (q) photonic crystal waveguides, where q=1, 2, . . . Q, each with one or more (p) photonic crystal microcavities, can be connected in series. The center-to-center distance between individual photonic crystal microcavities is 50 microns. Light is coupled into the first stage MMI via a ridge waveguide. Light is out-coupled from the output ridge waveguides of the last cascaded stage MMI into photonic crystal waveguides which finally end in M×N output ridge waveguides. The total number of photonic crystal microcavity sensors simultaneously interrogated is thus M×N×P×Q. When a broadband light source is input into the MMI, it splits the light into its output arms in the same ratio among all arms as 1/N. The intensity of light in each output arm is thus determined by the number of output arms. After M cascaded stages, the normalized intensity of light input into a photonic crystal waveguide is $1/(M \times N)$. On each output arm which has a photonic crystal waveguide, wavelengths corresponding to the resonant wavelengths of the individual microcavities are coupled to the corresponding microcavities. As a result, minima are observed in the transmission spectrum corresponding to the dropped wavelength of each photonic crystal microcavity. Depending upon the wavelength range of interrogation, the period of the lattice, a, can vary from 50 nm to 1500 nm and the etch depth of the lattice structure, which is equal to the height of the semiconductor slab, can vary from 0.4 to 0.7 times the lattice periodicity above. The semiconductor slab material can be silicon (or any Group IV material), gallium arsenide (or any III-V semiconductor) or any semiconductor material with high refractive index. The substrate can be any Group IV material corresponding to the Group IV core material, or any substrate suitable to grow the III-V slab material. The bottom cladding can be silicon dioxide, silicon nitride or any material with dielectric constant lower than the dielectric constant of the slab. Thus, multiple photonic crystal microcavities are not only arrayed along the length of the same photonic crystal waveguide on each arm, but on each output arm of the MMI. Since light is slowed down as it propagates down the photonic crystal waveguide, there arises a group index mismatch between the light that propagates down the photonic crystal waveguide and the light fed into the photonic crystal waveguide from the input ridge waveguide. A similar group index mismatch exists at the interface between the output end of the photonic crystal waveguide and the output ridge waveguide. Due to the index mismatch, Fresnel reflections occur from the ridge waveguide-photonic crystal waveguide facet. It is therefore necessary to design a group index taper that minimizes reflection and thus couples the light efficiently from the input ridge waveguide into the photonic crystal waveguide as well as couples light out efficiently from the photonic crystal waveguide to the output ridge waveguide. The group index taper, or impedance tapers, at both the input and the output of the photonic crystal waveguide are formed by shifting away the first S rows of air holes where S=1, 2, 3 . . . 32 away from the photonic crystal waveguide, normal to the photonic crystal waveguide in the plane of the slab varying in linear steps from $\sqrt{3\alpha}$ to 1.08 times $\sqrt{3\alpha}$ over S steps where S=1, 2, 3 . . . 32, where $\alpha$ is the lattice constant of the photonic crystal lattice. On each of the M×N output arms of the last cascaded stage of the MMI, the lattice constant of the triangular lattice photonic crystal may be the same or different. When the lattice constant of the triangular lattice photonic crystal are different, the absolute resonance frequency of the photonic crystal microcavity in each arm are different. Hence the absolute wavelength of the resonance frequency that is measured at each output sub-wavelength grating coupler is different. Consequently, the ridge waveguides that precede each output sub-wavelength grating coupler can be combined either by cascaded Y-junctions or through cascaded multimode interference power combiners, and terminated in a single output sub-wavelength grating coupler, without any overlap between the absolute resonance wavelengths from each photonic crystal microcavity. As a result, all resonances of all the photonic crystal microcavities can be measured from a single output sub-wavelength grating coupler. The sub-wavelength grating couplers at both the input and the output have a periodicity $\beta$ in one direction in the plane of the slab and a periodicity $\gamma$ in the direction orthogonal to $\beta$ in the plane of the slab.

Above the microcavity, a thin film of target biomolecules are immobilized on the microcavity surface. Each microcavity surface is coated with an exclusive target receptor molecule or biomolecule to form the dielectric coating. Since the target biomolecules are dispensed by ink-jet printing, the thin film of target biomolecules also coats on the inner surfaces of the columnar members in the immediate vicinity of the photonic crystal microcavity. The one or more binding molecules are free of detection labels. The one or more target biomolecules may also be tagged with fluorescent, radioactive, or magnetic labels. In order to immobilize the target biomolecules, when the high dielectric constant material of the slab is silicon, a thin layer of silicon dioxide is left on the silicon slab at the time of fabrication. When the high dielectric constant material of the slab is not silicon, silicon dioxide may be deposited by plasma enhanced chemical vapor deposition, post photonic crystal fabrication. When the high dielectric constant material of the slab is silicon, the device can be cleaned with a standard Piranha solution (a mixture of sulfuric acid and hydrogen peroxide) which forms a thin film of silicon dioxide on the surface of silicon. The silicon dioxide surface is then functionalized by treating with 10% by volume 3-aminopropyl-triethoxy-silane (3-APTES) in toluene. It is then washed 3 times in toluene to ensure complete removal of unbound 3-APTES, 3 times in methanol to remove toluene, and finally 3 times in de-ionized water to remove methanol. The device is then incubated in 1% glutaraldehyde in phosphate buffered saline (PBS) for 5 minutes and washed 3 times in PBS and ink jet printed with target antibodies (Abs) in glycerol. The printed spots were left to incubate overnight. Subsequently, all target Abs not bound to the functionalized device layer were removed by washing 3 times in PBS. The washing steps are completed in a few seconds, which ensures that unbound target Abs do not have sufficient time to bind to undesired areas which would result in cross-talk.

The one or more specific binding substances are thus arranged in an array on the microcavities, along the photonic crystal waveguide. A single transmission spectrum from each output arm of the MMI therefore probes the binding events on multiple P microcavities on a single photonic crystal waveguide. In each output arm of the MMI, several photonic crystal waveguides Q can be cascaded in series with photonic crystal microcavities coupled to photonic crystal waveguides in each cascaded stage. The transmission spectrum from all the output arms of all M stages of the 1×N MMI thus gives the result of binding events from M× N×P×Q photonic crystal microcavities at any given instant of time. In this way, high throughput measurement is achieved without the need for re-alignment of optics after each measurement. A binding event on a specific microcavity changes the resonance frequency of the photonic crystal microcavity. Since the resonance frequency of the photonic crystal microcavity is dropped from the transmission of the photonic crystal waveguide, a change in the resonance of the photonic crystal microcavity changes the dropped frequency/wavelength from the photonic crystal waveguide transmission and thus shifts the corresponding transmission minimum and leads to a sensing event for the specific microcavity. The change in resonance frequency of each photonic crystal microcavity is exclusive to the binding events between the target biomolecule coating the specific photonic crystal microcavity and its conjugate probe biomolecule in the sample analyte that is introduced, and is independent of the resonance frequency characteristics of other photonic crystal microcavities on the same photonic crystal waveguide or on other photonic crystal waveguides in other parallel cascaded arms of the MMI. Analyzed probe biomolecules can be proteins, DNA, RNA, small molecules, or genes. The light is input into the chip through only one ridge waveguide at the input of the first MMI in the first stage of the cascade. Thus simultaneous mutually exclusive measurements from M×N×p×Q photonic crystal microcavities are obtained simultaneously leading to high throughput sensing measurements.

Signal amplification as well as specific detection is achieved at low concentrations by incorporating a sandwich immunoassay technique. The target receptor molecule that is bound to the microcavity surface is designated as a primary target receptor. A resonance wavelength shift occurs when a probe biomolecule attaches to the primary target receptor. A secondary target biomolecule which also binds specifically to the probe biomolecule, when introduced, now causes an additional secondary resonance wavelength shift. In this way, the secondary target verifies that the biomolecule that has bound to the primary target receptor is in fact the probe biomolecule. By monitoring the resonance wavelength shifts, the specificity of binding is confirmed. No resonance wavelength shift shall be observed upon introduction of either the probe biomolecule or the secondary target antibodies, on a second photonic crystal microcavity in the array which is coated with a control biomolecule such as bovine serum albumin (BSA). No resonance wavelength shift shall be observed upon introduction of either the probe biomolecule or the secondary target antibodies, on a third photonic crystal microcavity in the array which is coated with an isotype matched control biomolecule. The specificity of the assay is thus verified from the results on three photonic crystal microcavities. In addition to the secondary resonance wavelength shift caused by the binding of the secondary target to the probe biomolecule, the lack of any resonance wavelength shift in the control photonic crystal microcavities confirms the specificity. In one preferred embodiment, more than one photonic crystal microcavity is coated with the same primary target receptor. At the same time, more than one photonic crystal microcavity is coated separately with the same or different control biomolecule or isotype matched control to the primary target receptor. Specificity is thus justified by the simultaneous binding and none thereof in the multiplexed sandwich arrangement. The secondary target that binds to the primary probe biomolecule adds to the primary resonance wavelength shift of the probe biomolecule to the primary target receptor, thereby leading to signal amplification for enhanced device sensitivity.

Another embodiment of the invention provides a sensor comprising a semiconductor material slab with high dielectric constant, supported on the bottom by a cladding with dielectric constant lower than the slab. The bottom cladding is supported by the semiconductor substrate. The core in the slab is defined by the path via which light propagates in the slab. An MMI is defined which splits the power from a single input ridge or rib waveguide into multiple (n) output ridge or rib waveguides where n=1, 2 . . . N. The ridge waveguide on each output arm of the MMI in the first stage can further input light into a cascaded MMI in the second stage and succeeding stages. The number of cascaded stages is m where m=1, 2 . . . M. On each output arm of the $m^{th}$ cascaded MMI, a photonic crystal pattern is defined as a triangular lattice of holes, with a lattice constant $\alpha$, etched into the slab. The photonic crystal waveguide is defined by filling a single row of air holes, from input ridge waveguide transition to the output ridge waveguide transition with the semiconductor slab material. One or more rectangular slots or voids are etched within each photonic crystal waveguide. The photonic crystal waveguide together with the one or more slots that extend along the length of the photonic crystal waveguide define the photonic crystal slot waveguide. The slot extends into the ridge waveguides at both the input and output end of the photonic crystal slot waveguide. A slot mode converter transitions the optical mode from the regular ridge waveguide to the slotted ridge waveguide at both the input and the output end. The slow light guiding wavelength range of each photonic crystal slot waveguide is small. In order to increase the wavelength bandwidth of the device over which slow light guiding is achieved, each photonic crystal waveguide on each M×N ridge waveguide has a different lattice constant for the triangular lattice. In this way, the guided mode transmission bandwidth of each photonic crystal waveguide is different and thus slow light guiding is achieved over a wider wavelength range. Light is coupled into the first stage MMI via a ridge waveguide. Light is out-coupled from the output ridge waveguides of the last cascaded stage MMI into slotted ridge waveguides via mode converters and then into photonic crystal slot waveguides. Each photonic crystal slot waveguide terminates into a slotted ridge waveguide which finally end in M×N output ridge waveguides after a slot mode converter section.

The MMI sections (including all cascaded stages) and all ridge waveguides may be covered with a cover polymer which is optically transparent in the wavelength range over which transmission measurements are performed and has a lower dielectric constant than the slab in the wavelength range over which transmission measurements are performed. For instance, in one embodiment where the slab is made of silicon and the bottom cladding is made of silicon dioxide and the substrate is silicon, and optical transmission measurements are performed in the wavelength range of 1.2 to 1.7 microns, the cover polymer can be SU-8 (Microchem). One skilled in the art will note that the cover polymer can be any optically transparent low loss polymer in the wavelength range between 1.2 to 1.7 microns. An opening is made in the cover polymer by photolithography so that the photonic crystal waveguide regions are totally exposed. In this way, analytes interact with the device in the photonic crystal patterned regions only. In one instance, the analytes interact with the biomolecules coated on top of the photonic crystal microcavities leading to changes in resonance transmission characteristics of the photonic crystal waveguides.

In another embodiment, the sub-wavelength grating couplers, MMI sections (including all cascaded stages) and all ridge waveguides are not covered with any cover polymer. One or more optical waveguides intersect and cross other optical waveguides at the input and output of the photonic crystal patterned regions, the crossing regions comprising gratings etched on both borders of all four waveguide arms at the intersection. A microfluidic channel made from poly dimethyl siloxane (PDMS) made using standard procedures is then bonded to the chips. In the case of bonding PDMS to silicon chips, standard methods have already been described in the art. The walls of the PDMS microfluidic channels are drawn along the length of the crossing waveguides that do not form the main sensor waveguide arms. While crossing optical waveguides, as designed, result in minimal optical loss in the propagating waveguide, the primary purpose in this packaged design is to prevent leakage of fluids from the microfluidic channels from the trenches or voids around the waveguides. In the absence of the crossing waveguides, when the PDMS microfluidic channels are bonded to the silicon chips, a small gap would be left between the PDMS mold and the bottom cladding, in the void regions on either sides of the optical waveguides.

Other methods, that may have been described in the art, to block the trenches around the waveguides, in the case of silicon chips, could include deposition of silicon dioxide, followed by chemical and mechanical polish and planarization. Oxide would be left on the silicon chip only in the regions where the PDMS channel walls cross the optical waveguides defined in the slab. Oxide would be removed from other regions on the chip by wet or dry etching processes. However, the process of deposition and removal of oxide involves several additional fabrication steps. These additional fabrication steps are not required when crossing waveguides are incorporated into the structure, the crossing waveguides being defined in the same step as all other patterns that are defined in the slab. Analytes interact with the device in the photonic crystal patterned regions only. In one instance, the analytes interact with the biomolecules coated on top of the photonic crystal microcavities leading to changes in resonance transmission characteristics of the photonic crystal waveguides.

Multimode-interference (MMI)—based crossings with relatively compact sizes (13 µm×13 µm) have been demonstrated with insertion loss of ~0.2 dB. In this type of structure, the self-focusing effect of the MMI is used to form a single image of the MMI input waveguide mode profile at the crossing, thus minimizing the effect of the crossing waveguide on the mode profile.

For an ideal self-imaging, it is required that $\beta_{m,ideal}=\beta_0-m(m+2)\pi/3L_\pi$ where $\beta_m$ is the propagation constant of mode m, and $L_\pi$ is the beat length of the self-imaging process. One can then write $$\beta_m = \beta_0 \sqrt{1 + \frac{K_{T0}^2 - K_{Tm}^2}{\beta_0}} \quad (1)$$

where $K_{Tm}=(m+1)\pi/W_{em}$ is the transverse wave number of mode m, and $W_{em}$ is the effective width of the MMI for the $m^{th}$ mode. The modal phase error is given as $\Delta\phi_m=L_{MMI}\Delta\beta_m=L_{MMI}(\beta_m-\beta_{m,ideal})$, where $L_{MMI}$ is the MMI length. It has been shown that the lateral cladding index ($n_c$) can be tuned to minimize $\Delta\phi_m$ for a few numbers of dominant modes. Particularly, at the N-folding imaging length, $\Delta\phi_m$ is given as $$\Delta\varphi_m \approx (P/4)\frac{\lambda_0^2(m+1)^4\pi}{2Nn_f^2W_{e0}^2}\left[\frac{1}{8} - \frac{\lambda_0 n_{f2D}^2}{6\pi W_{e0}(n_{f2D}^2 - n_{c2D}^2)^2}\right] \quad (2)$$

where $\lambda_0$ is the optical wavelength and P is the number of self-imaging periods. In order to implement $n_c>1$, a subwavelength nanostructure (SWN) is used to engineer the lateral cladding refractive index. The SWN is periodic along the light propagation direction, and its refractive index ($n_{SWN}$) can be engineered by tuning the filling factor of the air trench inside the SWN, which is defined as the ratio between the air trench width (W) and the SWN period (Λ). A typical Λ=200 nm for the SWN and W=30, 40, 50, 60, 70, and 80 nm etc. The width of the SWN is 200 nm to accommodate the field penetration into the lateral cladding. The lateral cladding index is thus adjusted using SWN by adjusting the grating periodicity and fill factor. It is observed that efficient crossing between waveguides (for silicon waveguides operating at the telecom wavelengths of 1550 nm) is achieved when the cladding index is 2.5, which is achieved by an appropriate choice of SWN period Λ and trench width W. The sub-wavelength nanostructures thus form the integral part of the crossing waveguides at the intersection regions.

The input arm of the MMI in the first stage has a sub-wavelength grating coupler made from a rectangular array of rectangular slots or voids etched into the slab. Each of the M×N output ridge waveguides at the output of the photonic crystal waveguides in each of the M×N output arms has a sub-wavelength grating coupler made from a rectangular array of rectangular slots or voids etched into the slab. The sub-wavelength grating couplers enable light to be coupled via external single mode optical fibers into and out of the ridge waveguides. The sub-wavelength grating couplers at both the input and output may be coated with optically transparent polymer in the wavelength range of transmission, for instance SU-8 (Microchem). One skilled in the art will note that the cover polymer can be any optically transparent low loss polymer in the wavelength range between 1.2 to 1.7 microns. The sub-wavelength grating couplers at both the input and output may also not be covered with any other material.

A microscope glass slide, typically 500 microns thick with a rectangular opening is then bonded to the cover polymer SU-8 (Microchem). One skilled in the art will note that the top glass slide can also be another bare silicon wafer or a silicon wafer with a silicon dioxide or silicon nitride coating or any other semiconductor wafer such as gallium arsenide, indium phosphide, or sapphire that can be bonded to the cover polymer, and is thus referred henceforth as a rigid dielectric layer. Instead of the rigid dielectric and cover polymer, a rectangular block with an opening can be defined in a polymer such as poly-dimethyl siloxane (PDMS) and the PDMS block bonded to the slab material. In this case, a thin film (approximately 5-30 nanometers thick) silicon dioxide would be present on top of the high dielectric constant material of the slab. The thin film of silicon dioxide may be thermal oxide, or oxide deposited by plasma enhanced chemical vapor deposition or sputtered oxide for example. Analytes enter into the chip through the rectangular void and the rigid dielectric layer or the PDMS mold and provides a rugged support for the chip, comprising the substrate, bottom cladding and slab with patterned device elements in the slab. In some embodiments, the rigid dielectric layer may be absent and analytes interact with the photonic crystal waveguides and photonic crystal slot waveguides directly through the opening in the cover polymer. When, instead of the rigid dielectric and cover polymer, a PDMS mold based rectangular block is present, analytes interact with the photonic crystal waveguides and photonic crystal slot waveguides directly through the opening in the PDMS molds.

In one embodiment, light is incident on the sub-wavelength grating couplers from the top via external optical fibers. In one instance light from the optical fiber is incident through the rigid dielectric and the optically transparent cover polymer layers. In another instance, light from the optical fiber is incident from the top on the sub-wavelength grating couplers from external optical fibers through a hole etched in the rigid dielectric, but through the optically transparent cover polymer. In another instance, light from the optical fiber is incident from the top via external optical fibers through a hole etched in the rigid dielectric as well as an opening made in the cover polymer via photolithography in the same step that a hole is opened into the cover polymer to expose the photonic crystal waveguide regions. In another instance, light from the optical fiber is incident from the top directly on the sub-wavelength grating couplers from external optical fibers. Light from the sub-wavelength grating couplers on the output ridge waveguides is coupled out from the output photonic crystal waveguides in the same way as the input coupling of the input optical fiber to the input sub-wavelength grating couplers. The embodiment describes using optical fibers, however, one skilled in the art will note that light can be input via the sub-wavelength grating couplers from external lasers and output via the sub-wavelength grating couplers to external optical detectors. One skilled in the art will also note that the external optical fiber can be attached to the input and output sub-wavelength grating couplers via ultra-violet cured polymer such as epoxy.

In another embodiment, light from an external optical fiber is incident onto the sub-wavelength grating couplers from the bottom of the substrate through a slot or void that is completely etched through the substrate to the bottom cladding. Light from the sub-wavelength grating couplers on the output ridge waveguides is coupled out from the output photonic crystal waveguides in the same way from the bottom through the substrate as the input coupling of the input optical fiber to the input sub-wavelength grating couplers. The embodiment describes the method using optical fibers, however, one skilled in the art will note that light can be input via the sub-wavelength grating couplers from external lasers and output via the sub-wavelength grating couplers to external optical detectors.

The semiconductor chip comprising the substrate, the bottom cladding, the slab with the device elements, the cover polymer, and the rigid dielectric layer or the PDMS polymer molds are placed in a package made of ceramic or plastic. The package has holes that allow the optical fibers or the external light source to interface with the sub-wavelength grating couplers. The rectangular ceramic package is patterned at the four corners with grooves that enable precision positioning of the semiconductor chip with the external measurement setup containing the external input and output optical fibers. The input and output optical fibers in the external measurement setup are precisely aligned to deliver and collect light respectively at maximum efficiency from the input and output sub-wavelength grating couplers.

To summarize:

The primary objective of the invention is to provide a packaged integrated chip for multiplexing photonic crystal microcavity coupled waveguide sensors with compact size that can be monolithically integrated to implement a personalized diagnostic microarray chip and a chip-integrated optical absorption spectrometer respectively. The objective is to build a custom package to efficiently couple light into and out of the chip-integrated sensors from external sources.

The second objective of the invention is to significantly increase measurement throughput from devices by signal collection and analysis from multiple elements of a microarray in photonic crystal microcavity coupled waveguide sensors in a single measurement as opposed to individual element measurement in contemporary systems.

The third objective of the invention is to use crossing optical waveguides primarily from a mechanical perspective, in preventing the leakage of fluids from the microfluidic channels. The crossing optical waveguides at the same time do not result in any significant optical loss and thus preserve the original device characteristics as those without crossing waveguides.

Other objectives and advantages of the present invention will become apparent from the following descriptions, taken in connection with the accompanying drawings, wherein, by way of illustration and example, an embodiment of the present invention is disclosed.

IV. BRIEF DESCRIPTION OF THE DRAWINGS

The drawings constitute a part of this specification and include exemplary embodiments of the present invention, which may be embodied in various forms. It is to be understood that in some instances various aspects of the present invention may be shown exaggerated or enlarged to facilitate an understanding of the invention.

A more complete and thorough understanding of the present invention and benefits thereof may be acquired by referring to the following description together with the accompanying drawings, in which like reference numbers indicate like features, and wherein:

FIG. 1A is a schematic top view drawing showing the design of a microarray device based on a 1×N MMI, with a single input and N outputs. Each output arm can cascade into the input arm of a second stage MMI or in subsequent cascades to an $M^{th}$ stage MMI. The number of output ridge waveguides after the last stage MMI is thus M×N. On each output arm M×N, a photonic crystal waveguide is present and an array of P photonic crystal microcavities are coupled to that photonic crystal waveguide. In FIG. 1A, N is chosen as 4 and M is chosen as 2 and P is chosen arbitrarily as 1 or 2. P can be equal to P=1, 2, 3, 4, 5, or 6 photonic crystal microcavities along the length of a single photonic crystal waveguide on each arm of the MMI. Sub-wavelength grating couplers at the input and output, couple light from external optical sources into the optical waveguides. Crossing optical waveguides are defined at the input and output of the photonic crystal patterned regions. The crossing waveguides run substantially orthogonal to all the waveguides in all M×N arms at the input and output of the photonic crystal patterned regions.

FIG. 1B is a schematic top view drawing showing one embodiment of the design of a microarray device based on a 1×N MMI, with a single input and N outputs. Each output arm can cascade into the input arm of a second stage MMI or in subsequent cascades to an M$^{th}$ stage MMI. The number of output ridge waveguides after the last stage MMI is thus M×N. Each of the M×N waveguides, prior to the photonic crystal patterned regions, can be designated as primary waveguides. On each output arm M×N, a photonic crystal waveguide is present and an array of P photonic crystal microcavities are coupled to that photonic crystal waveguide. In FIG. 1B, N is chosen as 4 and M is chosen as 2. P is chosen as 1 or 2, where, in each photonic crystal waveguide that is connected in series, 1 or 2 photonic crystal microcavities are coupled to each photonic crystal waveguide. In FIG. 1B, 2 series cascaded stages of photonic crystal microcavity coupled waveguides are shown, Q=2. The number of series connected photonic crystal microcavity coupled waveguides is Q=1, 2, 3, 4, 5, 6 or more being only determined by the signal to noise ratio of the output signal from the output subwavelength grating couplers, that can be measured by a photodetector or optical spectrum analyzer. Sub-wavelength grating couplers at the input and output, couple light from external optical sources into the optical waveguides. The ridge waveguides that follow the last cascaded photonic crystal patterned region, on each of the M×N arms, prior to the output sub-wavelength grating couplers are also designated as primary waveguides. Crossing optical waveguides are defined, as shown, substantially orthogonal to the primary optical waveguides on the M×N arms, at the input and output regions of the photonic crystal patterned regions.

FIG. 1C and FIG. 1D show four series connected photonic crystal waveguides with coupled photonic crystal microcavities. A single photonic crystal microcavity is coupled to each single photonic crystal waveguide in series. In each case, P=1, Q=4. In FIG. 1C, each photonic crystal waveguide cascaded in series has an input and output photonic crystal impedance taper with gradually changed group index at the input and output end of the functional photonic crystal waveguide, which can bridge the refractive indices difference between conventional optical waveguides and the functional photonic crystal waveguide. The input and output impedance tapers are created by gradually moving out the holes at the input and output of each photonic crystal waveguide section, away from the photonic crystal waveguide, normal to the photonic crystal waveguide in the plane of the slab over s=4 lattice periods. In FIG. 1D, the there are no input or output impedance tapers at the input and output ends of the functional photonic crystal waveguides. The output transmission spectrum measured at the output subwavelength grating coupler for the device in FIG. 1C is shown in FIG. 1E. The output transmission spectrum measured at the output subwavelength grating coupler for the device in FIG. 1D is shown in FIG. 1F. Two other possible configurations for the group index variations that form the input and output impedance tapers are shown in FIG. 1G and FIG. 1I. In FIG. 1G, the diameter of the holes at the input and output impedance taper regions are gradually reduced from the photonic crystal waveguide section to the input ends (and output ends) of the photonic crystal patterned regions. A magnified view of the input and output impedance tapers of FIG. 1G is shown in FIG. 1H. In FIG. 1I, the diameter of the holes at the input and output impedance taper regions are also gradually reduced from the photonic crystal waveguide section to the input ends (and output ends) of the photonic crystal patterned regions. In addition, the holes at the input and output impedance taper regions are gradually moved out at the input and output of each photonic crystal waveguide section, away from the photonic crystal waveguide section, normal to the photonic crystal waveguide in the plane of the slab over s=4 lattice periods. A magnified view of the input and output impedance tapers of FIG. 1I is shown in FIG. 1J.

FIG. 2A is an enlarged schematic top view of a section of the cascaded MMI.

FIG. 2B is an enlarged schematic top view of the waveguide intersection region H, of the crossing optical waveguide with a representative primary waveguide, as shown in FIG. 2A. FIG. 2B shows the situation when the waveguide intersection comprises one single crossing waveguide (w=1). FIGS. 2C and 2D are representative of waveguide intersections when w=5 and 10 crossing waveguides, respectively, that cross the primary waveguides. One skilled in the art will note that w can be any number w=1, 2, 3 . . . , 1000. From device integration perspective, one obviously chooses a design with minimum w. The crossing waveguides are also defined in the slab. The value of w is determined by the minimum number of crossing waveguides that are needed to ensure that the PDMS molds that form the microfluidic channels adhere well to the slab material comprising the crossing waveguides in the waveguide crossing regions. FIG. 2E is an enlarged schematic top view of a single intersection region H1 shown in FIGS. 2A, 2B, 2C, and 2D. The toothed grating structure exists at each intersection of each ridge waveguide of the crossing waveguide with the primary waveguide in FIGS. 2C and 2D.

Figure 2A:
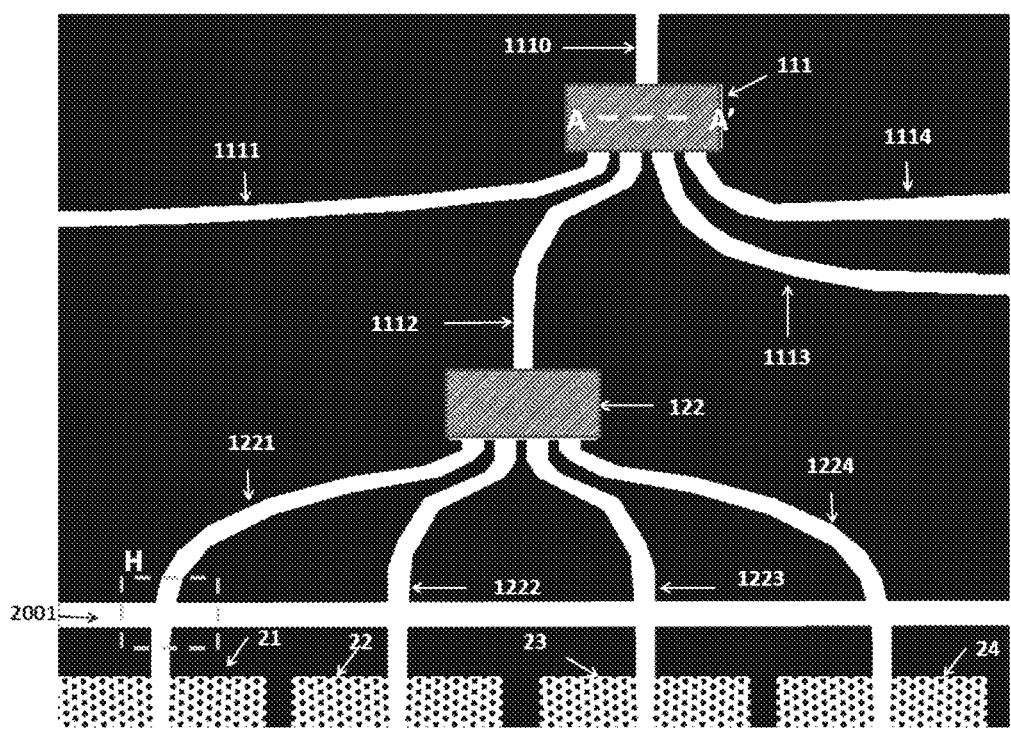
Figure 2B:
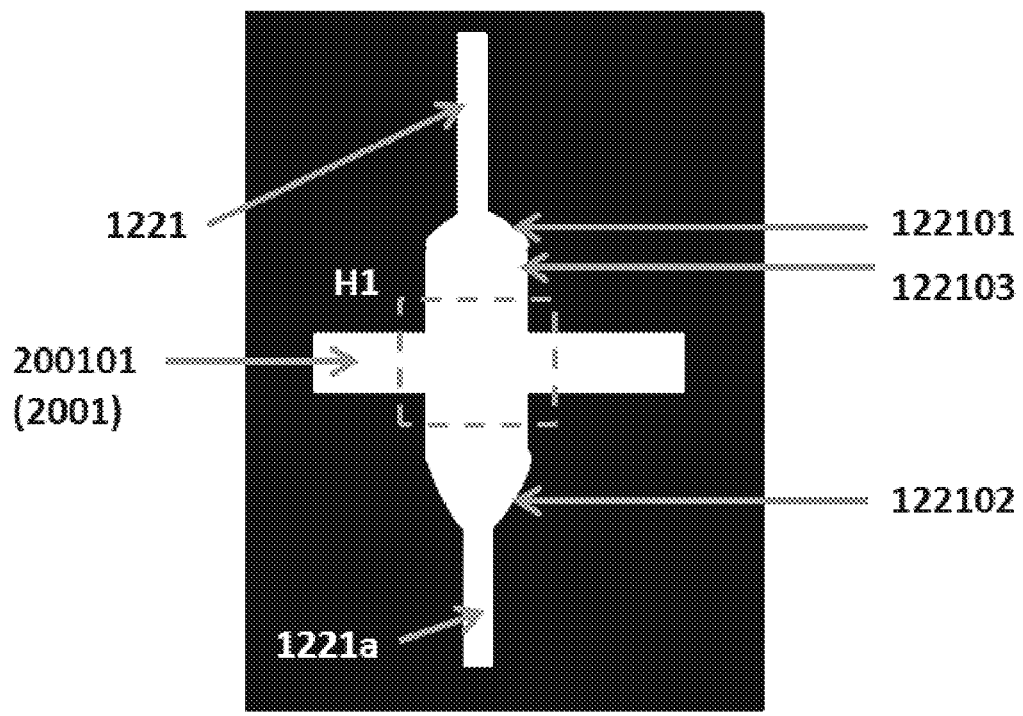
Figure 2C:
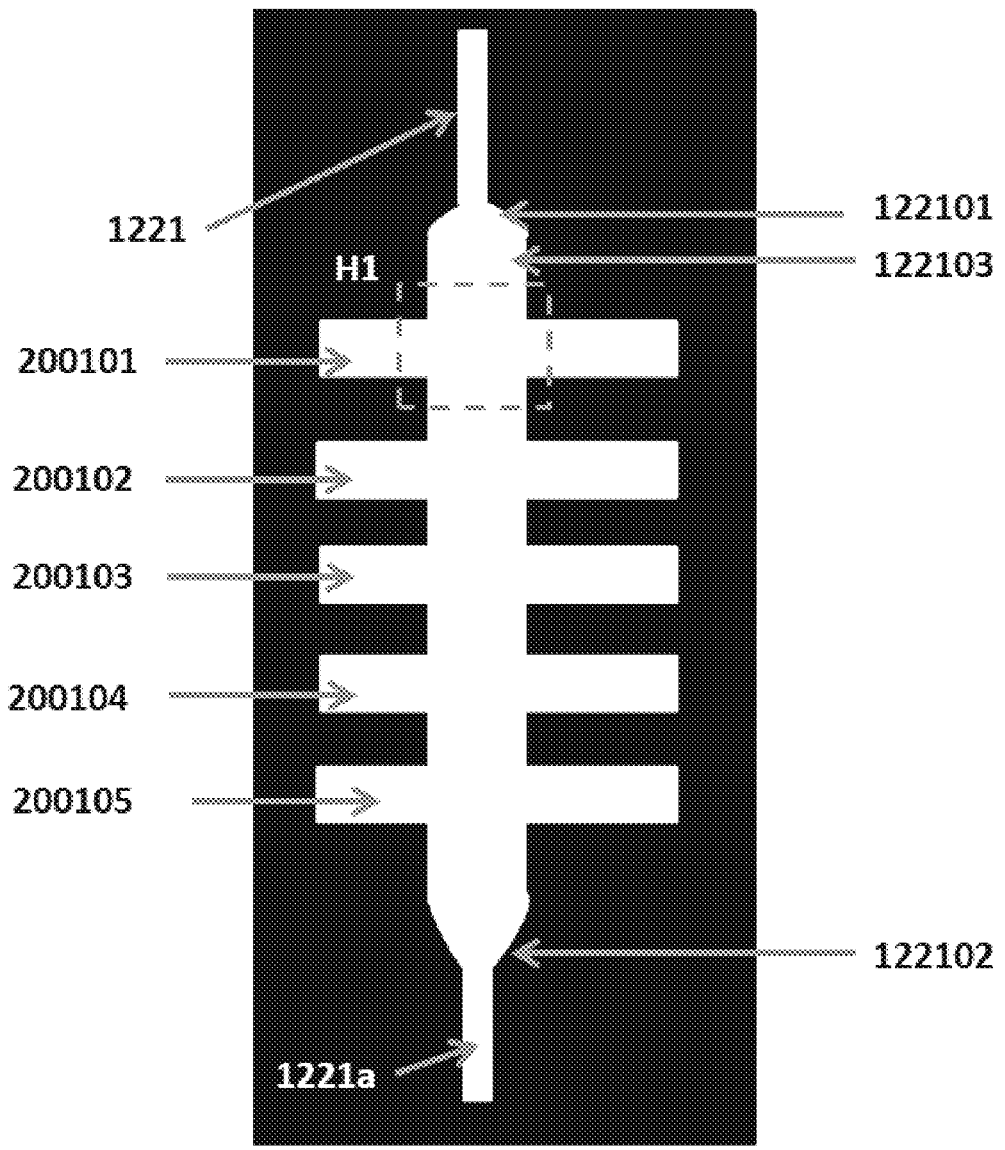
Figure 2D:
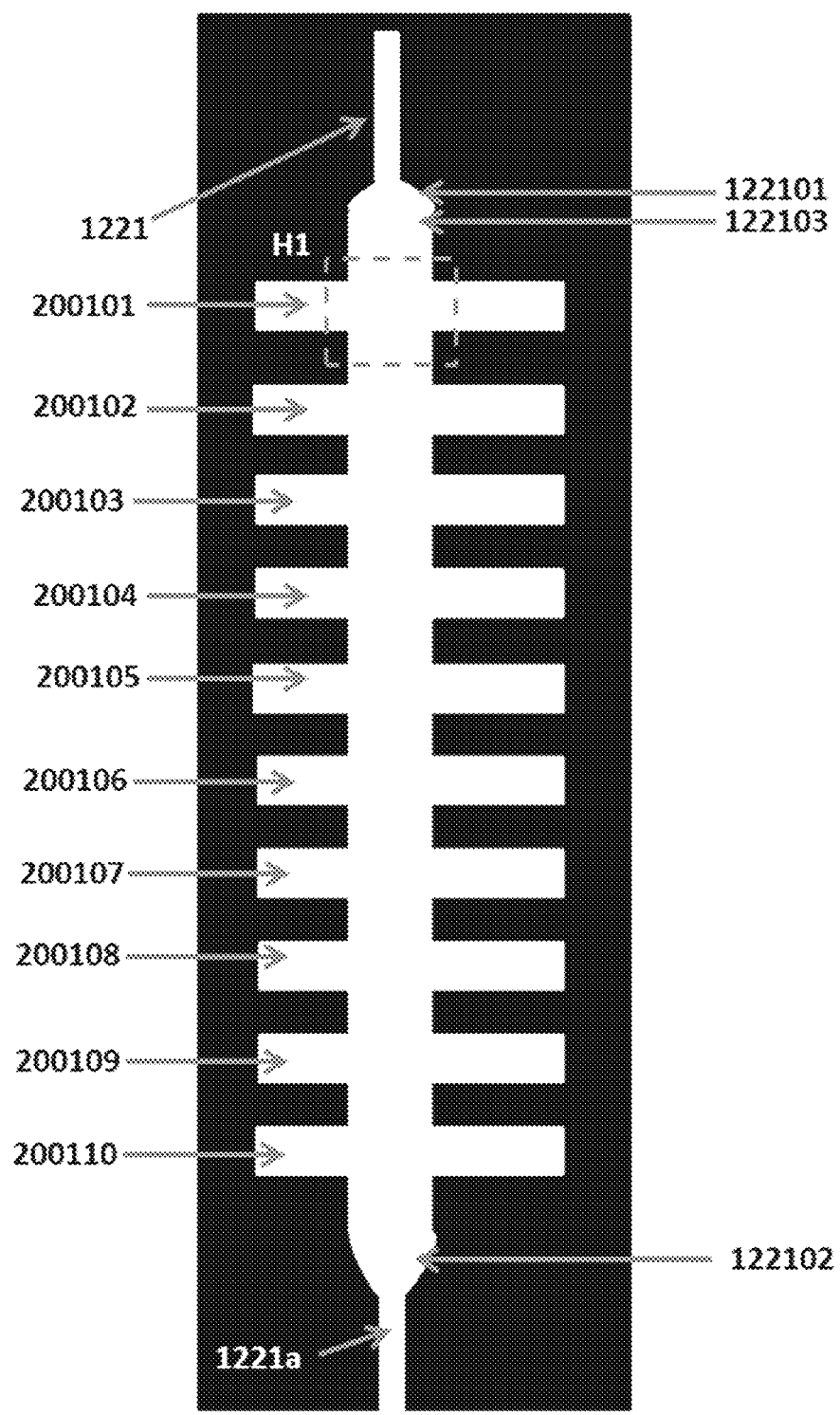
Figure 2E:
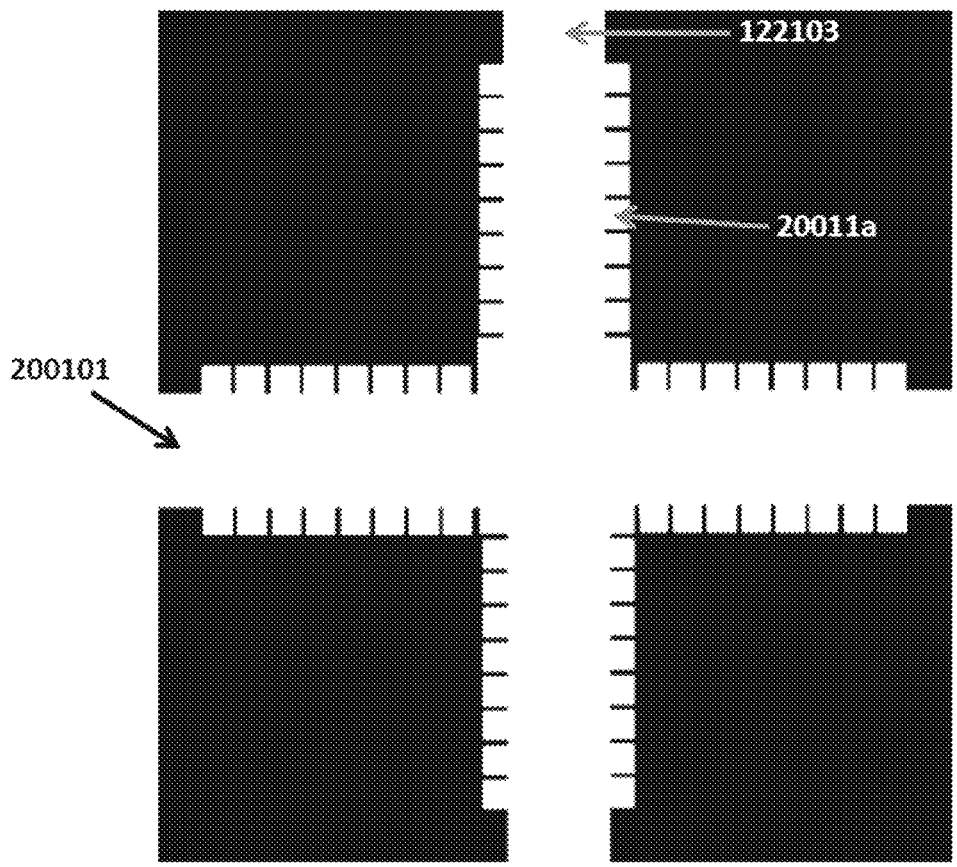
Figure 3A:
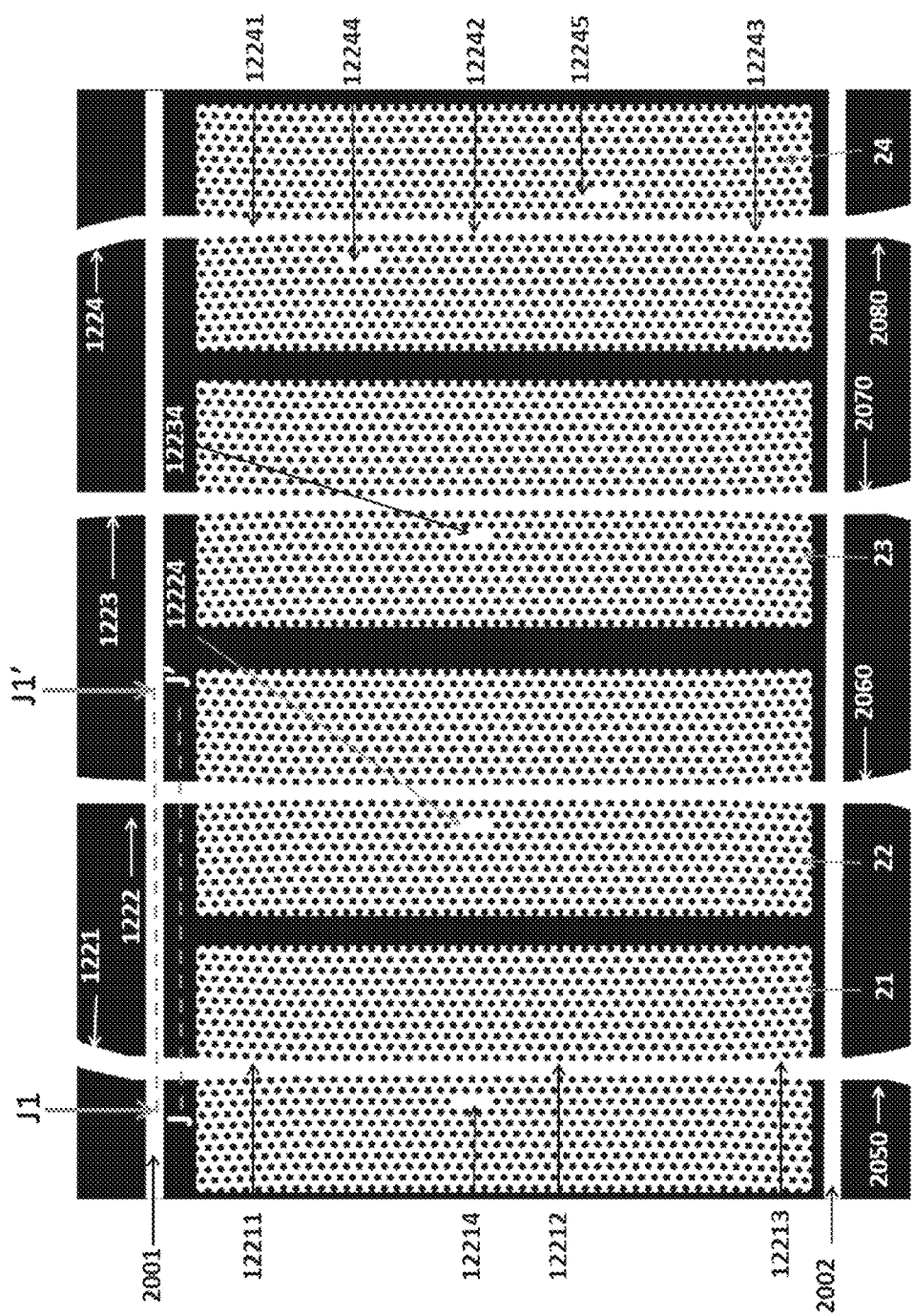
FIG. 3A is an enlarged top view of the photonic crystal waveguide section.
Figure 3B:
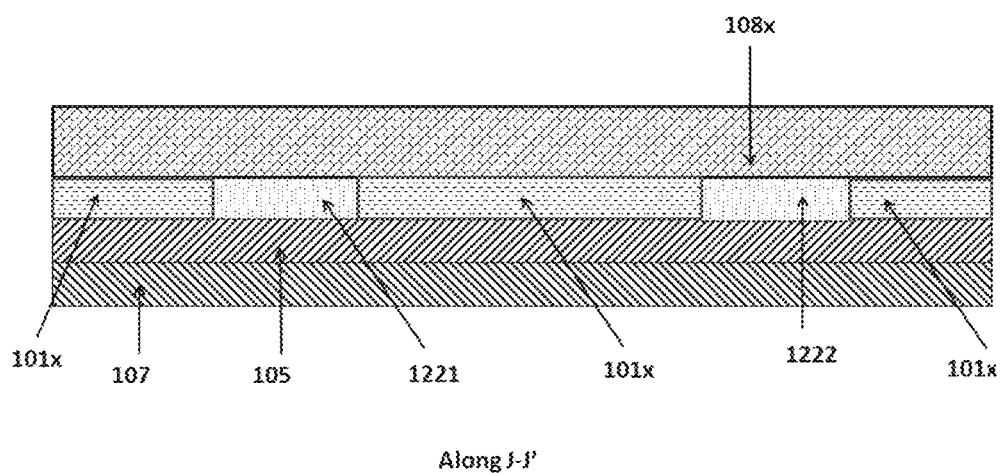
FIG. 3B shows a cross section of the device along the line J-J' from FIG. 3A. We assume that the PDMS mold is bonded on top.
Figure 3C:
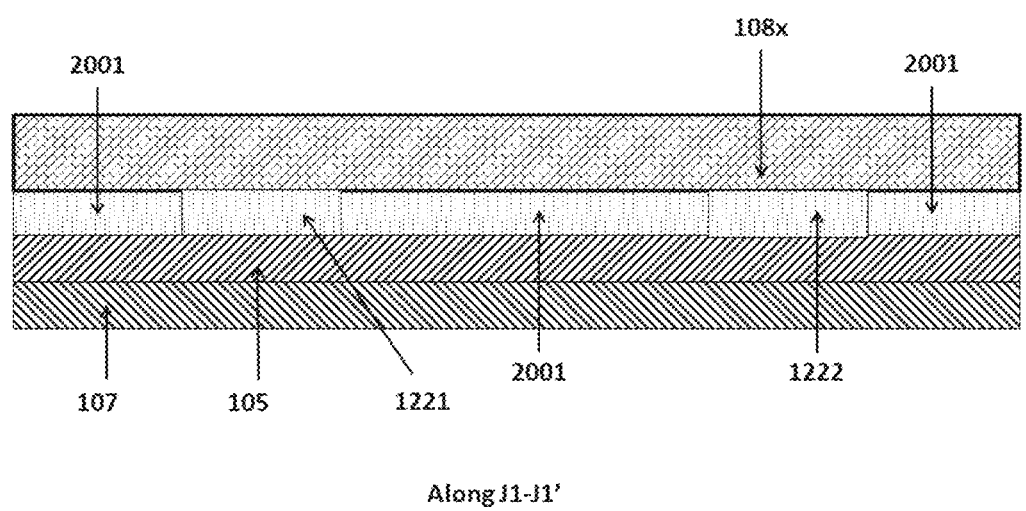

FIG. 3C shows a cross section of the device along the line J1-J1' from FIG. 3A. We also assume that the PDMS mold is bonded on the chip. A void exists between the waveguides in FIG. 3B. In FIG. 3C, the void has been closed by the crossing waveguide. We assume in FIG. 3C that w=1. The same cross-section will exist in each and every waveguide cross-section J1-J1' at each intersection of the waveguides comprising the crossing waveguide with the primary waveguide(s). While FIG. 2A, FIG. 2B, FIG. 2C, FIG. 2D, and FIG. 2E together with the cross-section of the device along the lines J-J' and J1-J1' in FIG. 3B and FIG. 3C respectively have been shown on the input side of each of the photonic crystal patterned region, one skilled in the art will realize that the same cross-sections occur at the crossing regions of the crossing waveguides with the primary waveguides on the output side of each of the photonic crystal patterned regions.

Figure 4:
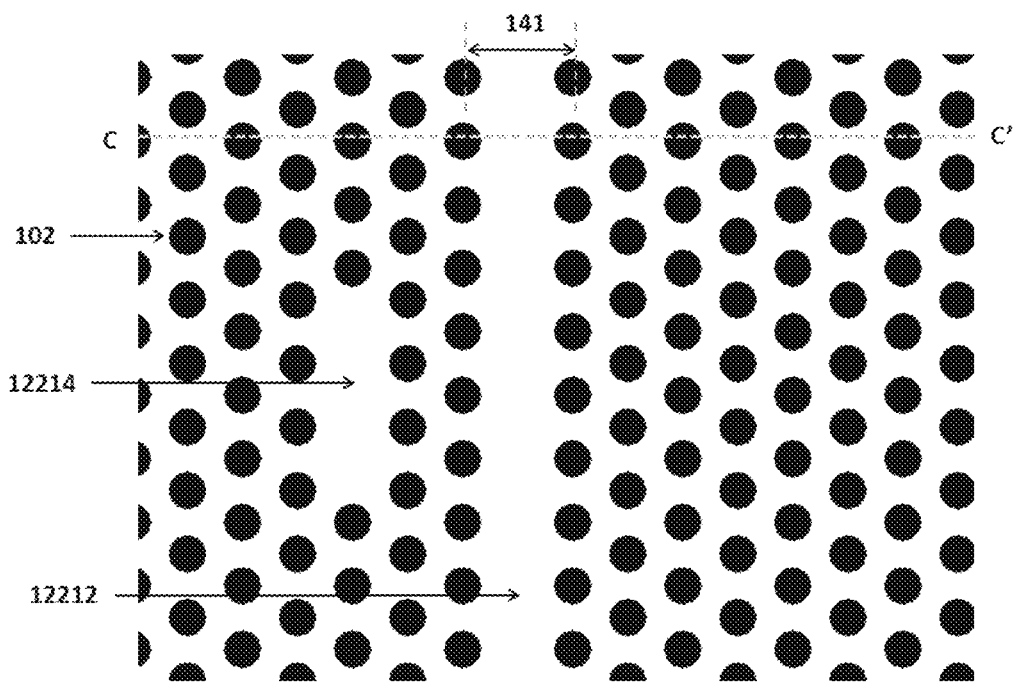

FIG. 4 is an enlarged top view showing the photonic crystal microcavity coupled to the photonic crystal waveguide.

Figure 5:
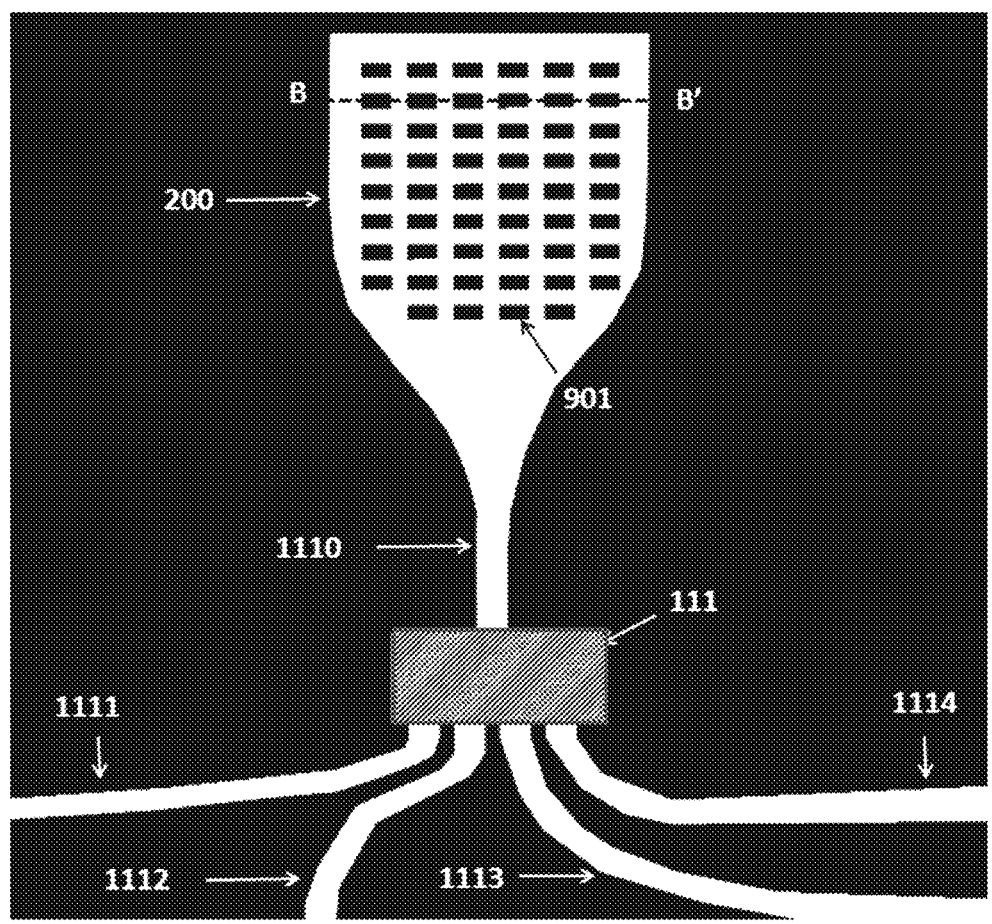

FIG. 5 is an enlarged top view of the input sub-wavelength grating coupler that inputs light to the first cascaded stage of the MMI.

Figure 6:
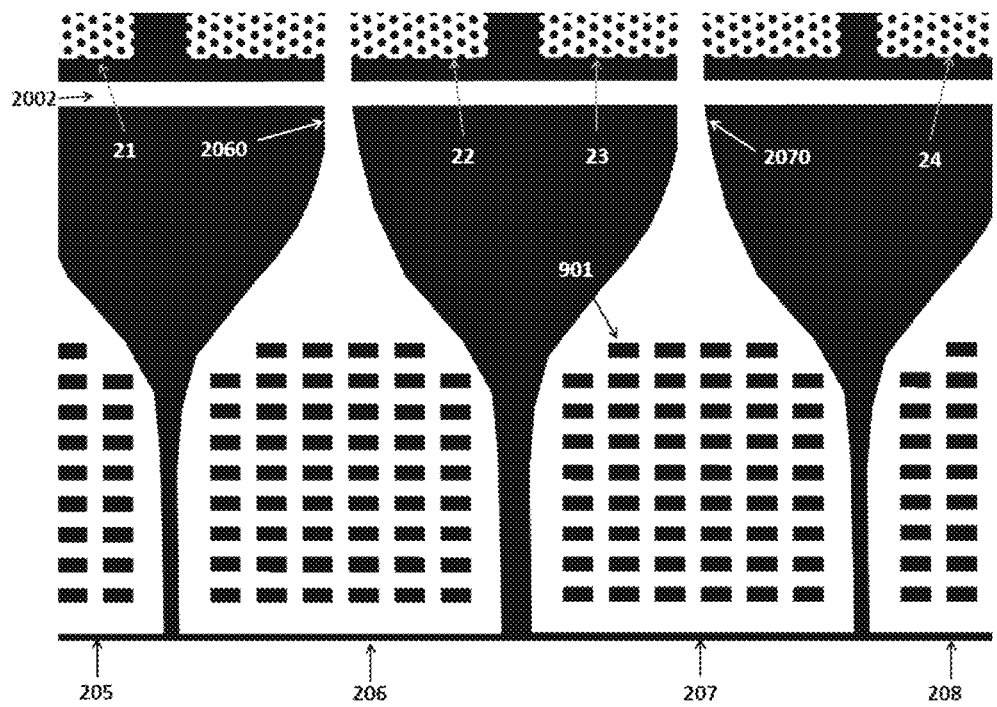

FIG. 6 is an enlarged top view of the output sub-wavelength grating couplers.

Figure 7:
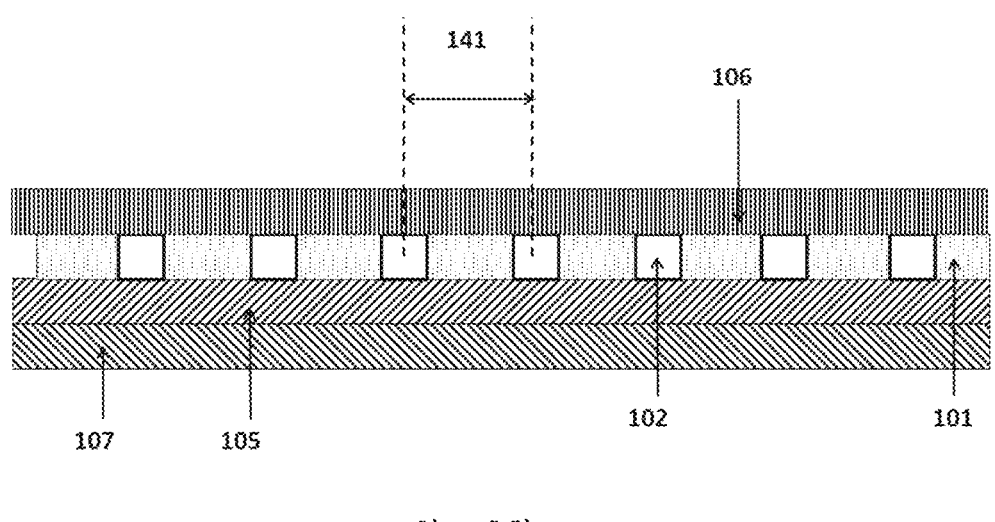

FIG. 7 is a cross-sectional view of the device in FIG. 4 along the plane C-C'.

Figure 1A:
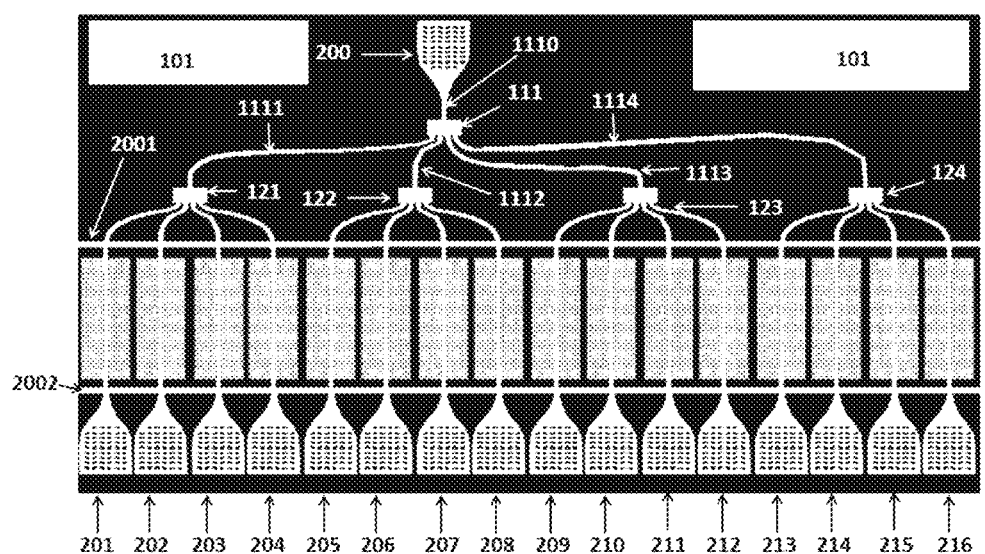
Figure 8A:
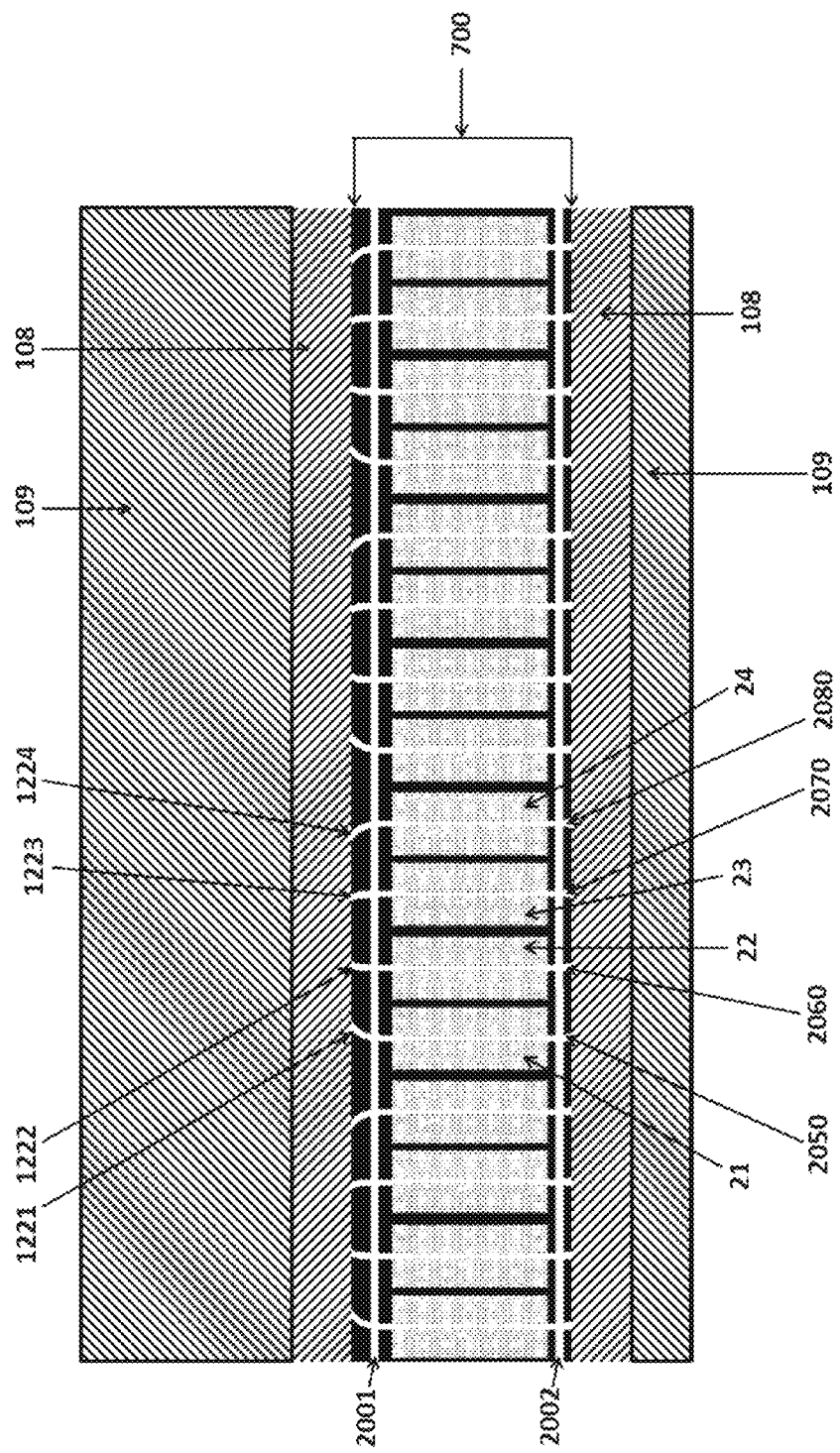
Figure 8B:
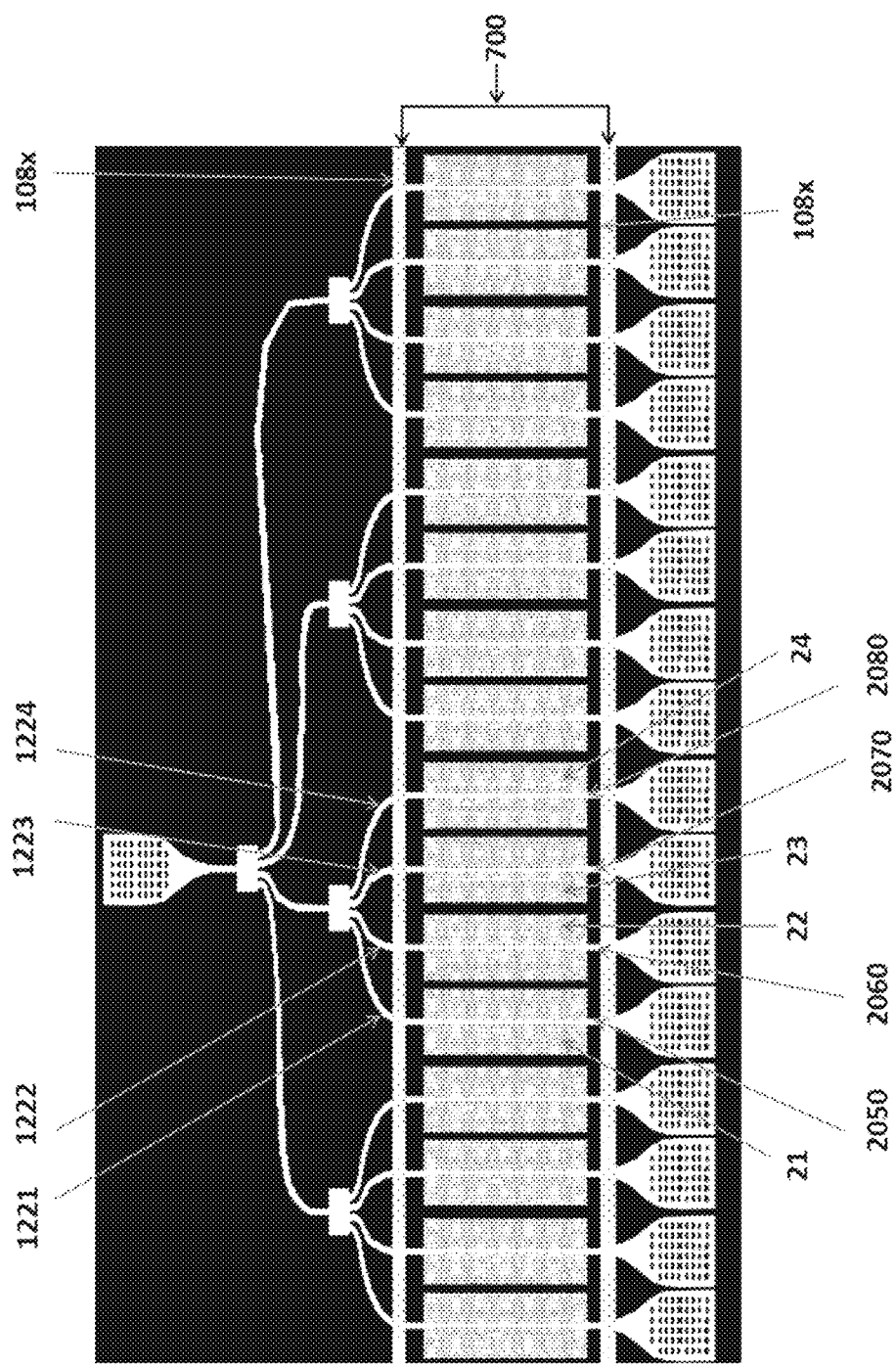

FIG. 8A is a top view of the device in FIG. 1A together with the top layer cover polymer and rigid dielectric cover to form a microfluidic channel. In an alternative embodiment, the top layer cover polymer and rigid dielectric are absent and instead the PDMS microfluidic channel mold is laid out as shown in FIG. 8B.

Figure 9A:
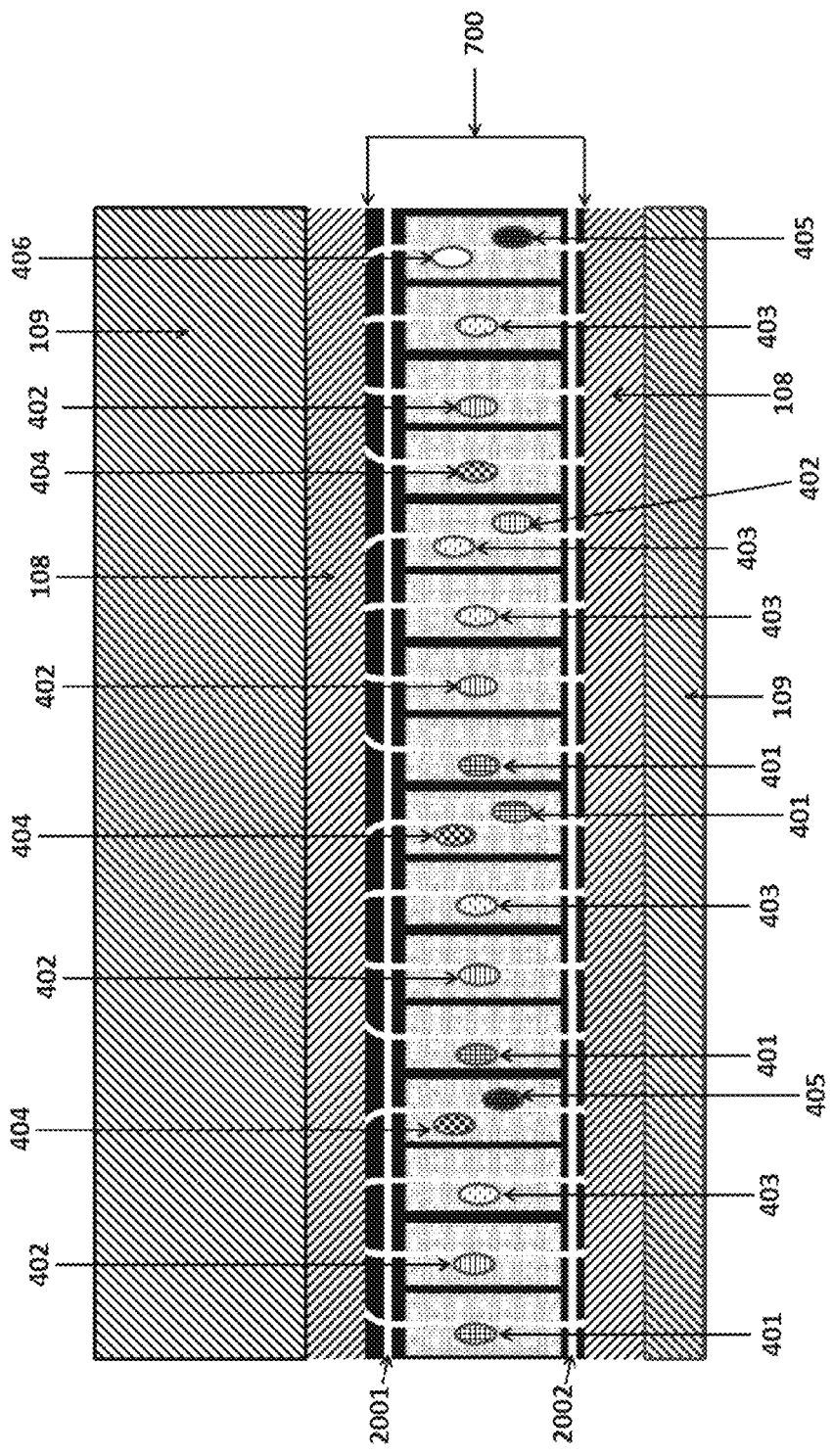
Figure 9B:
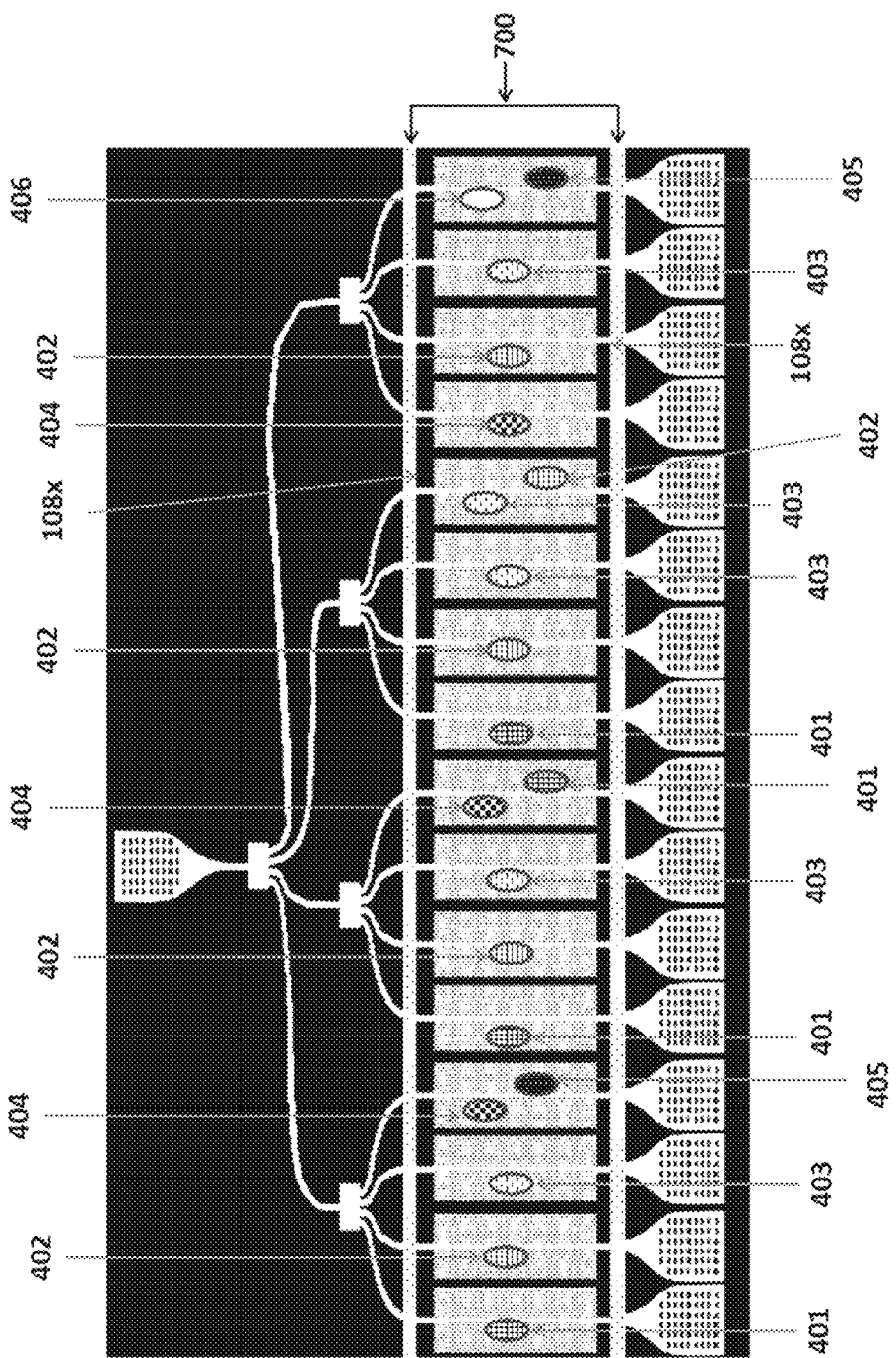

FIG. 9A is the top view of the device in FIG. 8A showing the disposition of one or more, same or different, polymer molecules or biomolecules on the one or more photonic crystal microcavities. FIG. 9B is the top view of the device in FIG.

8B showing the disposition of one or more, same or different, polymer molecules or biomolecules on the one or more photonic crystal microcavities.

Figure 10A:
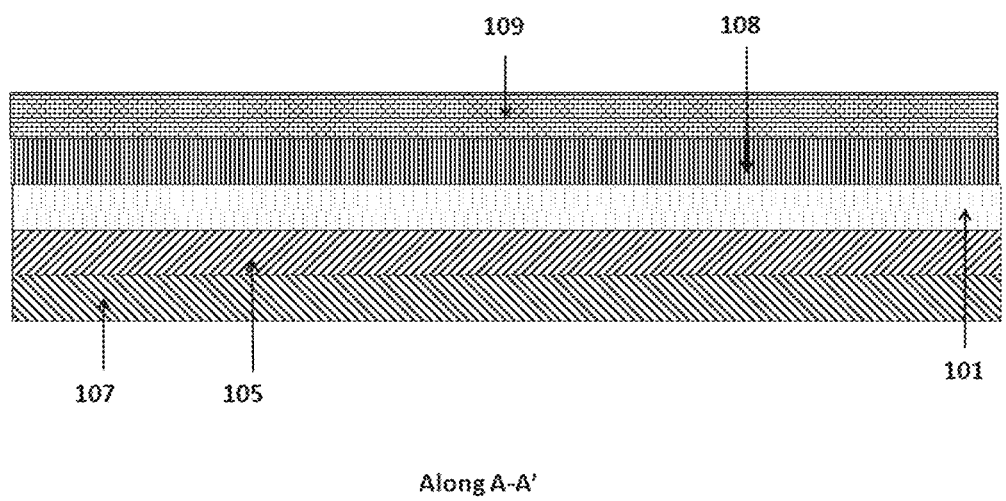
Figure 10B:
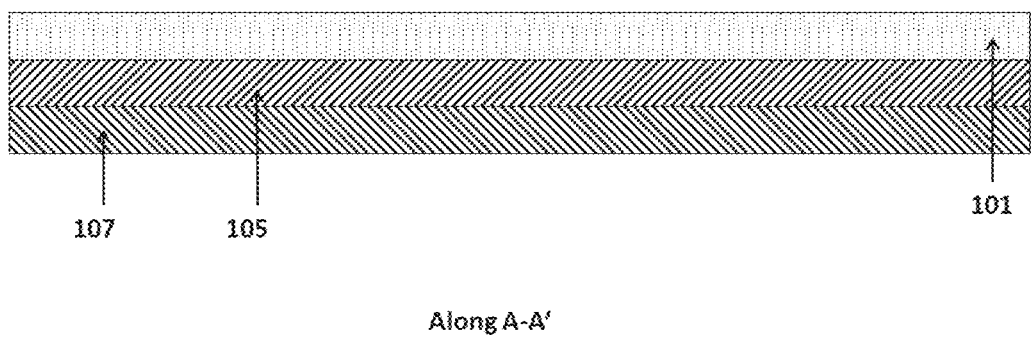

FIG. 10A is a cross-sectional view of the device in FIG. 2A along the plane A-A', and also including the top cover polymer layer and the rigid dielectric cover. FIG. 10B is a cross-sectional view of the device in FIG. 2A along the plane A-A', without the top cover polymer layer and the rigid dielectric cover. When PDMS microfluidic channel molds are used, the polymer layer and rigid dielectric covers are absent.

Figure 11A:
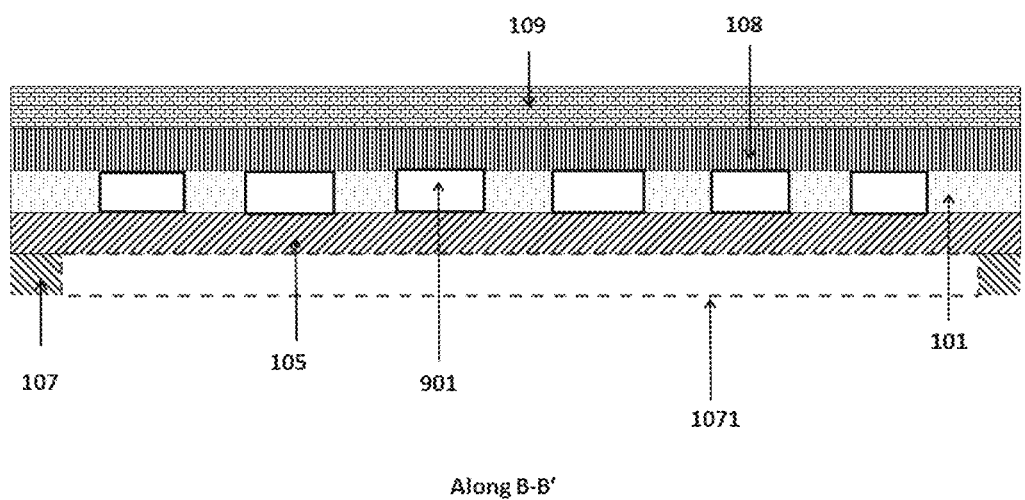
Figure 11B:
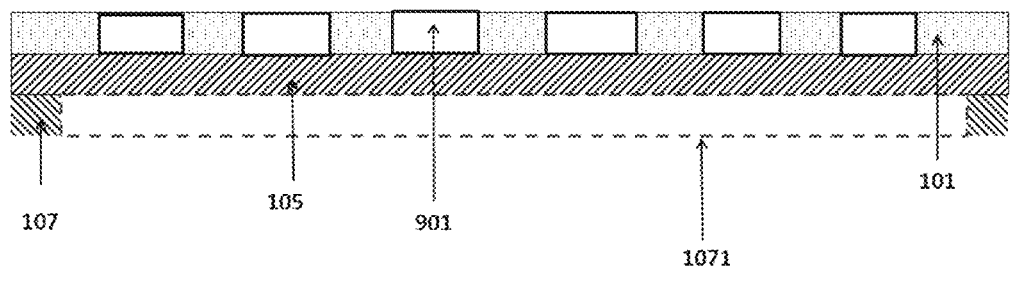

FIG. 11A is a cross-sectional view of the device in FIG. 5 along the plane B-B', and also including the top cover polymer layer and the rigid dielectric cover. FIG. 11B is a cross-sectional view of the device in FIG. 5 along the plane B-B', without the top cover polymer layer and the rigid dielectric cover. When PDMS microfluidic channel molds are used, the polymer layer and rigid dielectric covers are absent.

Figure 12:
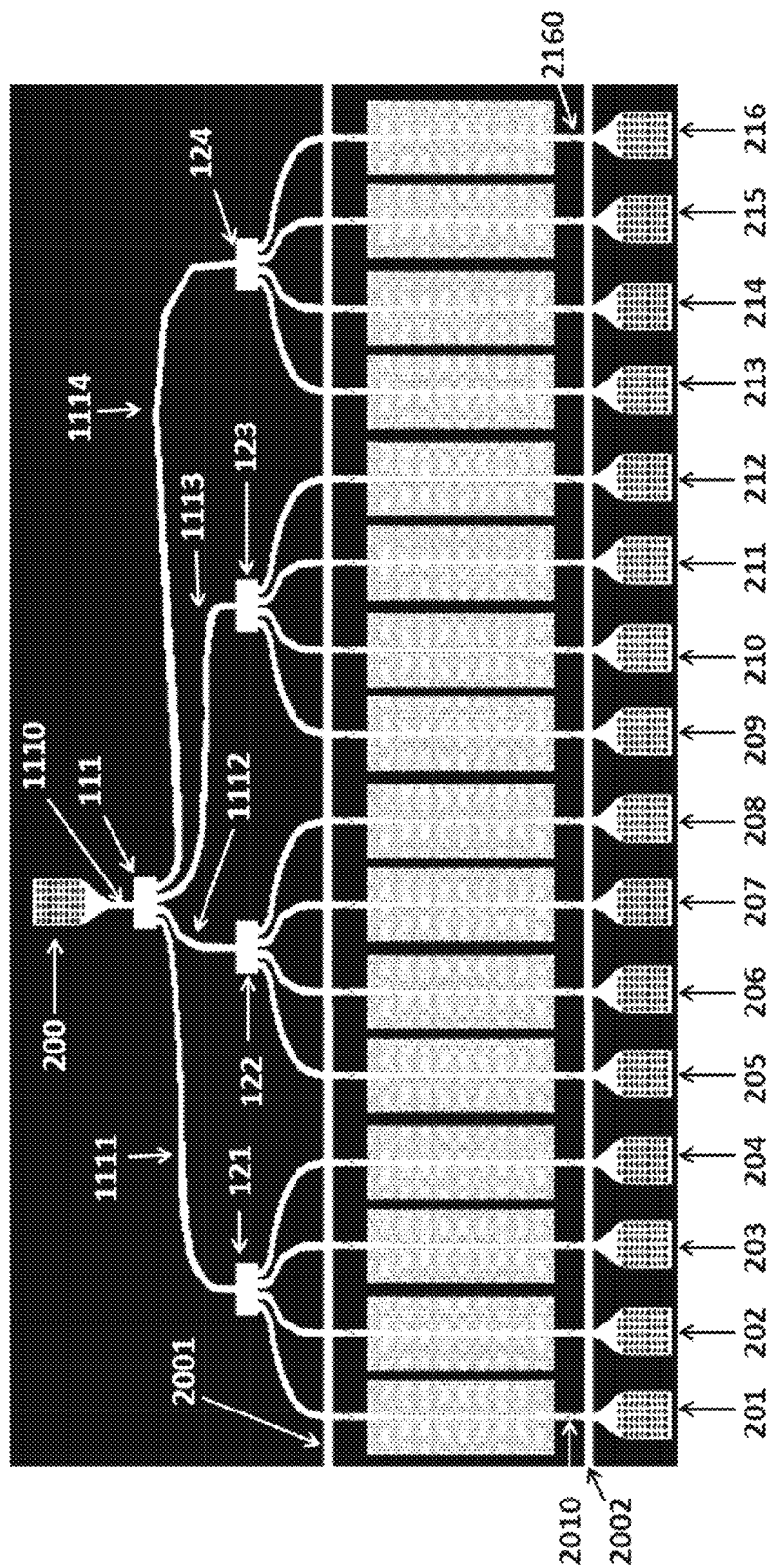

FIG. 12 is a schematic top view showing the design of a photonic crystal slot waveguide array device based on a 1×N MMI, with a single input and N outputs. Each output arm can cascade into the input arm of a second stage MMI or in subsequent cascades to an $M^{th}$ stage MMI. The number of output ridge waveguides after the last stage MMI is thus M×N. Photonic crystal slot waveguides are defined on each (M×N)$^{th}$ waveguide.

Figure 13:
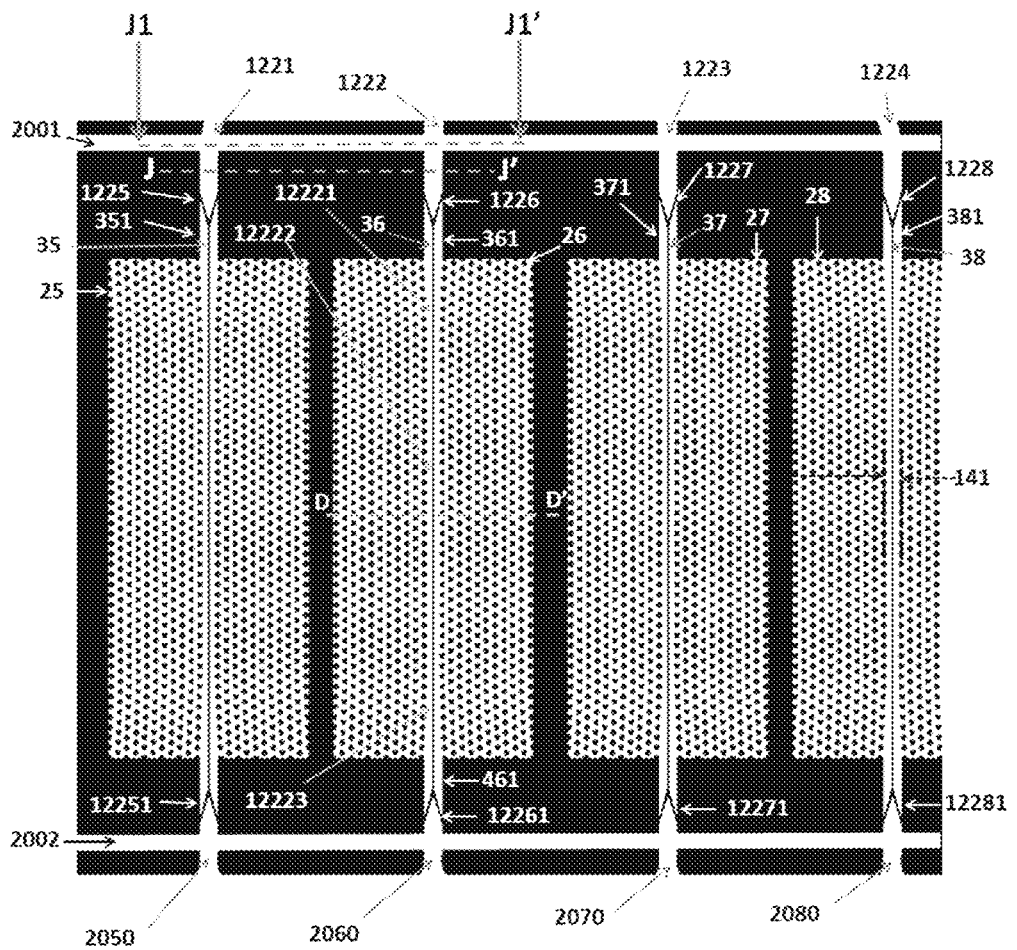

FIG. 13 is an enlarged top view showing the photonic crystal slot waveguide device that is arrayed in the package. One skilled in the art will realize that the same cross-sections occur at the crossing regions of the crossing waveguides with the primary waveguides on the input side and the output side of each of the photonic crystal patterned regions, similar to the cross-section of the device along the lines J-J' and J1-J1' in FIG. 3B and FIG. 3C, respectively. One skilled in the art will realize that the structure of the crossing waveguides that cross the primary waveguides in FIG. 12 and FIG. 13 are the same as those shown in FIG. 2A, FIG. 2B, FIG. 2C, FIG. 2D, and FIG. 2E for FIG. 1A and FIG. 1B.

Figure 14:
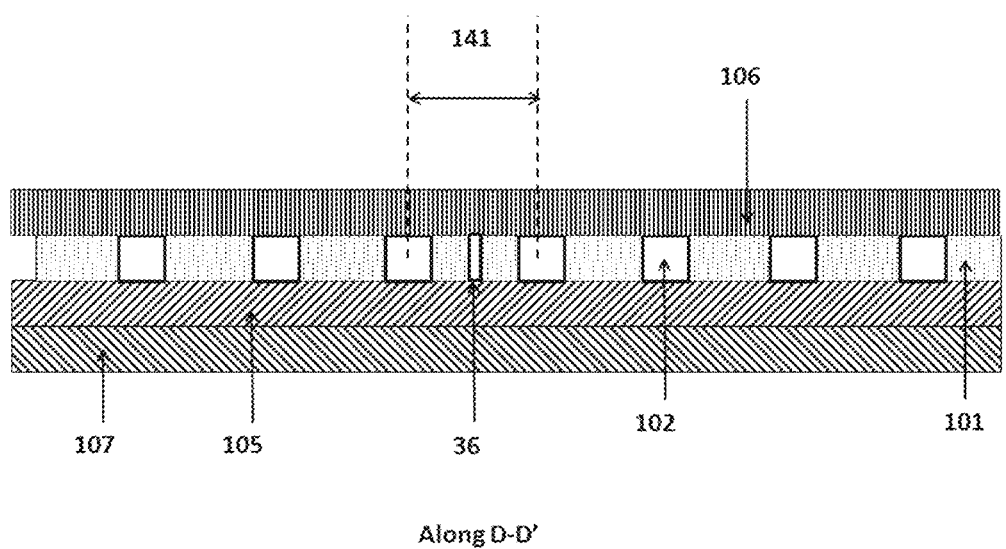

FIG. 14 is a cross-section of the device in FIG. 13 along the plane D-D'.

Figure 15A:
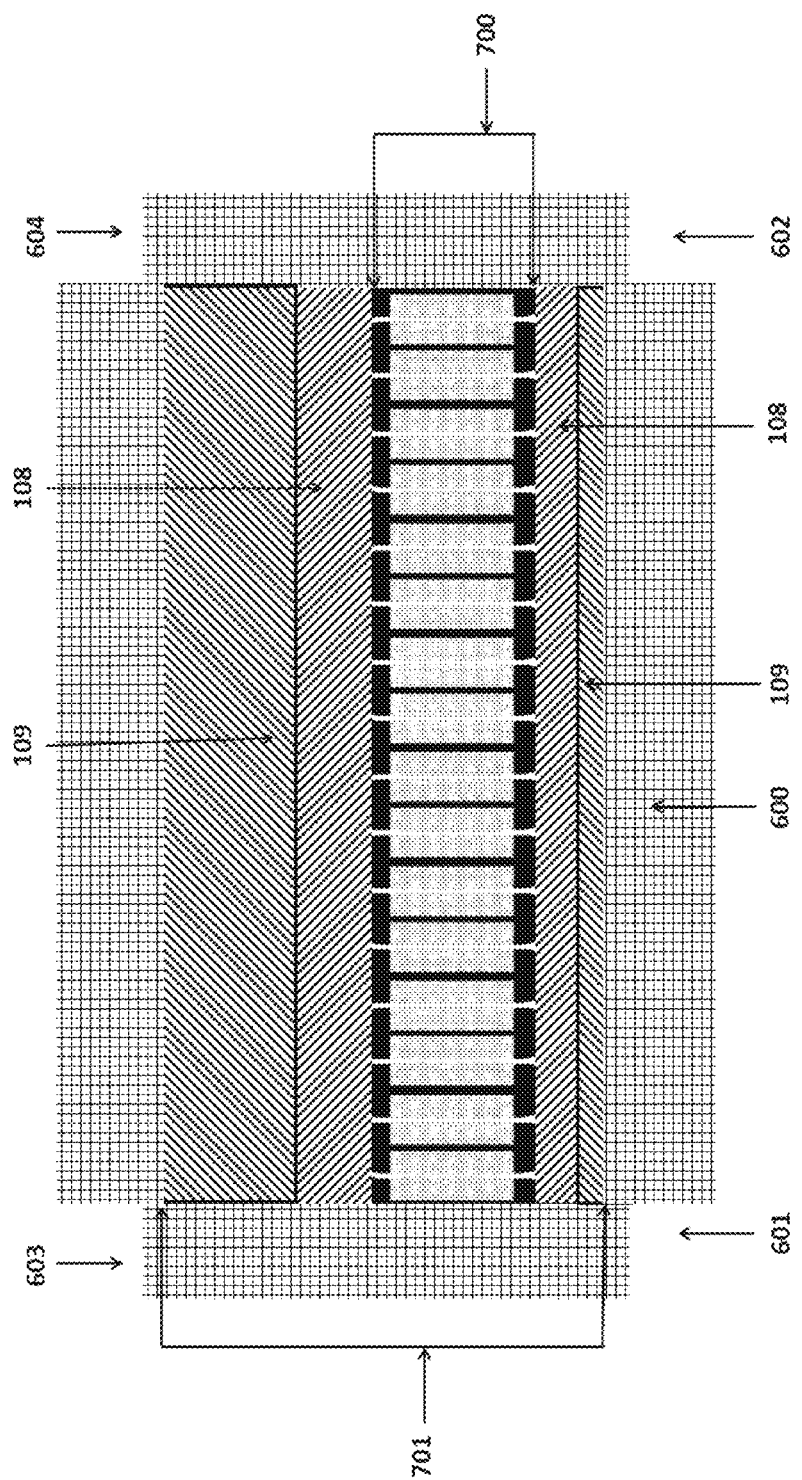
Figure 15B:
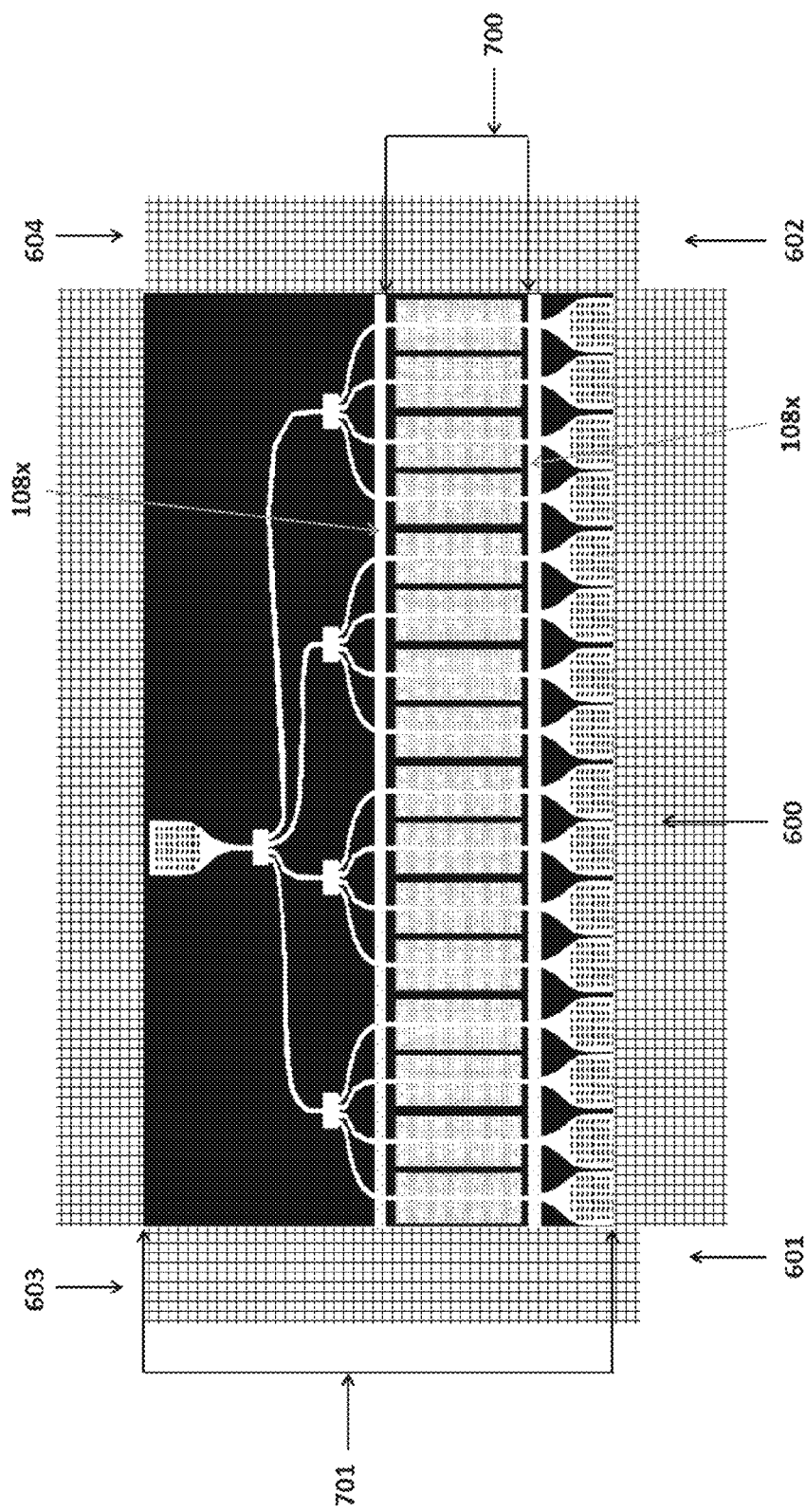

FIG. 15A is a top view of the arrayed device within an outer package including the top cover polymer layer and the rigid dielectric cover. FIG. 15B is a top view of the arrayed device within an outer package including the PDMS microfluidic channel mold. When PDMS microfluidic channel molds are used, the polymer layer and rigid dielectric covers are absent.

Figure 16:
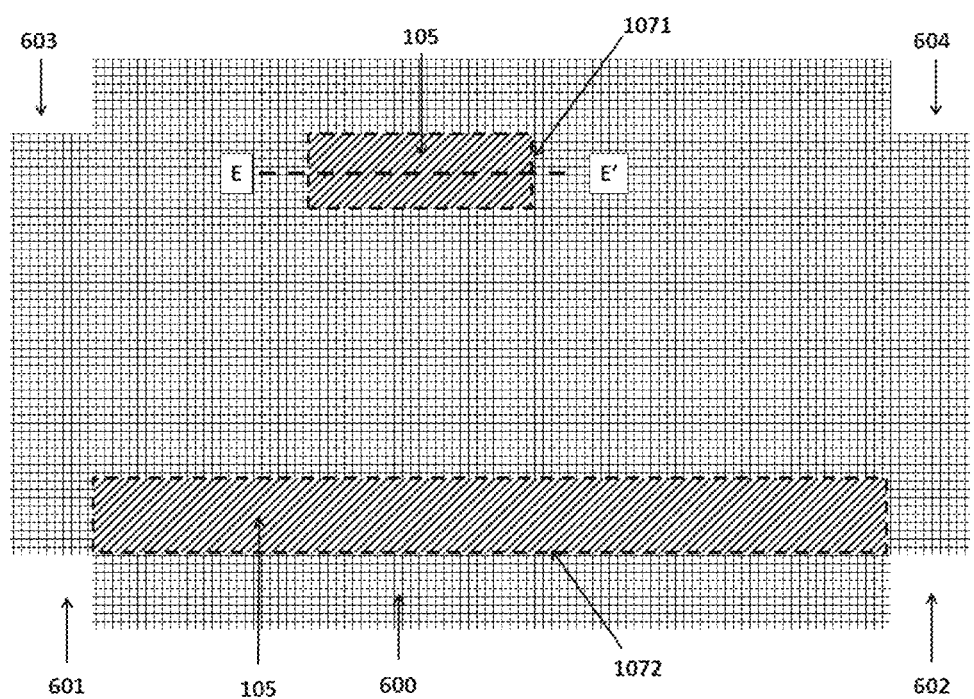

FIG. 16 is bottom view of the outer package showing the opening through which light is coupled from external optical sources into the chip.

Figure 17A:
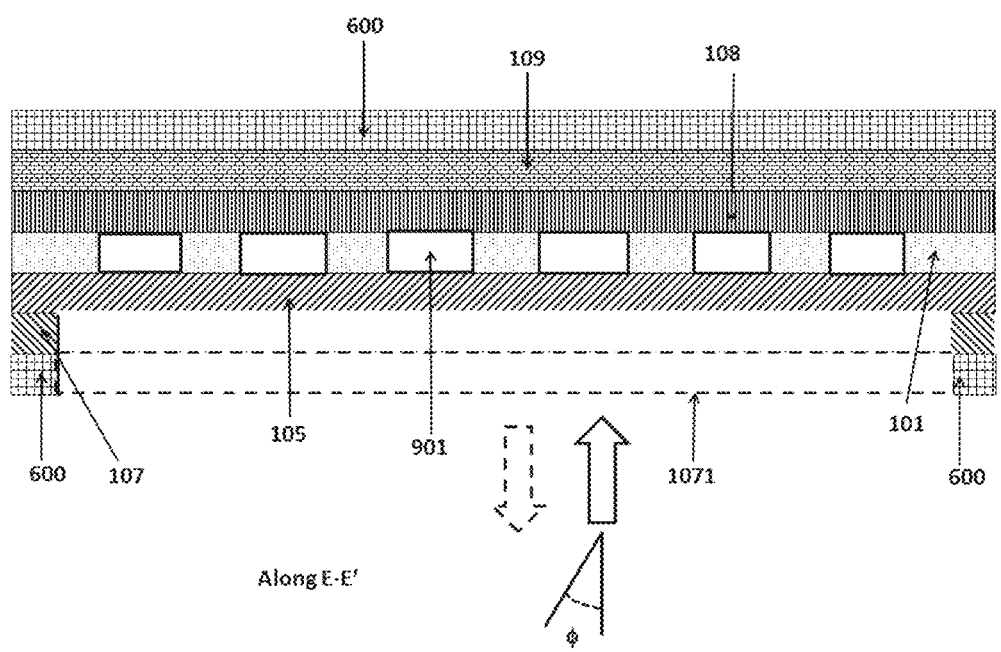
Figure 17B:
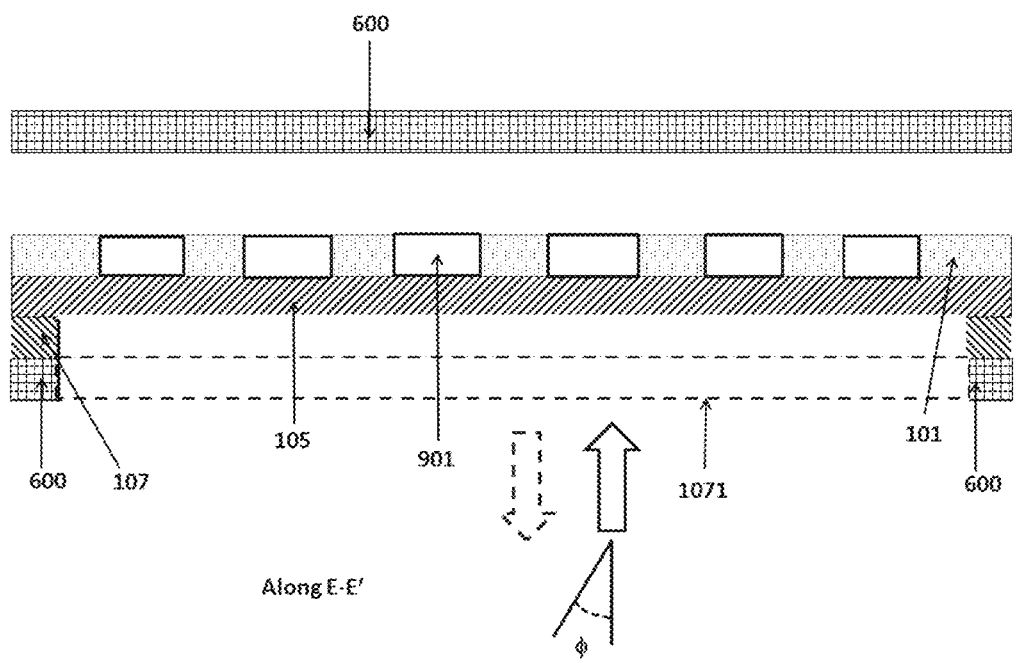

FIG. 17A is cross-section view of the package with the chip inside along the plane E-E' in FIG. 16. FIG. 17B is cross-section view of the package with the chip inside along the plane E-E' in FIG. 16, when the cover polymer and rigid dielectric are absent and instead replaced by a PDMS microfluidic channel.

Figure 18A:
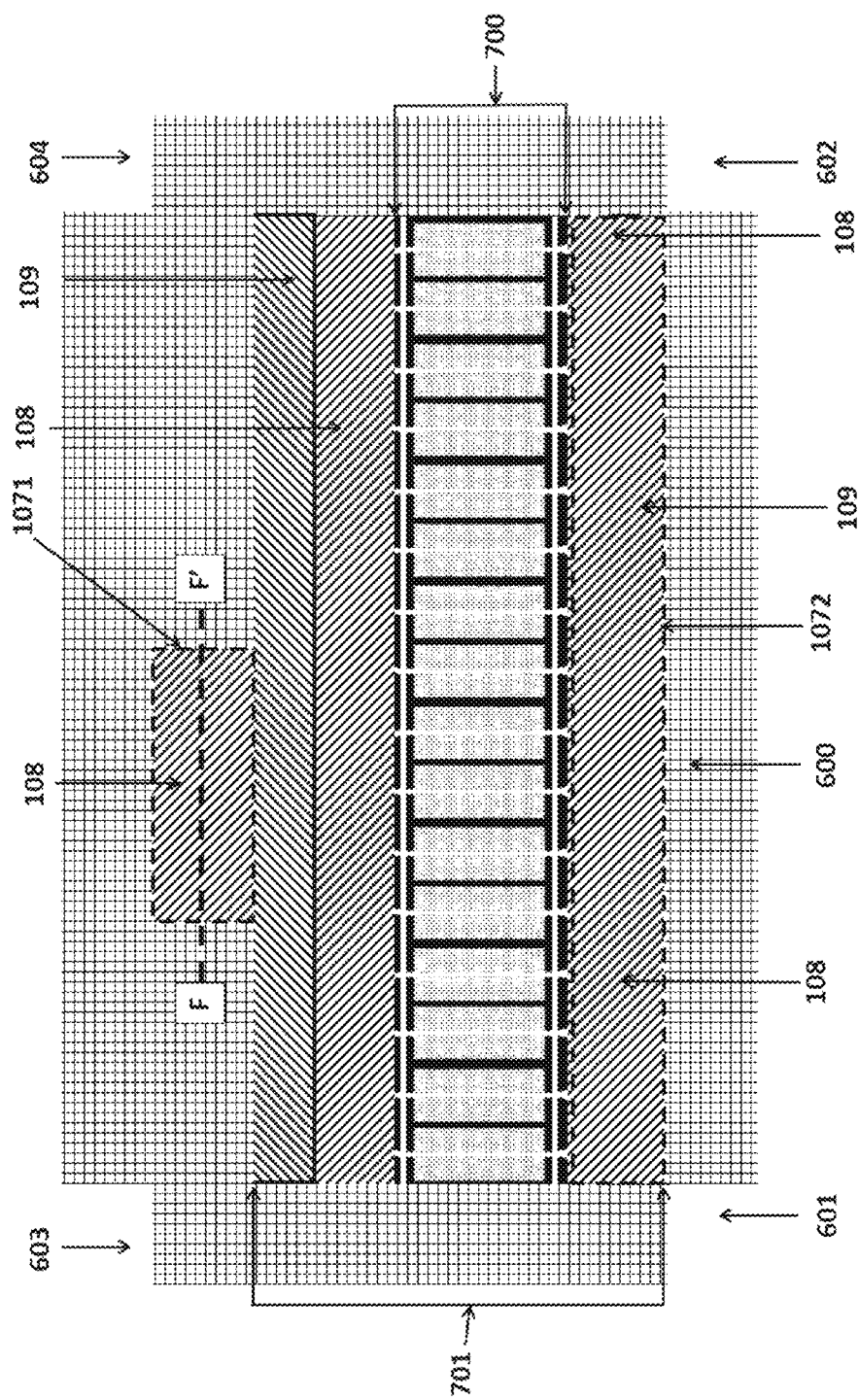

FIG. 18A is a top view of the arrayed device within an outer package in a second embodiment in which the light is incident and also exits the chip from the top. Light is incident on the input sub-wavelength grating coupler through a cover polymer overlayer. Light exits from the output sub-wavelength grating couplers through the cover polymer overlayer to the detector.

Figure 18B:
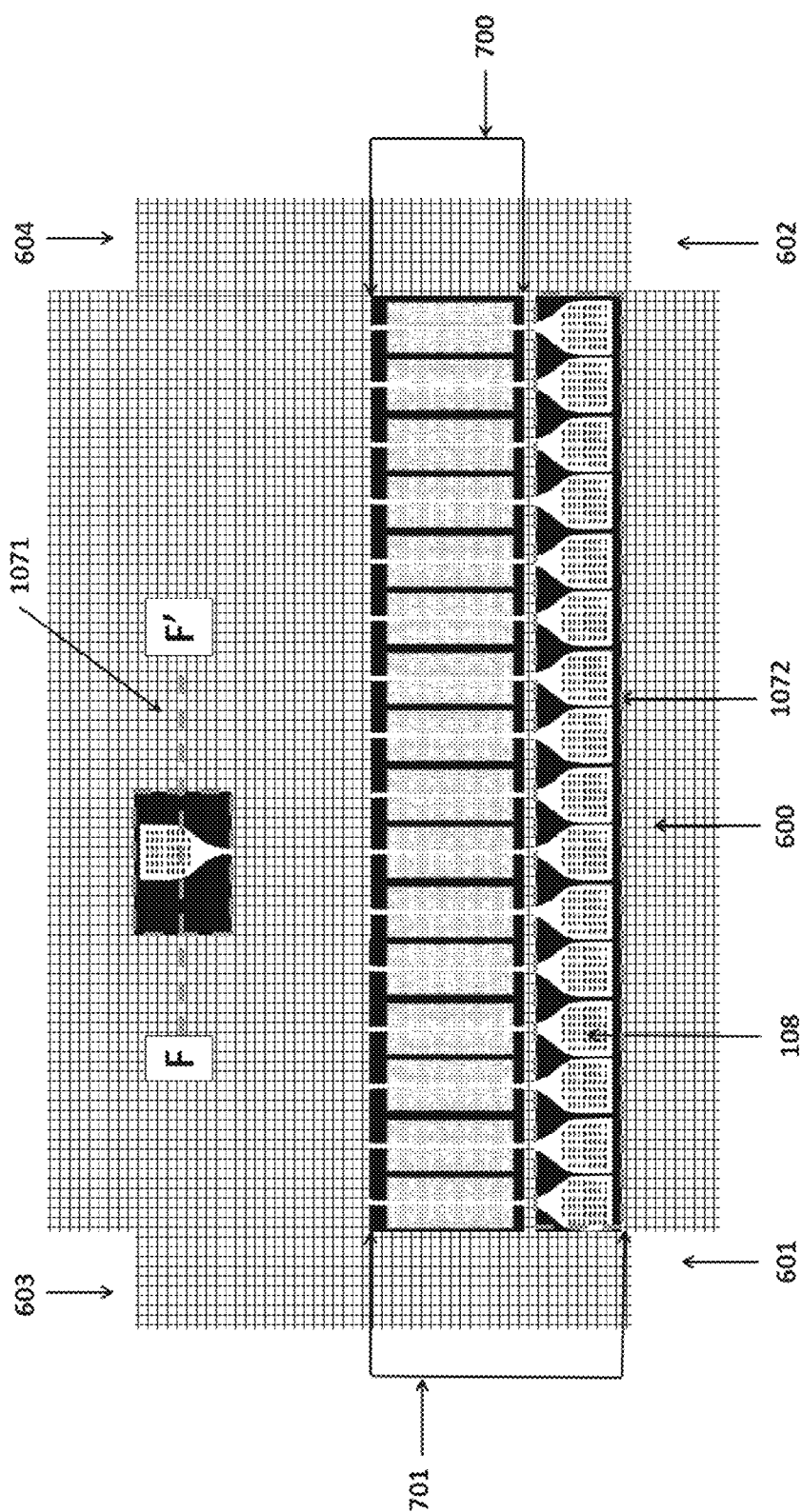

FIG. 18B is a top view of the arrayed device within an outer package in a second embodiment in which the light is incident and also exits the chip from the top. Light is incident on the input sub-wavelength grating coupler. Light exits from the output sub-wavelength grating couplers to the detector. In this case, the cover polymer and rigid dielectric are absent, and instead a PDMS microfluidic channel is bonded to the arrayed device.

Figure 19A:
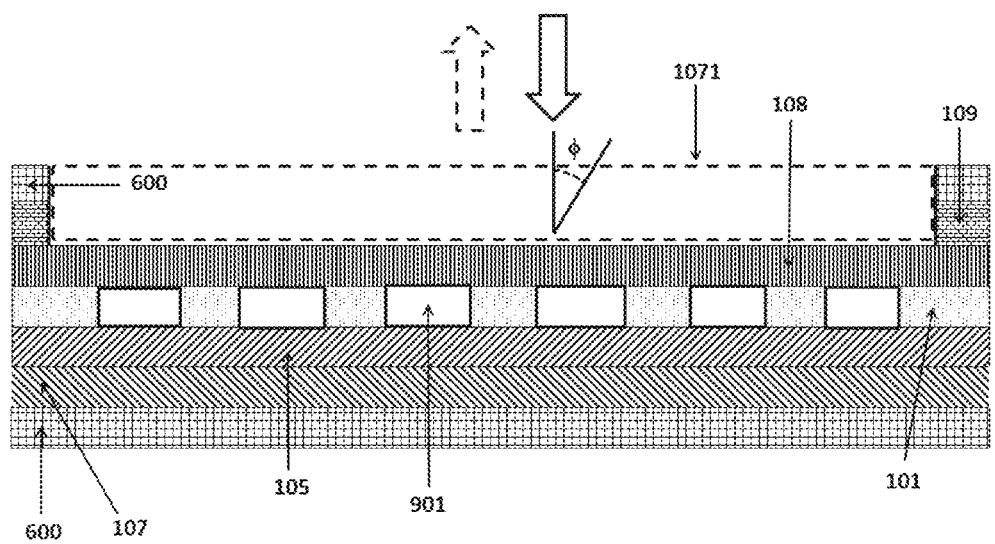

FIG. 19A is a cross-section view of the package with the chip inside along the plane F-F' in FIG. 18A for the case of the second embodiment where the light is incident from the top and is also collected from the top of the chip.

Figure 19B:
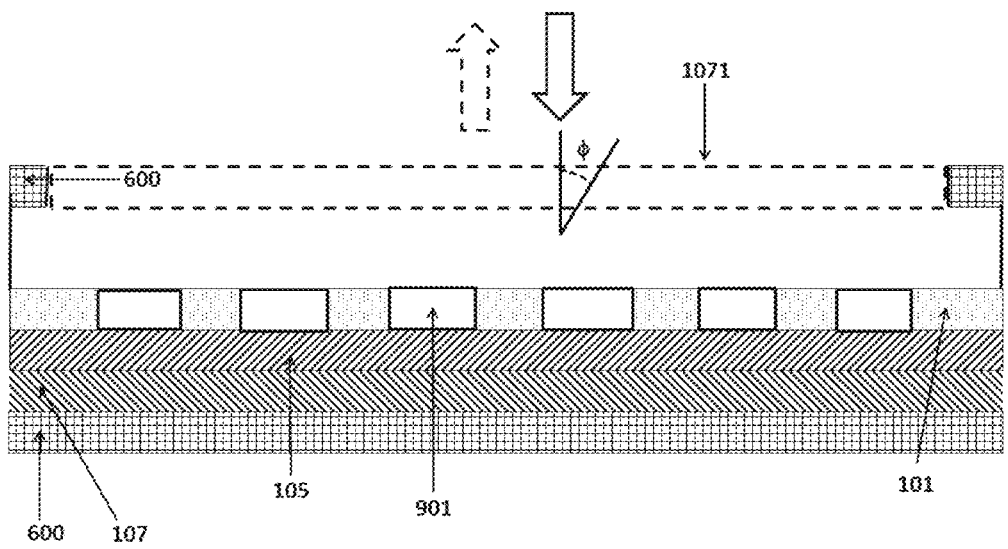

FIG. 19B is a cross-section view of the package with the chip inside along the plane F-F' in FIG. 18B for the case of the second embodiment where the light is incident from the top and is also collected from the top of the chip. In this case, the cover polymer and rigid dielectric are absent, and instead a PDMS microfluidic channel is bonded to the arrayed device.

Figure 20:
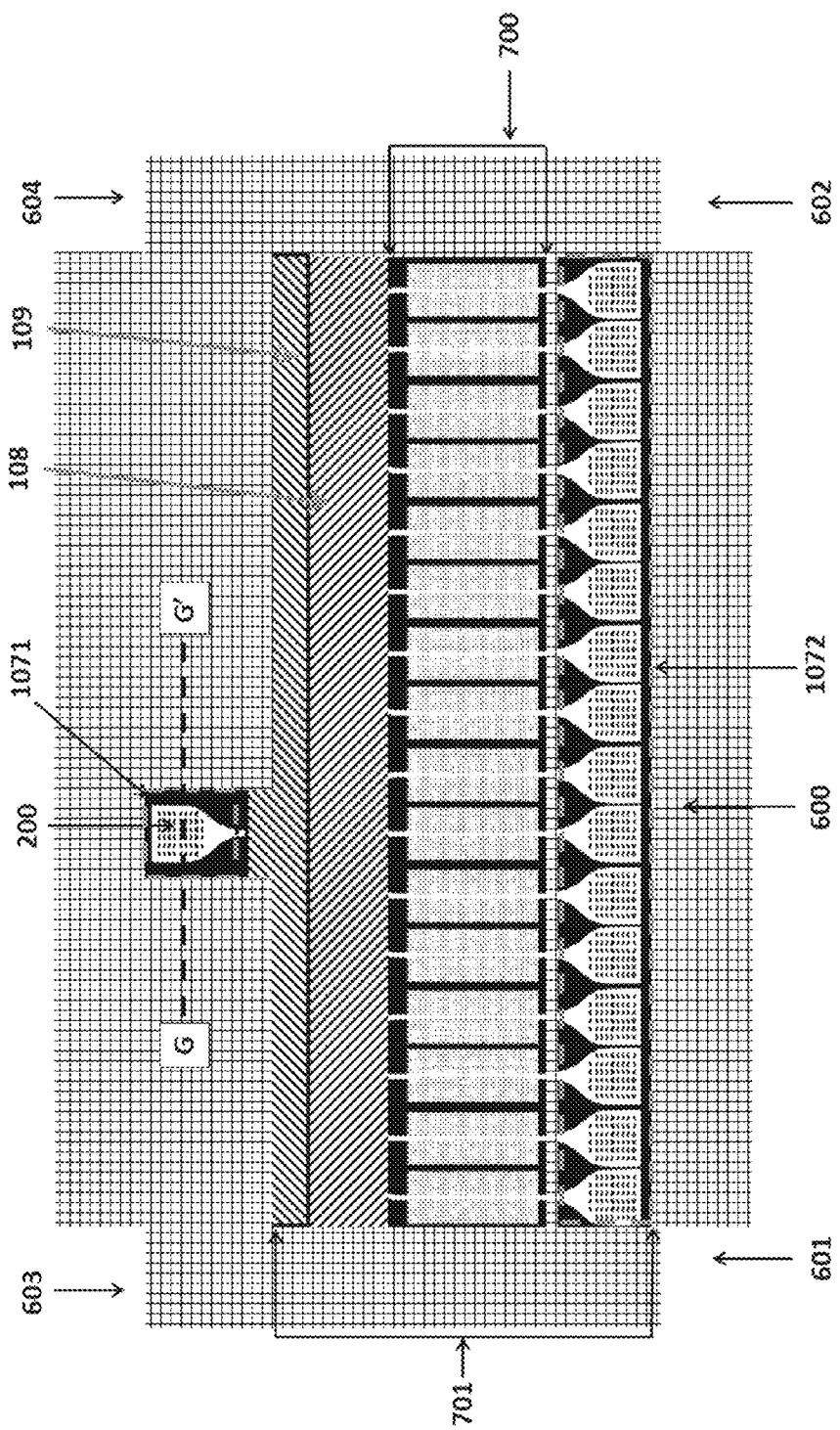

FIG. 20 is a top view of the arrayed device within an outer package in a third embodiment in which the light is incident and also exits the chip from the top. Light is incident directly on the input sub-wavelength grating coupler. Light exits directly from the output sub-wavelength grating couplers to the detector. The cover polymer and rigid dielectric layers exist in other areas over the chip as shown.

Figure 21:
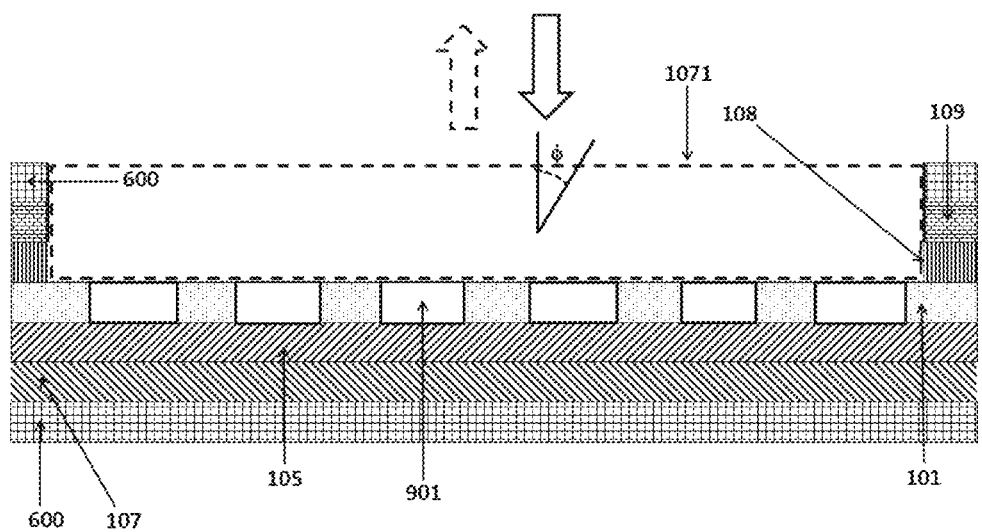

FIG. 21 is a cross-section view of the package with the chip inside along the plane G-G' in FIG. 20 for the case of the third embodiment where the light is incident from the top and is also collected from the top of the chip.

Figure 22:
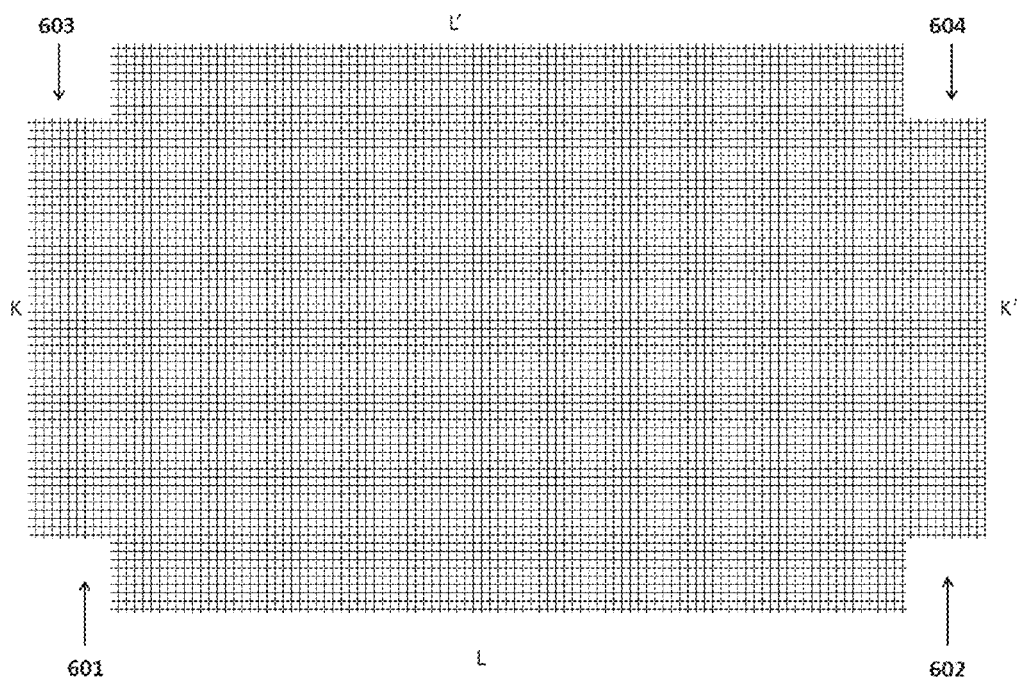

FIG. 22 is a view from the bottom of the package in the case of the second embodiment described by FIG. 18A, FIG. 18B, FIG. 19A, and FIG. 19B and the third embodiment described by FIG. 20 and FIG. 21.

Figure 23A:
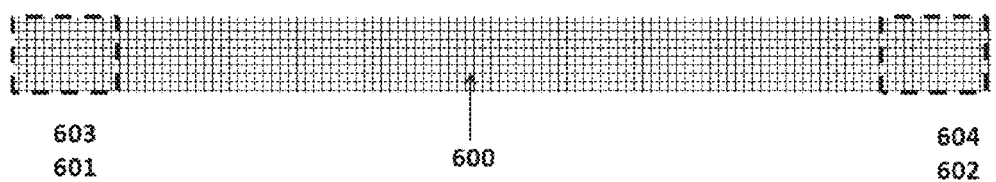
Figure 23B:
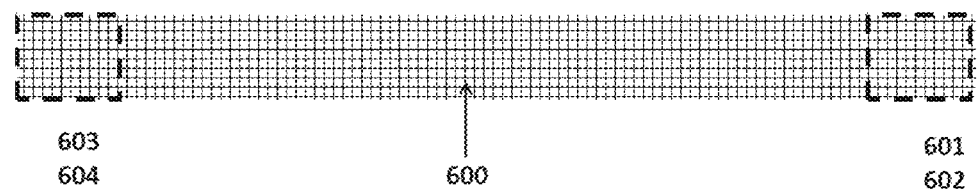

FIG. 23A is a view of the package from the sides of the package I or I' as denoted in FIG. 22. FIG. 23B is a view of the package from the sides of the package K or K' as denoted in FIG. 22.

FIG. 24A, FIG. 24B, FIG. 24C, and FIG. 24D illustrate typical transmission spectra from the 4 output arms of a 1×4 MMI with a photonic crystal waveguide coupled microcavity in each arm.

Figure 25:
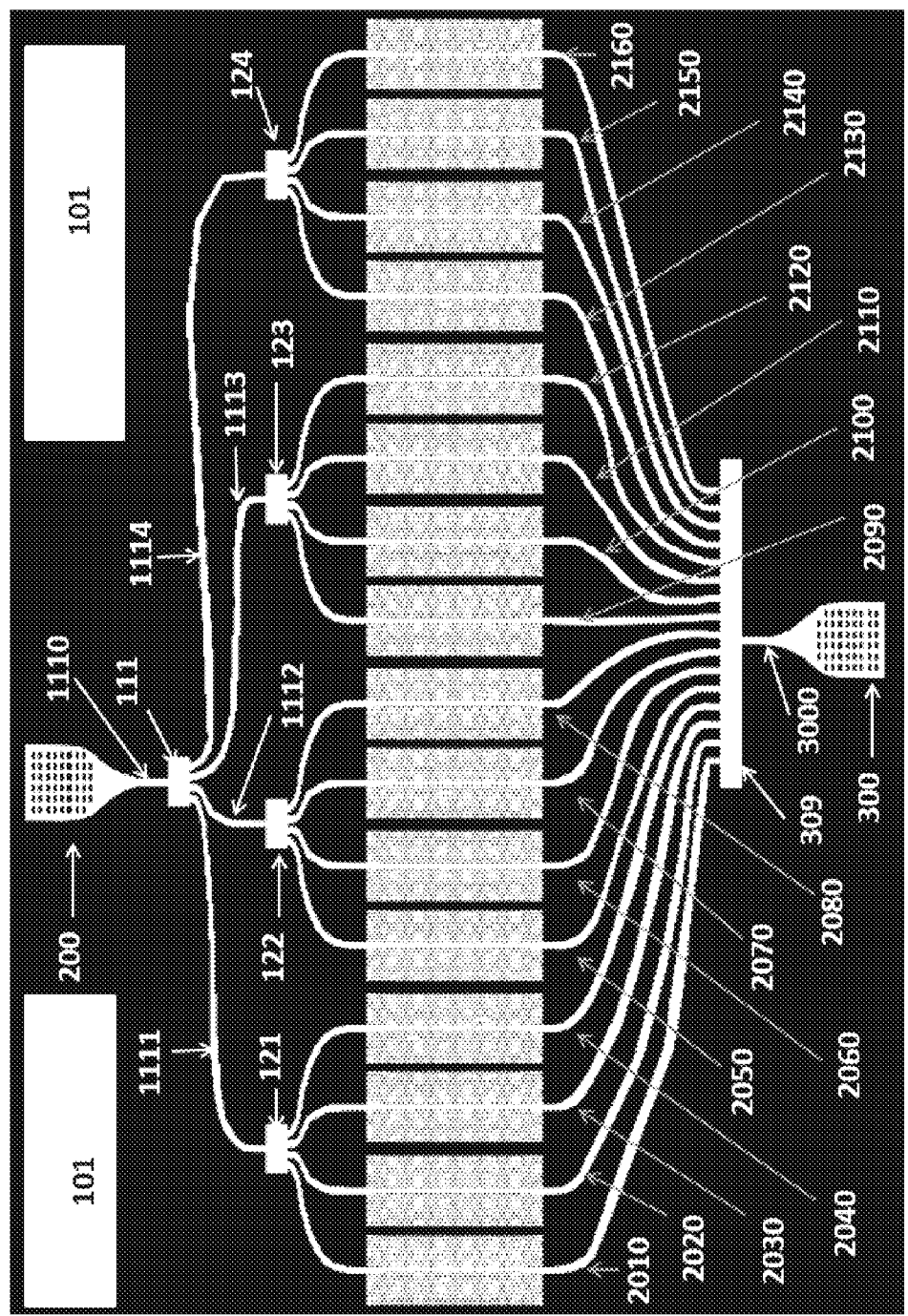

FIG. 25 illustrates one embodiment of the output waveguide configuration to output light using a single multimode interference power combiner.

Figure 26:
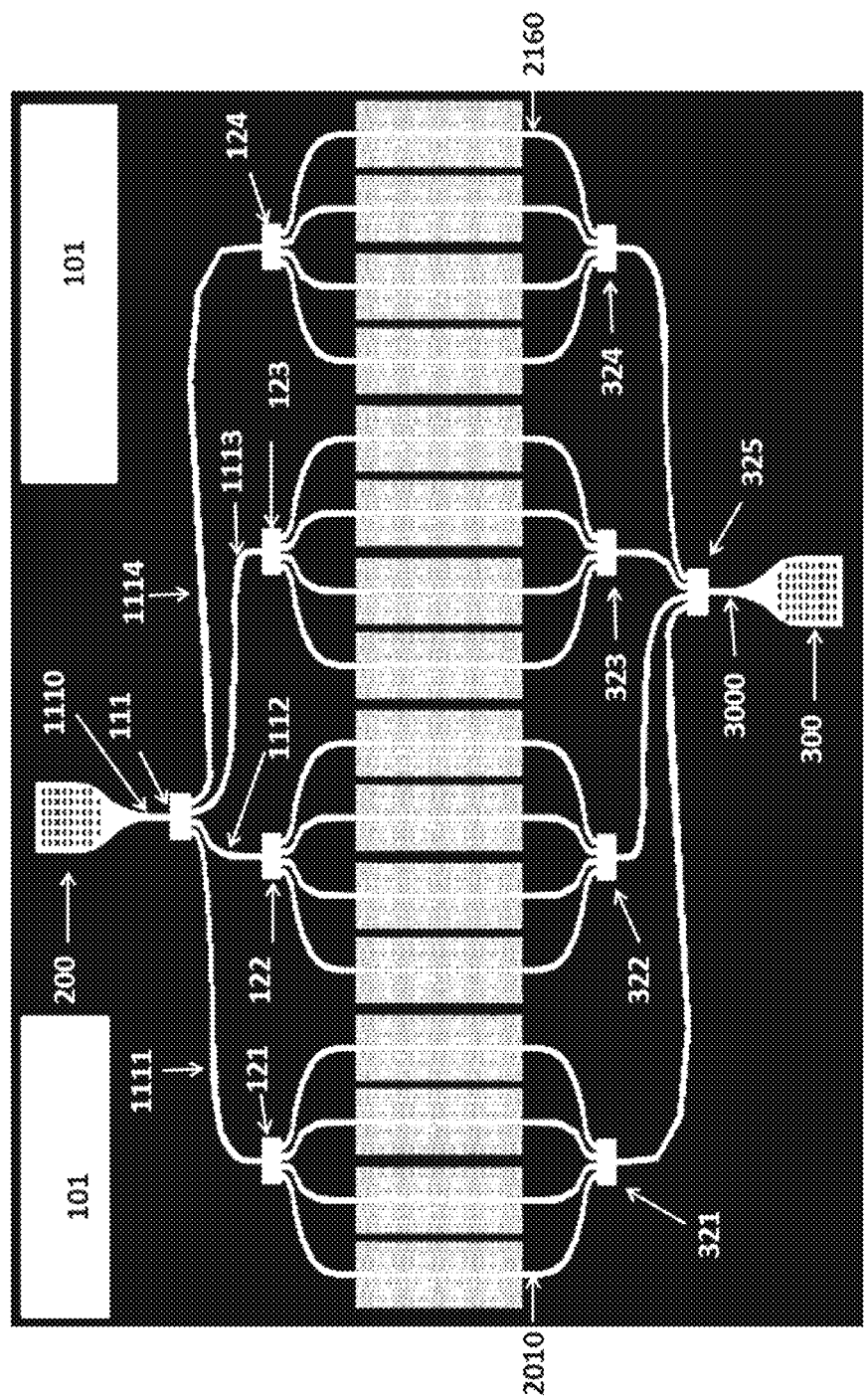

FIG. 26 illustrates one embodiment of the output waveguide configuration to output light using cascaded stages of multimode interference power combiners.

Figure 27:
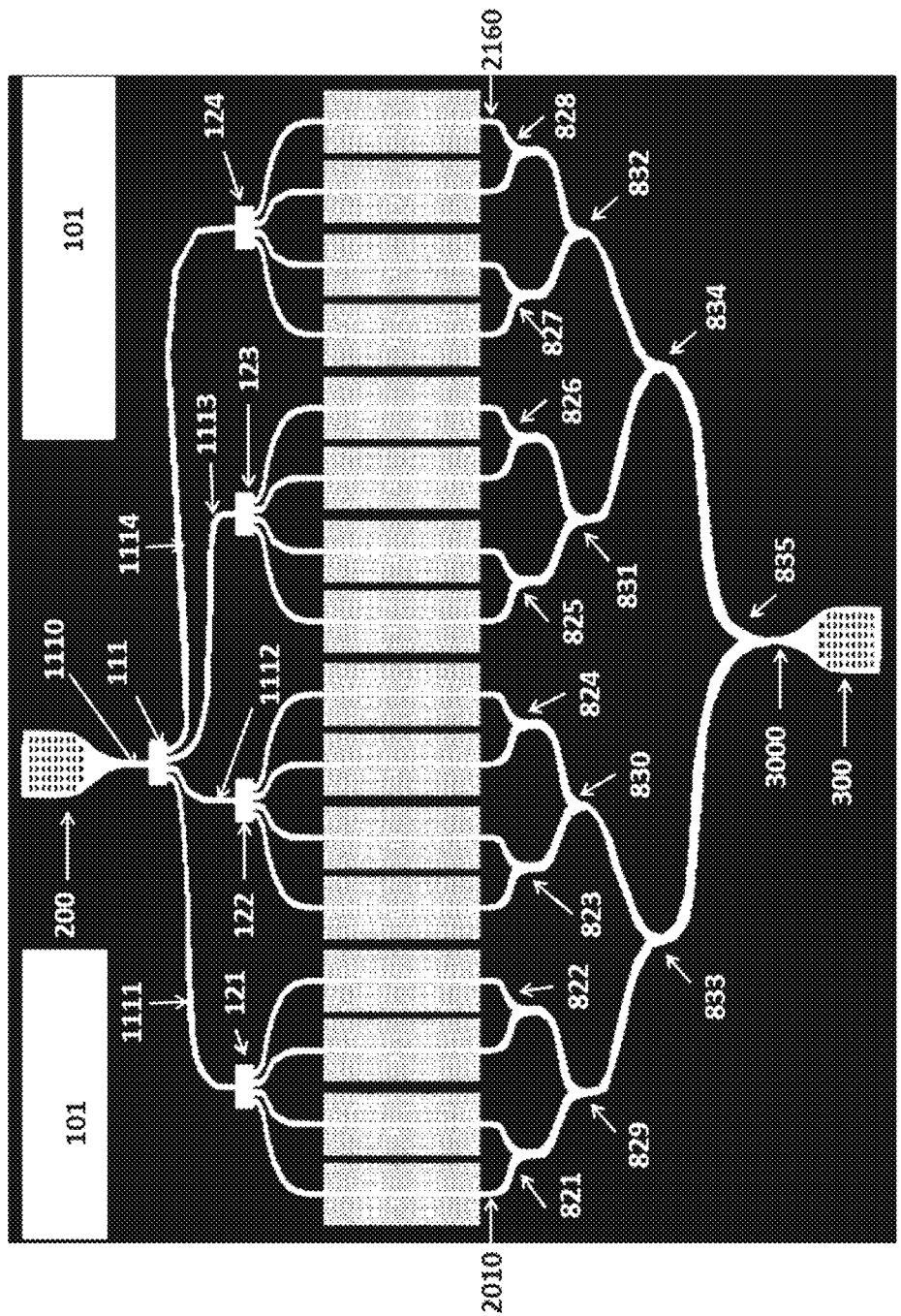

FIG. 27 illustrates one embodiment of the output waveguide configuration to output light using cascaded stages of Y-junction power combiners.

Figure 28A:
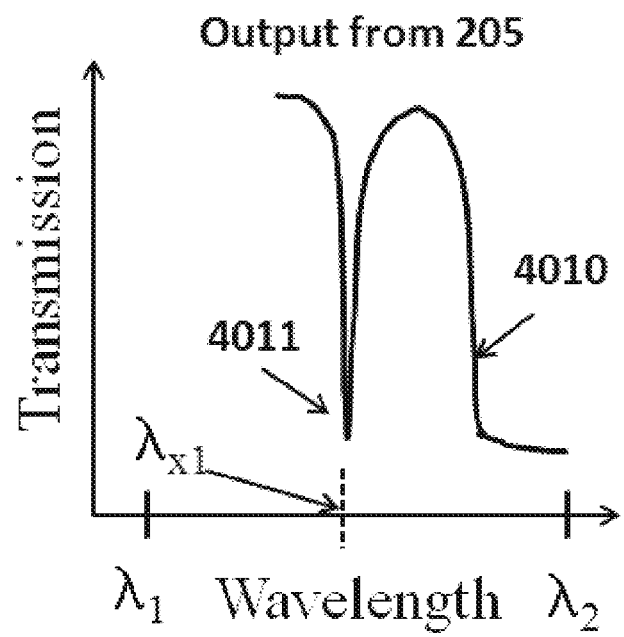
Figure 28B:
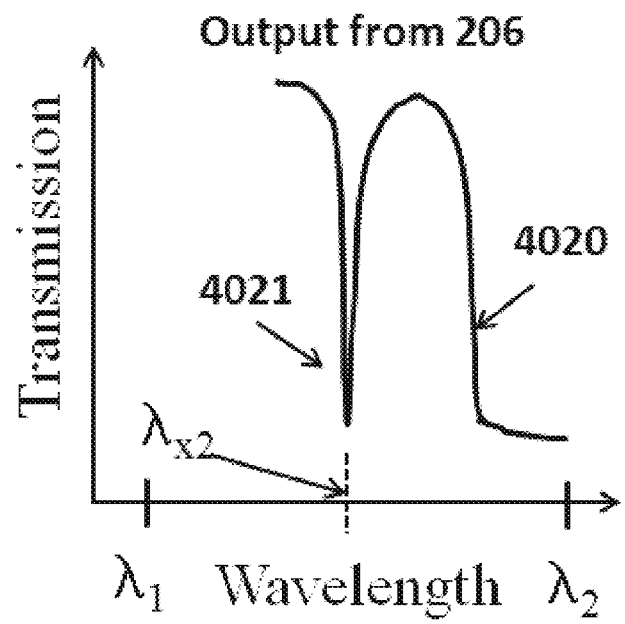
Figure 28C:
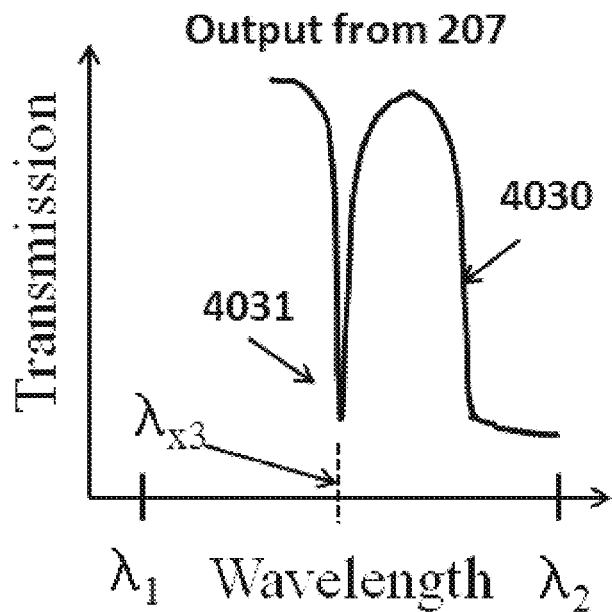
Figure 28D:
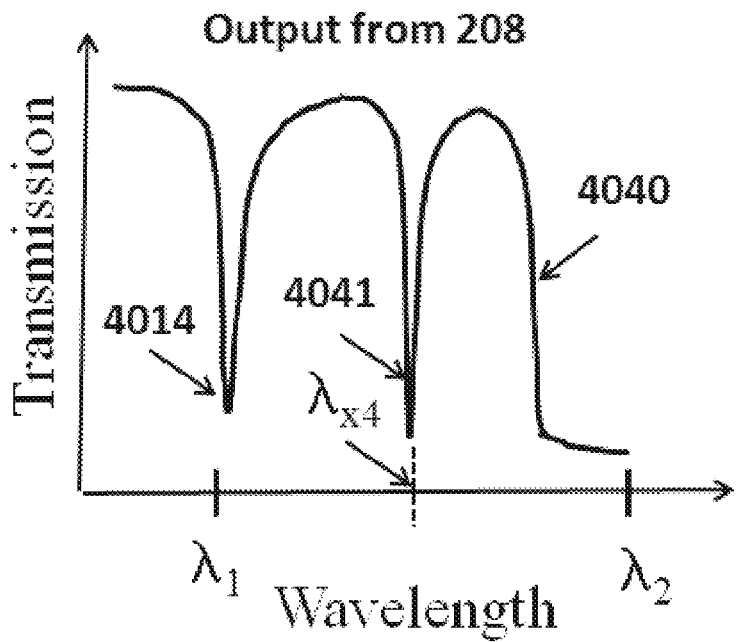
Figure 28E:
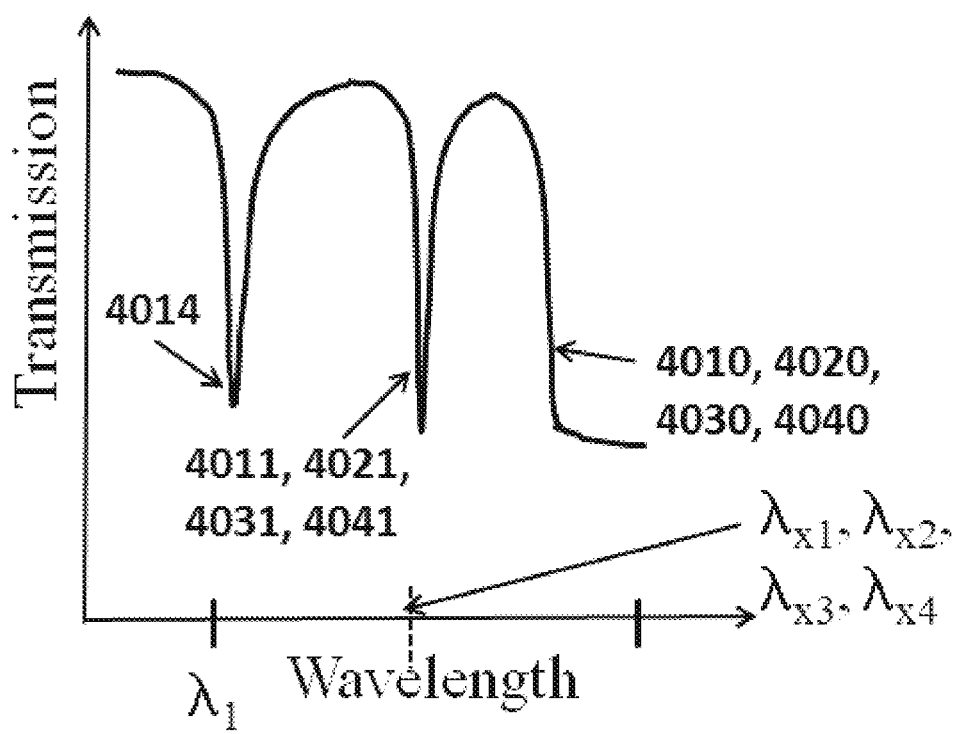

FIG. 28A, FIG. 28B, FIG. 28C, and FIG. 28D describe output optical transmission spectra observed at all output waveguides in FIG. 3A, when the photonic crystal patterns in each arm have the same lattice constant and FIG. 28E describes the situation if the individual transmission spectra from FIG. 28A, FIG. 28B, FIG. 28C, and FIG. 28D were combined into a single output channel.

Figure 29A:
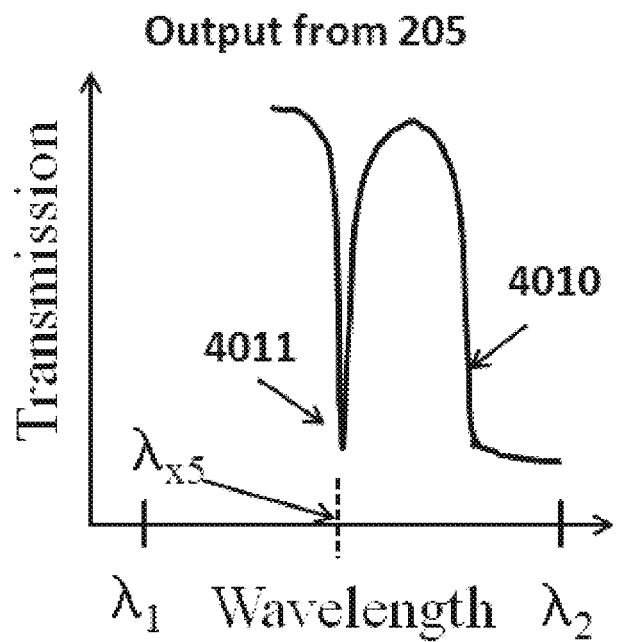
Figure 29B:
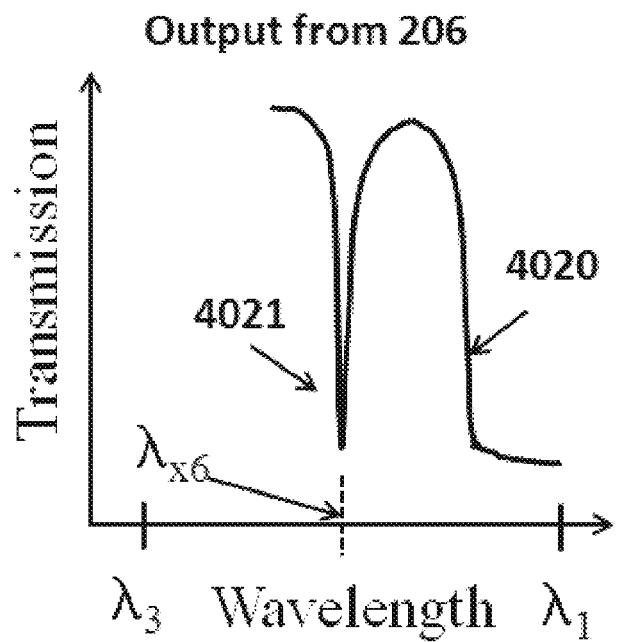
Figure 29C:
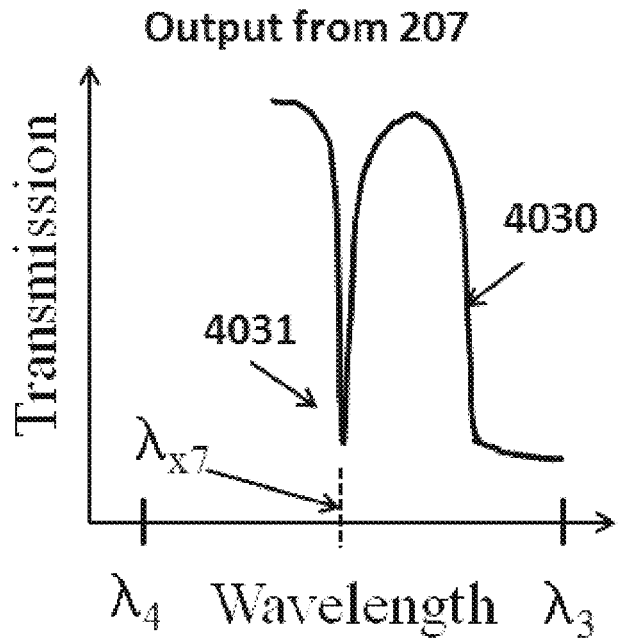
Figure 29D:
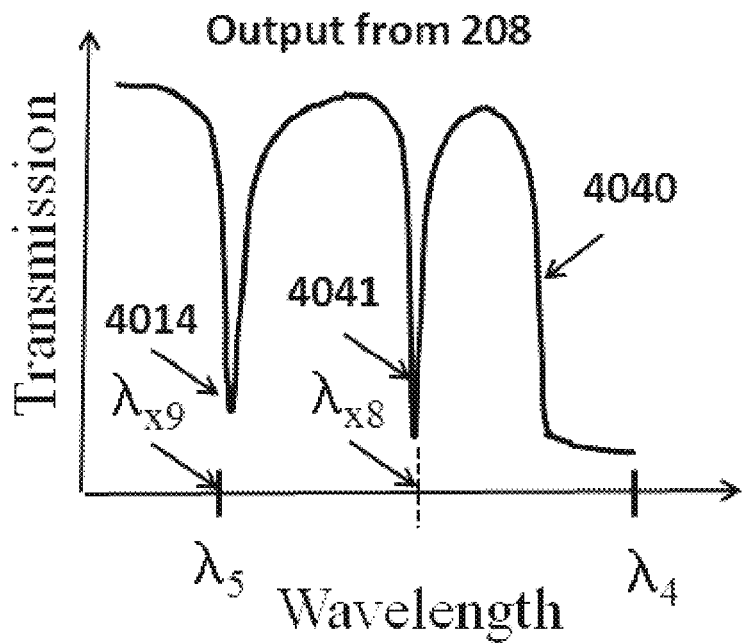
Figure 29E:
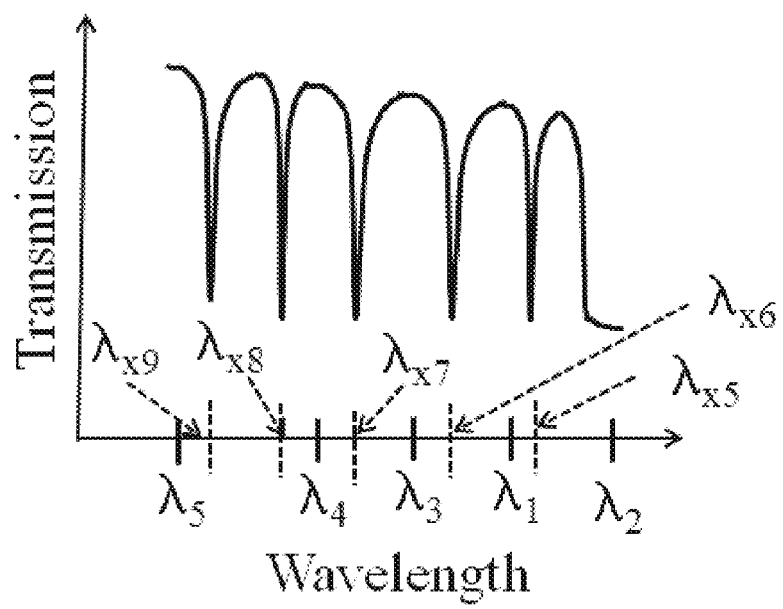

FIG. 29A, FIG. 29B, FIG. 29C, and FIG. 29D describe output optical transmission spectra observed at all output waveguides in FIG. 3A, when the photonic crystal patterns in each arm have different lattice constants and FIG. 29E describes the situation if the individual transmission spectra from FIG. 29A, FIG. 29B, FIG. 29C, and FIG. 29D were combined into a single output channel.

Figure 30:
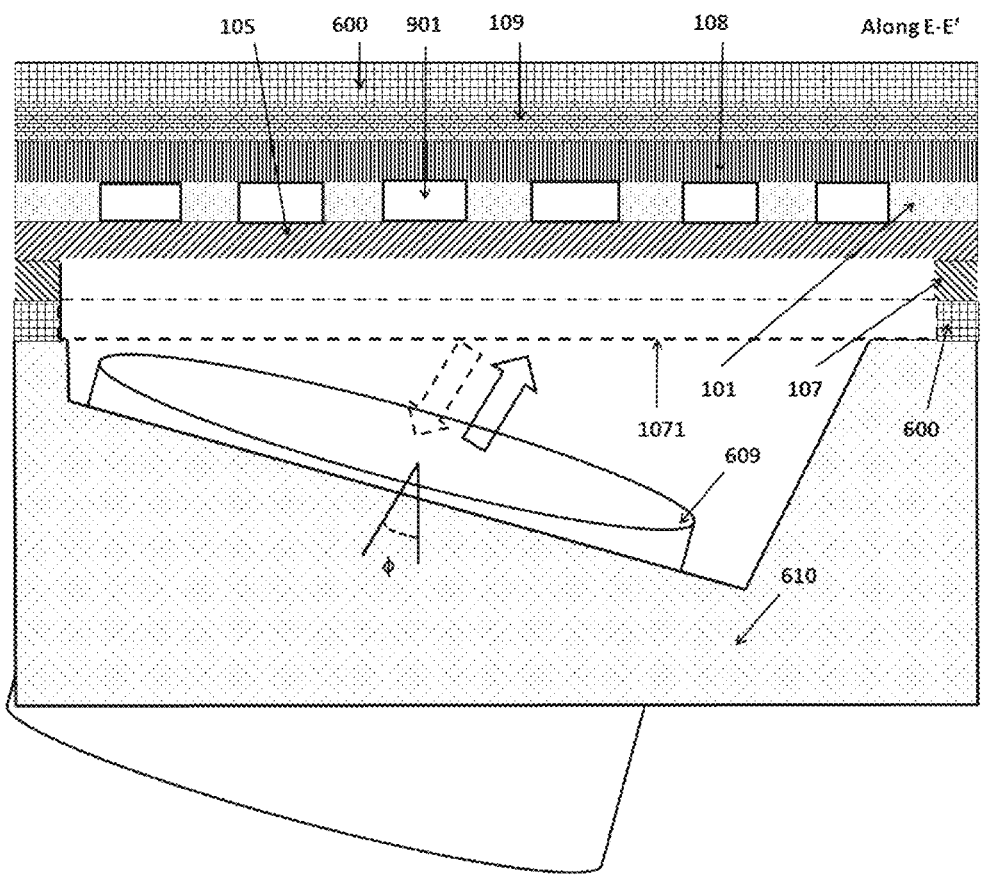

FIG. 30 illustrates the packaging of an external optical fiber with ultraviolet (UV)-cured epoxy to the packaged device.

Figure 31:
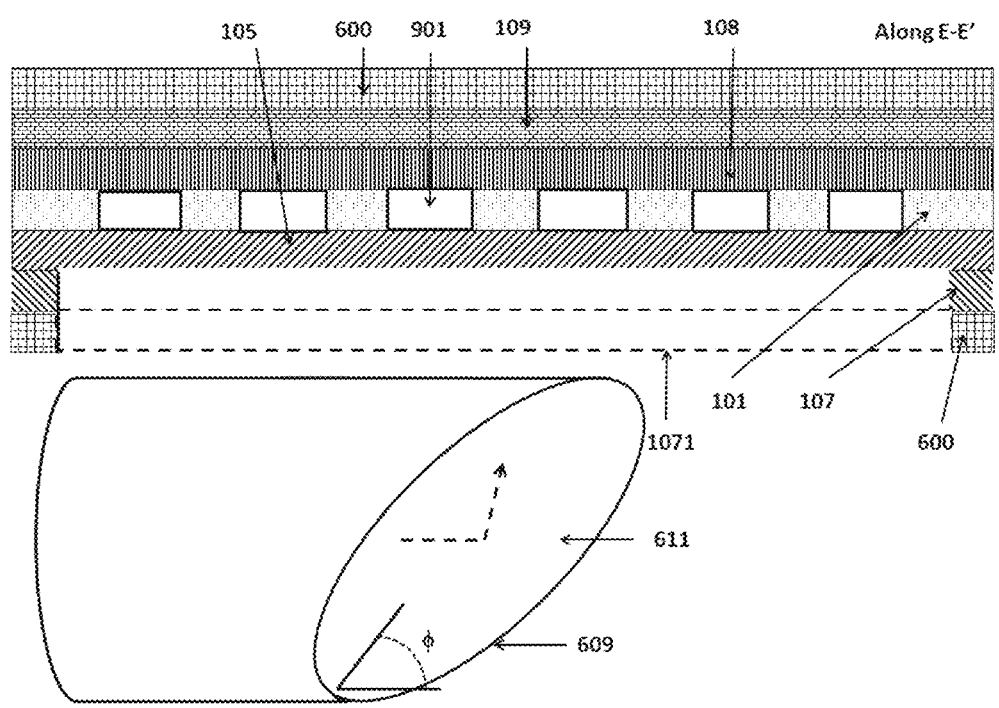

FIG. 31 illustrates the packaging of an external optical fiber with ultraviolet (UV)-cured epoxy to the packaged device when in addition the fiber facet is polished at an angle and coated with a reflecting material such as gold.

Figure 32:
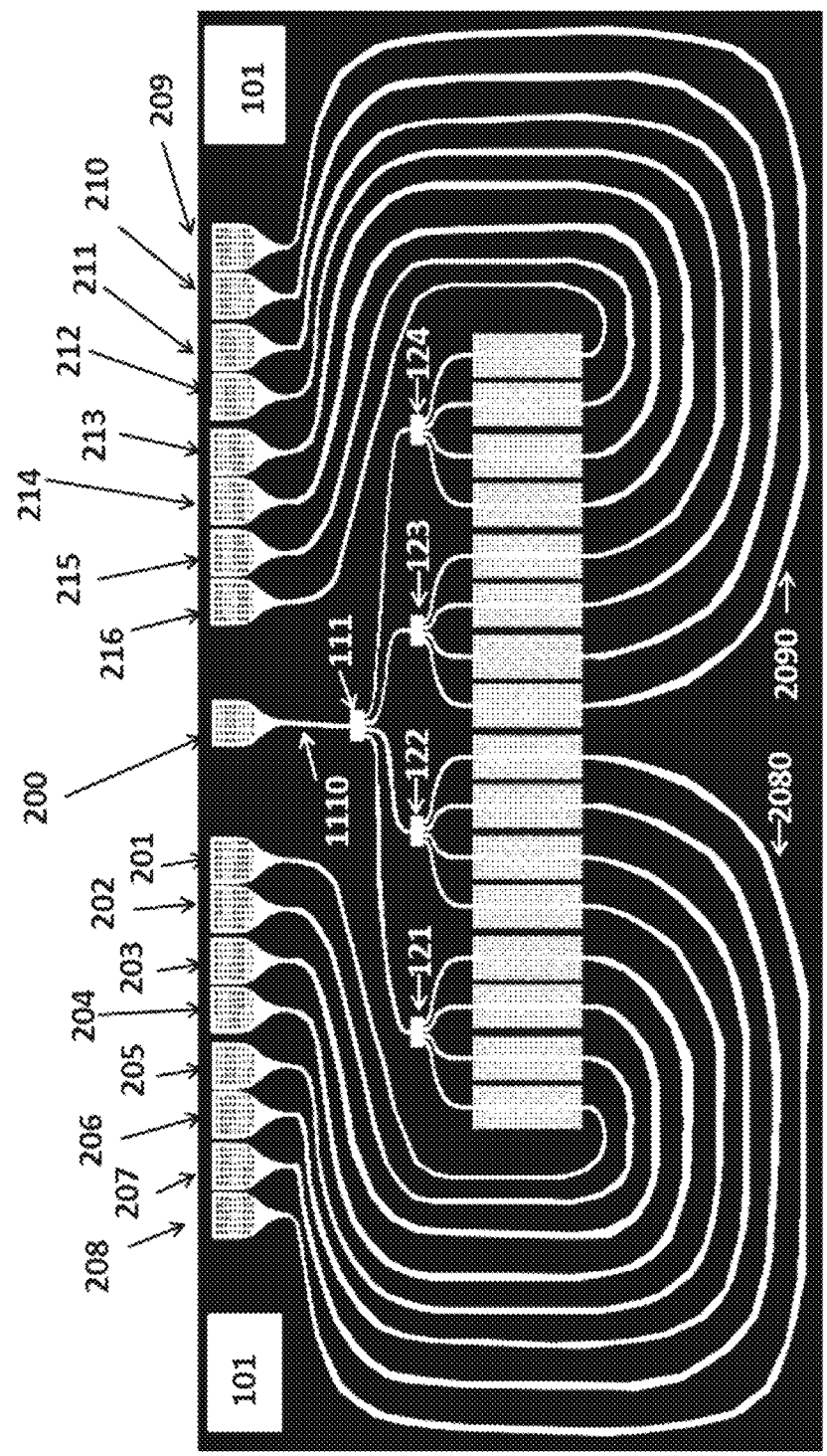

FIG. 32 illustrates one embodiment of the output waveguide configuration where the waveguides are bent by 180 degrees so that output sub-wavelength grating couplers are on the same side of the photonic crystal pattern as the input sub-wavelength grating coupler. One skilled in the art will note that crossing waveguides can be patterned to intersect primary waveguides at both the input and output, similar to FIG. 1A and FIG. 1B.

FIG. 33A, FIG. 33B, FIG. 33C, FIG. 33D, FIG. 33E, and FIG. 33F show representative photonic crystal microcavity configurations for wide dynamic range operation of photonic crystal sensors. FIG. 33G shows the resonance wavelength shift versus concentration observed for a set of four different photonic microcavity configurations which can be from FIG. 33A, FIG. 33B, FIG. 33C, FIG. 33D, FIG. 33E, or FIG. 33F. One skilled in the art will note that crossing waveguides can be patterned to intersect primary waveguides at both the input and output, similar to FIG. 1A and FIG. 1B.

V. DETAILED DESCRIPTION

Detailed Description of the Invention

In accordance with a preferred embodiment of the present invention, a device for multiplexing photonic crystal waveguide coupled microcavities comprises: a functional multimode interference power splitter that splits the input light equally into several output waveguides, a functional photonic crystal waveguide on each output arm of the MMI having a waveguide core along which light is guided, arrays of photonic crystal microcavities along the length of the photonic crystal waveguide each coated with a separate biomolecule specific to disease identification, an input and output photonic crystal impedance taper with gradually changed group index at the input and output end of the functional photonic crystal waveguide, which can bridge the refractive indices difference between conventional optical waveguides that form the output arms of the MMI and the functional photonic crystal waveguide. The sensor can be used to detect organic or inorganic substances such as proteins, DNA, RNA, small molecules, nucleic acids, virus, bacteria, cells, and genes, without requiring labels such as fluorescence or radiometry. Light (from a broadband source or LED) coupled into the MMI is split equally in the output arms of the MMI. On each output arm of the MMI, light couples into a photonic crystal waveguide that couples with the resonance of a photonic crystal microcavity and thereby drops the resonant wavelength in the microcavity, leading to a minimum in the transmission spectrum of the photonic crystal waveguide at the resonant wavelength. Transmission minima are observed for each resonant wavelength of the individual microcavities along the photonic crystal waveguide. The resonance wavelength shifts to longer wavelengths in response to the attachment of a material on the microcavity surface leading to the corresponding shift of the transmission minimum of that microcavity.

In another embodiment of the present invention, a device for multiplexing photonic crystal waveguide coupled microcavities comprises: a functional MMI that splits the input light equally into several output waveguides, a functional photonic crystal waveguide on each output arm of the MMI having a waveguide core along which light is guided, arrays of photonic crystal microcavities along the length of the photonic crystal waveguide each coated with a separate polymer or hydrogel specific to a unique environmental parameter, an input and output photonic crystal impedance taper with gradually changed group index at the input and output end of the functional photonic crystal waveguide, which can bridge the refractive indices difference between conventional optical waveguides and the functional photonic crystal waveguide. The sensor can be used to detect changes in temperature, pressure, humidity, molarity of solution, acidity or alkalinity (pH) of aqueous medium, ion concentration of solutions, trace gases in the atmosphere, pollutants in ground water that can be organic or inorganic, volatile and non-volatile, pesticides and thereof in a single optical transmission measurement. A unique polymer or hydrogel is chosen with maximum response to changes in each of the above parameters and a unique microcavity along the waveguide is coated with a unique polymer or hydrogel. The polymer may be an ion-sensitive electrode or optode for the detection of ions in solution. Light (from a broadband source or LED) coupled into the MMI is split equally in the output arms of the MMI. On each output arm of the MMI, light couples into a photonic crystal waveguide that couples with the resonance of a photonic crystal microcavity and thereby drops the resonant wavelength in the microcavity, leading to a minimum in the transmission spectrum of the photonic crystal waveguide at the resonant wavelength. Transmission minima are observed for each resonant wavelength of the individual microcavities along the photonic crystal waveguide, in the pristine condition. The resonance wavelength shifts to longer wavelengths in response to changes in ambient parameters listed above leading to the corresponding shift of the transmission minimum of that microcavity, the amount of transmission minimum shift determines the absolute change in ambient conditions in the vicinity of the microarray device.

Methods for fabricating photonic crystal structures are widely described in the literature. Sensor structures of the invention have higher sensitivity than previous structures due to the use of two-dimensional photonic crystal microcavities with resonances that have high quality factor together with the slow light effect of two-dimensional photonic crystal waveguides Ink-Jet printing is used for patterning of multiple biomolecules exclusively on photonic crystal microcavities that preserves biomolecule functionality in aqueous phase.

Detailed descriptions of the preferred embodiments are provided herein. It is to be understood, however, that the present invention may be embodied in various forms. Therefore, specific details disclosed herein are not to be interpreted as limiting, but rather as a basis for the claims and as representative basis for teaching one skilled in the art to employ the present invention in virtually any appropriately detailed system, structure or manner.

FIG. 1A presents a top view schematic drawing of a multiplexed photonic crystal waveguide device. It comprises functional MMI 111 with one input arm 1110 which is a ridge waveguide and 4 representative output arms 1111, 1112, 1113, and 1114 which are four ridge waveguides. On each output arm 1111, 1112, 1113, and 1114, the second stage of a functional MMI is made. One skilled in the art will note that the number of output arms, shown as four in the figure can actually be any number m=1, 2, 3, 4, 5 . . . M. A representative second stage MMI on the arm 1112 is denoted as 122. The MMI 122 has four primary waveguide output arms 1221, 1222, 1223, and 1224 which are four ridge waveguides. Elements 1221, 1222, 1223, and 1224 have been shown in detail in FIG. 2A to avoid cluttering in FIG. 1A. Only two MMI stages are shown here, but one skilled in the art will note that the number of cascaded MMI stages can be cascaded n times where n=1, 2 . . . N. Each output arm 1221, 1222, 1223, and 1224 is a ridge waveguide that terminates in functional photonic crystal patterned regions 21, 22, 23, and 24 respectively. The ridge waveguide arms 1221, 1222, 1223, and 1224, and similar such arms at the output of the last cascaded stage of the M×N MMI's are denoted as primary waveguides. Elements 21, 22, 23, and 24 have been shown in detail in FIG. 2A and FIG. 3A to avoid cluttering in FIG. 1A. The core of the photonic crystal patterned region 21 comprises a functional photonic crystal waveguide 12212, an input impedance taper 12211 between the input ridge waveguide 1221 and the photonic crystal waveguide 12212 and an output impedance taper 12213 between the output ridge waveguide 2050 and the photonic crystal waveguide 12212. Only one photonic crystal microcavity 12214 is shown arrayed along the length of the photonic crystal waveguide 12212 for clarity. Elements 12211, 12212, 12213, and 12214 have been shown in detail in FIG. 3A to avoid cluttering in FIG. 1A. In general, P photonic crystal microcavities can be arrayed along the length of the single photonic crystal waveguide 12212. For instance, two photonic crystal microcavities 12244 and 12245 are arrayed along the length of the functional photonic crystal waveguide 12242 in the photonic crystal patterned region 24. Elements 12241, 12242, 12243, 12244, and 12245 have been shown in detail in FIG. 3A to avoid cluttering in FIG. 1A. The photonic crystal patterned regions 21, 22, 23, and 24 include a number of column members 102 etched through or partially into the semiconductor slab 101. Within each photonic crystal patterned region, the waveguide core 141 is defined as the space between the centers of two column members adjacent to the region where the columns are absent. In one preferred embodiment, the column members 102 are arranged to form a periodic lattice with a lattice constant α. In some embodiments, the width of waveguide core 141 can range from 0.5 times sqrt(3) times the lattice constant or period α to 50 times sqrt(3) times the lattice constant or period α. In FIG. 3A, the photonic crystal microcavities are parallel to the photonic crystal waveguide and are placed 2 lattice periods away from the waveguide. The core is shown in detail in FIG. 4. Crossing waveguides 2001, comprising one or more ridge waveguides, substantially orthogonally intersect, in the plane of the slab, the primary waveguides prior to the photonic crystal patterned regions. Crossing waveguides 2002, comprising one or more ridge waveguides, substantially orthogonally intersect, in the plane of the slab, the ridge waveguides, in between the output sub-wavelength grating couplers and the photonic crystal patterned regions.

Light is coupled into the input arm 1110 of the MMI 111 via a sub-wavelength grating coupler 200. The output light from each output ridge waveguide, in one instance, from the output ridge waveguide 2050 is coupled out of the plane of the slab 101 by an output sub-wavelength grating coupler 205. Sub-wavelength grating couplers 201, 202, 203 . . . 216 couple light out from the output ridge waveguides 2010, 2020, 2030 . . . 2160 respectively out of the plane of the slab 101. The light output from the individual sub-wavelength grating couplers 201, 202, 203 . . . 216 can be detected by individual external detectors or individual external optical fibers, one each for each output sub-wavelength grating coupler 201, 202, 203 . . . 216. The light output from the all individual sub-wavelength grating couplers 201, 202, 203 . . . 216 can also be detected at the same time by a single individual external detector or a single external optical fibers.

All white structures in FIG. 1A, FIG. 1B, FIG. 1C, FIG. 1D, FIG. 1G, FIG. 1H, FIG. 1I, and FIG. 1J are part of the semiconductor slab 101 and all black areas are voids formed by etching the corresponding features as defined by the black areas, into the slab 101 either completely or partially through the slab. One skilled in the art will note that the voids that are formed and denoted by black areas result in a lower dielectric constant or refractive index in these void regions compared to the white structures and thus confine the propagating optical modes in the white areas. The black areas can thus be denoted as horizontal cladding.

Figure 1B:
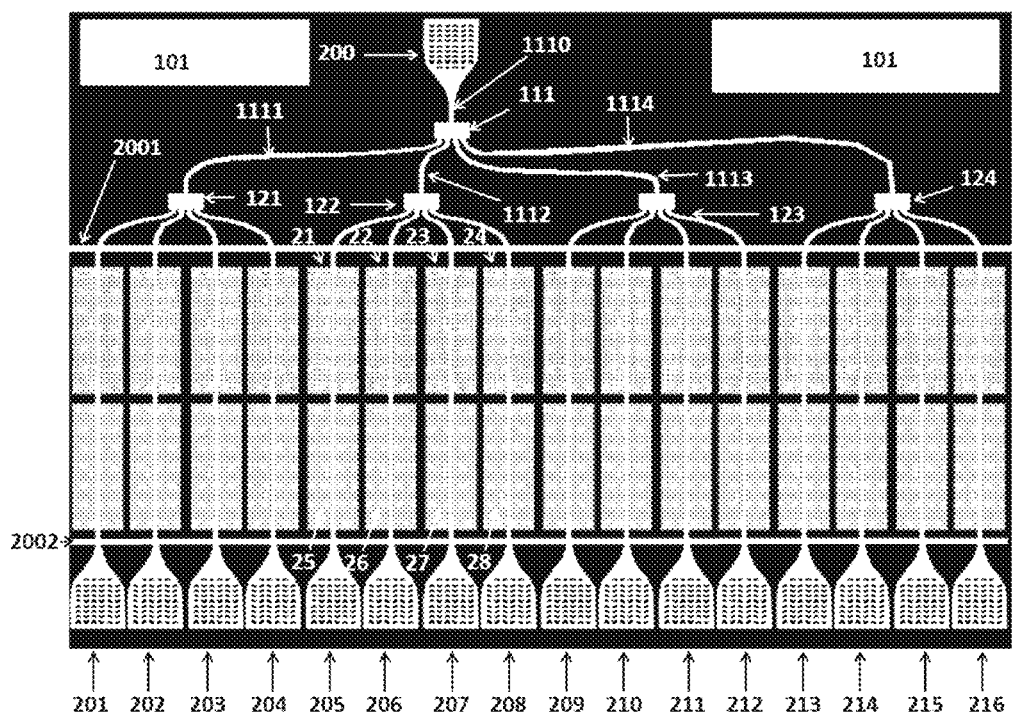

FIG. 1B is a schematic top view drawing showing one embodiment of the design of a microarray device based on a 1×N MMI, with a single input and N outputs. Each output arm can cascade into the input arm of a second stage MMI or in subsequent cascades to an $M^{th}$ stage MMI. The number of output ridge waveguides after the last stage MMI is thus M×N. On each output arm M×N, a photonic crystal waveguide is present and an array of P photonic crystal micro cavities are coupled to that photonic crystal waveguide. In FIG. 1B, N is chosen as 4 and M is chosen as 2. P is chosen as 1 or 2, where, in each photonic crystal waveguide that is connected in series, 1 or 2 photonic crystal microcavities are coupled to each photonic crystal waveguide. In FIG. 1B, 2 series cascaded stages of photonic crystal microcavity coupled waveguides are shown, Q=2. Functional photonic crystal patterned regions 21, 22, 23, and 24 are shown similar to FIG. 3A. In addition, a cascaded series of photonic crystal patterned regions 25, 26, 27, and 28 are shown. The photonic crystal patterned regions 25, 26, 27, and 28 column members 102 are etched through or partially into the semiconductor slab 101, similar to the photonic crystal patterned regions 21, 22, 23, and 24. The individual components comprising patterned regions 25, 26, 27, and 28 are the same as photonic crystal patterned regions 21, 22, 23, and 24. The lattice constant of the periodic triangular lattice of holes that defines 25, 26, 27, and 28 can be equal to, greater than, or less than the lattice constant of the patterned regions 21, 22, 23, and 24. Crossing waveguides 2001, comprising one or more ridge waveguides, substantially orthogonally intersect, in the plane of the slab, the primary waveguides prior to the photonic crystal patterned regions. Crossing waveguides 2002, comprising one or more ridge waveguides, substantially orthogonally intersect, in the plane of the slab, the ridge waveguides, in between the output sub-wavelength grating couplers and the photonic crystal patterned regions.

Figure 1C:
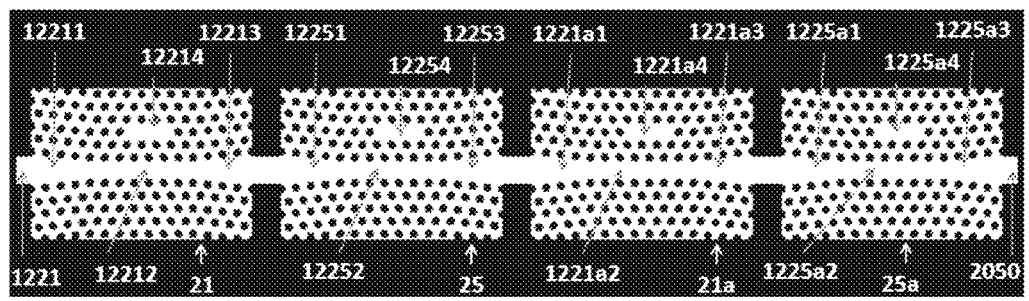
Figure 1D:
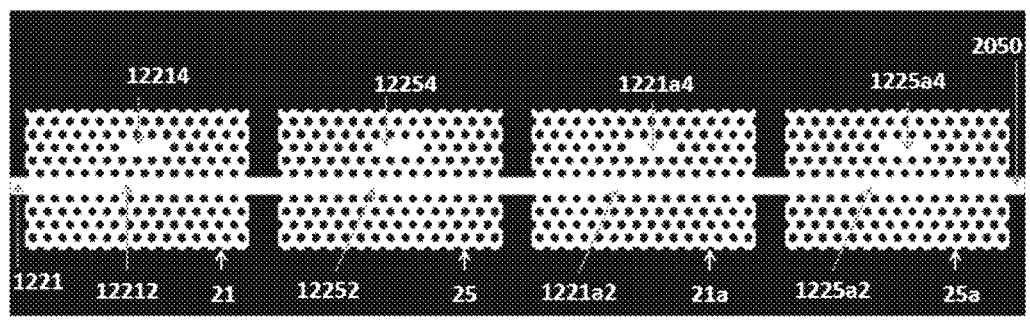

FIG. 1C and FIG. 1D show four series connected photonic crystal waveguides with coupled photonic crystal microcavities. Assume that the photonic crystal patterned regions, indicated by 21, 25, 21a, and 25a represent four photonic crystal waveguides along one arm, all in series, are inserted between the ridge waveguide 1221 at the output of the MMI 122, and the output waveguide 2050 (refer to FIG. 3A). A single photonic crystal microcavity 12214 (or 12254 or 1221a4 or 1225a4) is coupled to each single photonic crystal waveguide 12212 (or 12252 or 1221a2 or 1225a2) in series. In FIG. 1C, each photonic crystal waveguide cascaded in series has an input and output photonic crystal impedance taper with gradually changed group index at the input and output end of the functional photonic crystal waveguide, which can bridge the refractive indices difference between conventional optical waveguides and the functional photonic crystal waveguide. The input and output impedance tapers are created by gradually moving out the holes at the input and output of each photonic crystal waveguide section, away from the photonic crystal waveguide, normal to the photonic crystal waveguide in the plane of the slab over s=4 lattice periods. The input (and output) impedance tapers in the photonic crystal patterned regions 21 (and 25) are denoted by 12211 (and 12251) and 12213 (and 12253) respectively. Similarly, the input (and output) impedance tapers in the photonic crystal patterned regions 21a (and 25a) are denoted by 1221a1 (and 1225a1) and 1221a3 (and 1225a3) respectively. In FIG. 1D, a single photonic crystal microcavity 12214 (or 12254 or 1221a4 or 1225a4) is coupled to each single photonic crystal waveguide

Figure 1E:
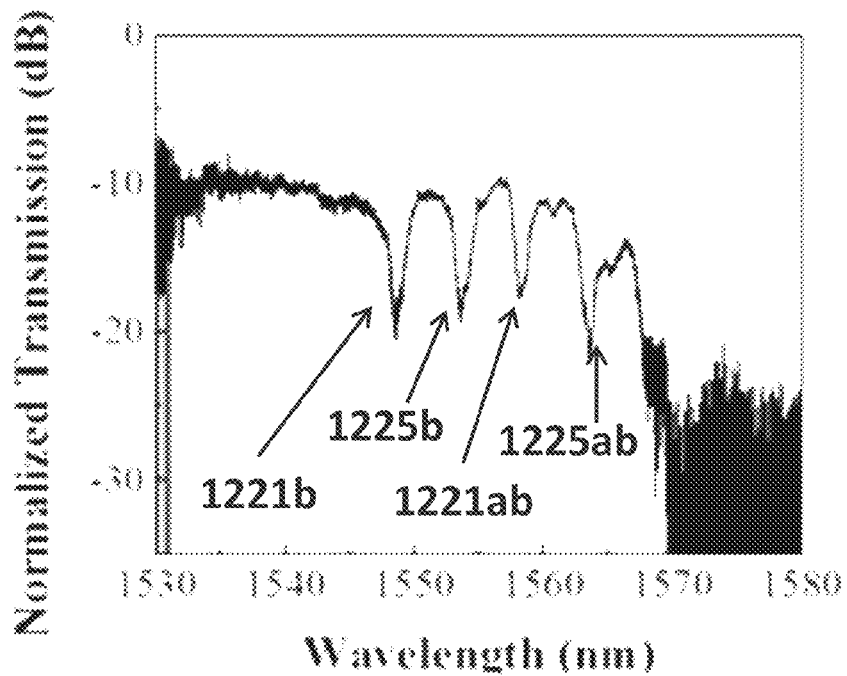
Figure 1F:
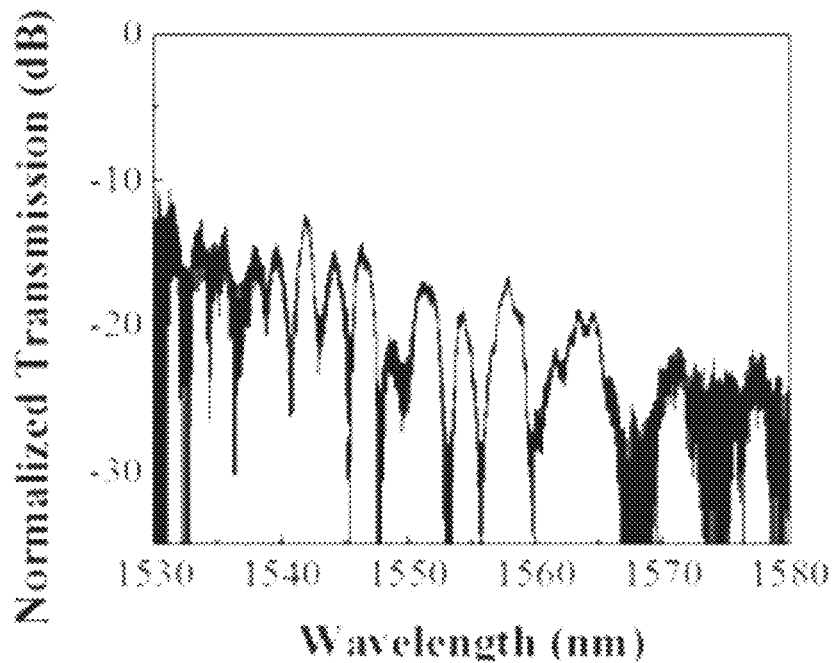
Figure 1G:
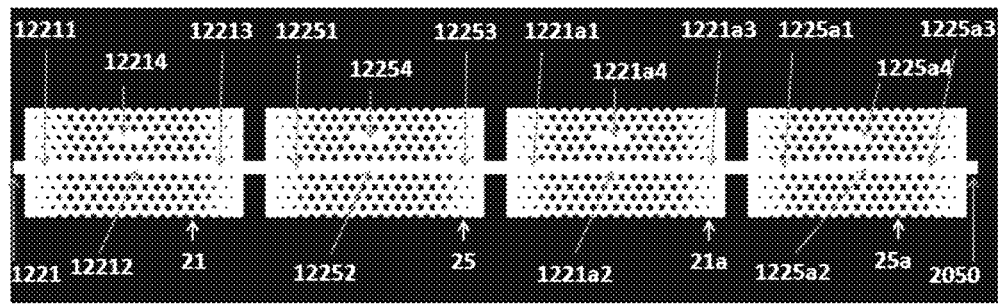
Figure 1H:
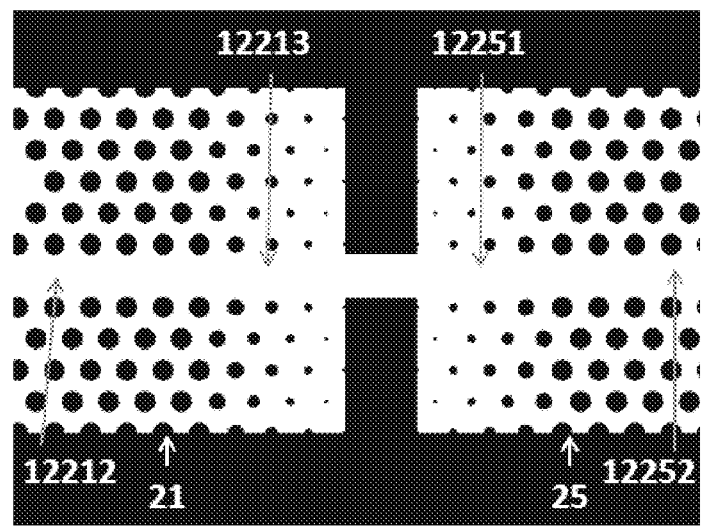
Figure 1I:
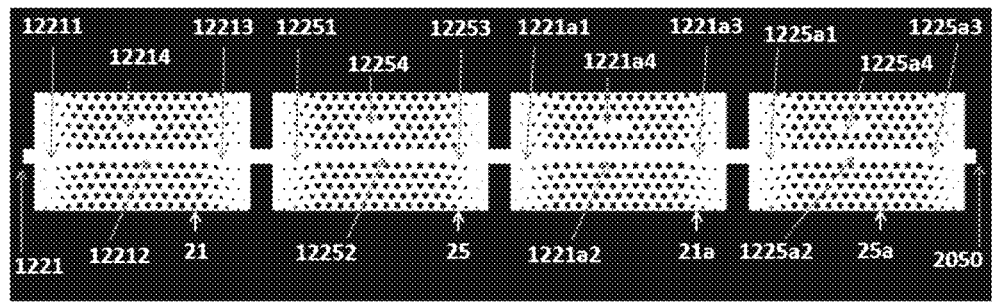
Figure 1J:
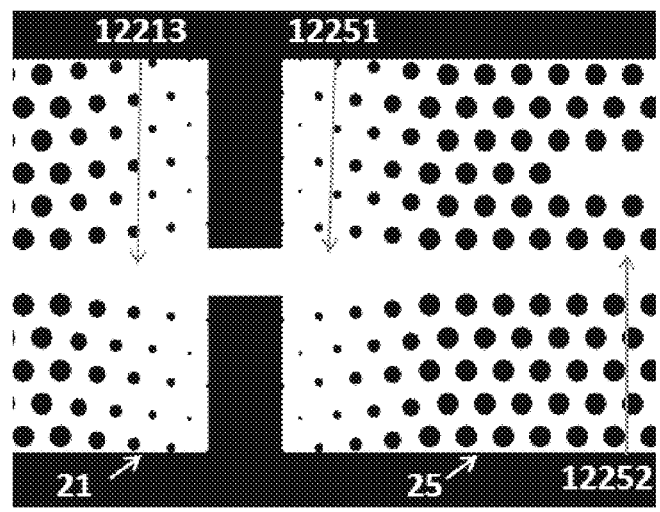

12212 (or 12252 or 1221*a*2 or 1225*a*2) in series. There are no input or output impedance taper at the input and output end of the functional photonic crystal waveguide 12212 (or 12252 or 1221*a*2 or 1225*a*2). The output transmission spectrum measured at the output subwavelength grating coupler for the device in FIG. 1C is shown in FIG. 1E. Four resonance wavelengths 1221*b*, 1225*b*, 1221*ab*, and 1225*ab* are distinctly observed. The output transmission spectrum measured at the output subwavelength grating coupler for the device in FIG. 1D is shown in FIG. 1F. In this case, the resonance wavelengths 1221*b*, 1225*b*, 1221*ab*, and 1225*ab* do exist, however, they are hidden under the large Fabry-Perot resonances due to large group index mismatch resulting from the absence of the impedance taper, at each of the photonic crystal waveguide and ridge waveguide boundaries. One skilled in the art will note that the device structure in FIG. 1C on one output arm 1221 of MMI 122 in FIG. 1A can be made on each of the 16 output arms (4 each resulting from the 4 MMIs 121, 122, 123, and 124 in FIG. 1A). By calculation, one can then obtain the resonance wavelength shift from 16 times 4=64 photonic crystal microcavities simultaneously at the same instant of time. Two other possible configurations for the group index variations that form the input and output impedance tapers are shown in FIG. 1G and FIG. 1H. In FIG. 1G, the diameter of the holes at the input and output impedance taper regions are gradually reduced from the photonic crystal waveguide section to the input (or output ends) of the photonic crystal patterned regions. A magnified view of the input and output impedance tapers of FIG. 1G is shown in FIG. 1H. In FIG. 1I, the diameter of the holes at the input and output impedance taper regions are also gradually reduced from the photonic crystal waveguide section to the input ends (and output ends) of the photonic crystal patterned regions. In addition, the holes at the input and output impedance taper regions are gradually moved out at the input and output of each photonic crystal waveguide section, away from the photonic crystal waveguide section, normal to the photonic crystal waveguide in the plane of the slab over s=4 lattice periods. A magnified view of the input and output impedance tapers of FIG. 1I is shown in FIG. 1J. As mentioned previously, the number of rows of air holes that may be shifted away from the photonic crystal waveguide, normal to the photonic crystal waveguide in the plane of the slab, S, can vary from 1 to 32.

The group index of a ridge waveguide (in silicon) is approximately 3. However, the group index in the photonic crystal waveguide guiding light in the slow light regime can be as high as 100. Such a group index mismatch leads to Fresnel reflection losses at the interface between the ridge waveguide and the photonic crystal waveguide. At the input and output ends of the photonic crystal waveguide, by reducing the diameter of the holes (FIG. 1G), or by moving the holes away from the photonic crystal waveguide, normal to the photonic crystal waveguide in the plane of the slab (FIG. 1C), or a combination of both (FIG. 1I), the effective group index is lowered at the interface between the ridge waveguide and the photonic crystal waveguide. Using an adiabatic/gradual change of the diameter of the holes adjacent to the photonic crystal waveguide, and/or an adiabatic/gradual change in the width of the photonic crystal waveguide at the input and output ends, also called the input impedance taper and output impedance taper respectively, the group index is gradually changed from low group index at the ridge waveguide to high group index at the photonic crystal waveguide, in the impedance taper sections, and thus reflection losses are minimized.

FIG. 2A is an enlarged top view of the input section in FIG. 1A and FIG. 1B showing the first stage MMI 111 and one of the four second stage MMIs 122. The functional MMI 111 has one input arm 1110 and 4 output arms 1111, 1112, 1113, and 1114 which are four ridge waveguides. One skilled in the art will note that the number of output arms, shown as four in the figure can actually be any number m=1, 2, 3, 4, 5 . . . M. The output ridge waveguide 1112 of the first stage MMI 111 forms the input to the second stage MMI 122. The MMI 122 has four output arms 1221, 1222, 1223, and 1224 which are four ridge waveguides. Each ridge waveguide 1221, 1222, 1223, and 1224 terminates in functional photonic crystal patterned regions 21, 22, 23, and 24 respectively. Crossing waveguides 2001, comprising one or more ridge waveguides, substantially orthogonally intersect, in the plane of the slab, the primary waveguides prior to the photonic crystal patterned regions. A magnified view of the intersection region H is next shown in FIG. 2B, FIG. 2C, and FIG. 2D. Similar to FIG. 1A and FIG. 1B, all white structures in FIG. 2A, FIG. 2B, FIG. 2C, FIG. 2D, and FIG. 2E are part of the semiconductor slab 101 and all black areas are voids formed by etching the corresponding features as defined by the black areas, into the slab 101 either completely or partially through the slab.

FIG. 2B is a magnified view of the intersection region H of crossing waveguides 2001 and the primary waveguide, in this instance 1221. In this case, 2001 comprises just one waveguide, 200101, that substantially orthogonally cuts across the primary waveguide 1221. In the intersection region H, the primary waveguide 1221 tapers at the input of the intersection region H to a larger width denoted by 122101, next has a larger width as denoted by 122103, and finally tapers back denoted by 122102 at the output of the intersection region H, to the width of 1221 at the input of the intersection region H. One skilled in the art will realize that 1221*a* at the output of the intersection region H denotes the continuation of the primary waveguide 1221, at the input of the intersection region H, after crossing waveguides 2001. A magnified view of the intersection region H1 is shown in FIG. 2E.

FIG. 2C is a magnified view of the intersection region H of crossing waveguides 2001 and the primary waveguide, in this instance 1221. In this case, 2001 comprises five waveguides, 200101, 200102, 200103, 200104, and 200105, that substantially orthogonally cut across the primary waveguide 1221. In the intersection region H, the primary waveguide 1221 tapers at the input of the intersection region H to a larger width denoted by 122101, next it has a larger width as denoted by 122103, and finally tapers back denoted by 122102 after crossing the five crossing waveguides of 2001, to the width of 1221 at the input of the intersection region H. One skilled in the art will realize that 1221*a* at the output of the intersection region with the crossing waveguides denotes the continuation of the primary waveguide 1221, at the input of the intersection region H. A magnified view of one of the intersection regions H1 is shown in FIG. 2E. The other intersection regions in FIG. 2C between the primary waveguide and 200102, 200103, 200104, and 200105 are the same as illustrated in FIG. 2E.

FIG. 2D is a magnified view of the intersection region H of crossing waveguides 2001 and the primary waveguide, in this instance 1221. In this case, 2001 comprises ten waveguides, 200101, 200102, 200103, 200104, 200105, 200106, 200107, 200108, 200109, and 200110, that substantially orthogonally cut across the primary waveguide 1221. In the intersection region H, the primary waveguide 1221 tapers at the input of the intersection region H to a larger width denoted by 122101, next has a larger width as denoted by 122103, and finally tapers back denoted by 122102 after crossing the ten crossing waveguides of 2001 at the output of the intersection region H, to the width of 1221 at the input of the intersection region H.

One skilled in the art will realize that 1221*a* at the output of the intersection region with the crossing waveguides denotes the continuation of the primary waveguide 1221, at the input of the intersection region H. A magnified view of one of the intersection regions H1 is shown in FIG. 2E. The other intersection regions in FIG. 2D between the primary waveguide and 200102, 200103, 200104, 200105, 200106, 200107, 200108, 200109, and 200110 and the primary waveguide are the same as illustrated in FIG. 2E.

FIG. 2E is a magnified view of the intersection region H1 of FIG. 2B, FIG. 2C, and FIG. 2D. A sub-wavelength nano structure, comprising tooth like structures 20011*a* in the slab separated by trenches is made on both the width modified primary waveguide 122103 and the crossing waveguide 200101. Such tooth like structures, 20011*a*, exist in each intersection of the other crossing waveguides with the primary waveguide.

While FIG. 2B, FIG. 2C, FIG. 2D and FIG. 2E have been shown prior to the photonic crystal patterned region, one skilled in the art will realize that the same design, of the crossing waveguide 2002 comprising one or more waveguides intersecting the waveguides 2050, 2060, 2070, and 2080 in FIG. 3A and all similar waveguides prior to the output sub-wavelength grating coupler may be utilized. One skilled in the art will also realize that such crossing waveguide architecture may exist in any optical waveguide, for any integrated optical device on-chip, such as ring-resonators, chip-integrated interferometers such as Mach_Zehnder interferometers, wire waveguides, photonic crystals, slot waveguides and the like, in any material system, where the slab material may comprise any material which may be formed into an optical waveguide. In such systems the microfluidic channel walls that pass over the crossing waveguides would effectively fill the channel when fluid flows through the channels and prevent the fluid from leaking out of the microfluidic channels.

FIG. 3A is an enlarged top view of the photonic crystal patterned regions 21, 22, 23, and 24 at the termination of the ridge waveguides 1221, 1222, 1223, and 1224, respectively. The core of the photonic crystal patterned region 21 comprises a functional photonic crystal waveguide 12212, an input impedance taper 12211 at the input end of the photonic crystal waveguide between the input ridge waveguide 1221 and the photonic crystal waveguide 12212 and an output impedance taper 12213 at the output end of the photonic crystal waveguide between the output ridge waveguide 2050 and the photonic crystal waveguide 12212. Only one photonic crystal microcavity 12214 is shown arrayed along the length of the photonic crystal waveguide 12212 for clarity. In general, p=1, 2, 3 . . . P photonic crystal microcavities can be arrayed along the length of the single photonic crystal waveguide 12212. For instance, two photonic crystal microcavities 12244 and 12245 are arrayed along the length of the functional photonic crystal waveguide 12242 in the photonic crystal patterned region 24.

Between the ridge waveguide 1221 and the photonic crystal waveguide 12212, at the input end of the photonic crystal waveguide, there is an impedance taper 12211 for coupling of light from ridge waveguide to photonic crystal waveguide with high efficiency. Similarly, between the photonic crystal waveguide 12212 and the output ridge waveguide 2050, at the output end of the photonic crystal waveguide, there is another impedance taper 12213 for better coupling efficiency. The waveguides are tapered by shifting the columnar members by x times α in the direction perpendicular to 12212, in the plane of the waveguide, where α is the lattice constant and x varies from 0.01 to 0.1 in steps of 0.01, from photonic crystal waveguide to ridge waveguide. Optical confinement of light that propagates in the core in the photonic crystal patterned region comprising the functional photonic crystal waveguide 12212, input and output impedance tapers 12211 and 12213, respectively, is achieved in the horizontal plane of the slab, parallel to the plane of the substrate, by the periodic lattice structure of the photonic crystal patterned region 21 with two-dimensional periodicity. Optical confinement in the direction out of the plane of the slab is achieved by total internal reflection between the high index slab material in the core and the lower refractive indices of the top cladding 106 and bottom cladding 105, relative to the slab 101.

FIG. 3B shows a cross section of the device along the line J-J' of FIG. 3A. We assume that the PDMS mold 108*x* is bonded on top. Along the line J-J', the primary waveguides 1221 and 1222 exist. Both these waveguides are formed from part of the slab. By comparing with FIG. 3A, we note that in FIG. 3A, the white regions are part of the semiconductor slab 101 and all black areas are voids formed by etching the corresponding features as defined by the black areas, into the slab 101 either completely or partially through the slab. These voids are denoted, along the line J-J' of FIG. 3A, by 101*x*. Since the PDMS mold 108*x* will not close the voids 101*x*, when fluids flow through the microfluidic channels formed by PDMS, fluids will leak through the voids 101*x*. In the absence of crossing waveguides 2001, 2002 etc., fluids would always leak through the voids 101*x*. These voids 101*x* are closed by the crossing waveguides 2001, 2002 etc. as shown in FIG. 3C. The significance of this design is that no additional lithography patterning is needed to close the voids 101*x*. The crossing waveguides 2001, 2002 etc. are patterned by lithography in the same step in which all other device patterns (denoted by the white areas in FIG. 1A and FIG. 1B) are defined.

FIG. 3C shows a cross section of the device along the line J1-J1' of FIG. 3A. We also assume that the PDMS (poly dimethyl siloxane) mold 108*x* is bonded on the chip. A void exists between the waveguides in FIG. 3B. In FIG. 3C, the void has been closed by the crossing waveguide. We assume in FIG. 3C that w=1. The same cross-section would exist in each and every crossing waveguide cross-section J1-J1' at each intersection with the primary waveguide(s). One skilled in the art will note that the PDMS mold indicated by 108*x* as shown in FIG. 3*b* and FIG. 3C is representative of any material that may form a microfluidic channel bonded to the chip.

FIG. 4 is an enlarged top view of a section of the photonic crystal patterned region 21 showing the functional photonic crystal microcavity 12214 coupled to the functional photonic crystal waveguide 12212. The columnar members 102 etched into the slab are also shown. The photonic crystal waveguide 12212 is defined by filling a complete row of columnar members with the semiconductor slab material 101. Similarly, a photonic crystal microcavity, for instance 12214, is defined by filing a row of 3 columnar members 102 with semiconductor material 101. One skilled in the art will notice that the photonic crystal microcavity 12214 can have different geometries as described in the literature. The core 141 is the region through which the light propagates in the photonic crystal waveguide.

FIG. 5 is an enlarged top view of the input sub-wavelength grating coupler 200 defined in the semiconductor slab 101. Rectangular voids 901 are etched into the region 200 in the form of a rectangular array. Input ridge waveguide 1110, the first stage MMI 111, and the corresponding output ridge waveguides from the MMI, which are 1111, 1112, 1113, and 1114 are also shown.

FIG. 6 is an enlarged top view of the output sub-wavelength grating couplers 205, 206, 207, and 208 defined in the semiconductor slab 101. The elements 205, 206, 207, and 208 are at the output end of the ridge waveguides 2050, 2060, 2070, and 2080, respectively. The ridge waveguides 2050, 2060, 2070, and 2080 originate from the photonic crystal patterned regions 21, 22, 23, and 24, respectively. Rectangular voids 901 are etched into the regions 205, 206, 207, and 208 in the form of a rectangular array.

FIG. 7 is a schematic cross-section of FIG. 4 taken along the plane C-C' in the photonic crystal patterned region. FIG. 7 shows the substrate 107, the bottom cladding 105 disposed on the substrate, the semiconductor slab 101 disposed on the bottom cladding with columnar members 102 etched through the slab. In one embodiment, the top cladding 106 is air. When analytes are introduced in solution on top of the device, the analyte medium forms the top cladding 106. However, one skilled in the art will note that the top cladding can be any organic or inorganic dielectric material and columnar members 102 can extend through 101 as well as through the bottom cladding 105 to reach the substrate 107. The material of the top cladding 106 can fill the columnar members 102 either fully or partially during device operation. Although the structure within the slab 101 is substantially uniform in the vertical direction in this embodiment, one skilled in the art will understand that vertically non-uniform structure, such as the columnar members 102 whose radii are varying along the vertical direction, may be used as well. The column members 102 can be either simply void or filled with other dielectric materials.

In FIG. 8A, which is a top view of the device in FIG. 1A, the MMIs of all the cascaded stages and the input and output sub-wavelength grating couplers that were shown in FIG. 1A, are covered with a cover polymer 108. The region 700 is kept free from any cover polymer and forms a microfluidic channel. A rigid dielectric cover 109 is put on top of the cover polymer as shown. In some embodiments, the rigid dielectric cover 109 may be absent. This embodiment is illustrated in FIG. 8B. The photonic crystal patterned regions are kept free from any cover polymer. The cover polymer must be transparent at the wavelength of operation of the device. The cover polymer thus forms the top cladding for the sub-wavelength grating couplers, the MMIs, and the input and output ridge waveguides.

FIG. 9A is the top view of the device in FIG. 8A which shows the individual polymer molecules or biomolecules 401, 402, 403, 404, 405, and 406 on top of the photonic crystal microcavities in each arm of the device. One or more photonic crystal microcavities may be coated with the same or different polymer molecule or biomolecule. Similarly, FIG. 9B is the top view of the device in FIG. 8B showing the disposition of one or more, same or different, polymer molecules or biomolecules on the one or more photonic crystal microcavities.

In one embodiment, the biomolecule can be proteins, nucleic acids, DNA, RNA, antigens, antibodies, small molecules, peptides, genes etc. Each biomolecule can be specific to a particular disease causing conjugate where the disease of interest can be cancer, malaria, leptospirosis, or any infectious disease to achieve specific detection. In another embodiment, the polymer molecule can be a hydrogel that swells in the presence of a specific analytical solution or ambient gas wherein the ambient gas includes, but is not limited to, greenhouse gases such as carbon dioxide, methane, nitrous oxide, or other gases such as oxygen, nitrogen, thereof. In yet another embodiment, the substance can be a polymer that changes its effective refractive index upon contact with a chemical substance or proportionately to changes in temperature, humidity, pressure, and/or ions in solution thereof.

FIG. 10A is a cross-section of the device along the MMI 111 in the direction shown in FIG. 2A by the line A-A'. In FIG. 2A, the top cover polymer and top rigid dielectric were not shown for clarity. In FIG. 8A, the MMI 111 is located below the top cover polymer and the top rigid dielectric and is thus not visible. The cross-section thus shows the layer structure of the device at the location of the multimode interference power splitter, showing the substrate 107, the bottom cladding 105, the slab 101 into which the MMI 111 is defined, the top cover polymer 108, and the top rigid dielectric 109. FIG. 10B is a cross-sectional view of the device in FIG. 2A along the plane A-A', without the top cover polymer layer and the rigid dielectric cover. The cross-section thus shows the layer structure of the device at the location of the multimode interference power splitter, showing the substrate 107, the bottom cladding 105 and the slab 101 into which the MMI 111 is defined. When PDMS microfluidic channel molds are used, the polymer layer and rigid dielectric covers are absent.

FIG. 11A is a cross-section of the device along the sub-wavelength grating coupler 200, at the input in the direction shown in FIG. 5 by the line B-B'. In FIG. 5, the top cover polymer and top rigid dielectric were not shown for clarity. In FIG. 8A, the sub-wavelength grating coupler 111 is located below the top cover polymer and the top rigid dielectric and is thus not visible. The cross-section thus shows the layer structure of the device at the location of the sub-wavelength grating coupler 200, showing the substrate 107, the bottom cladding 105, the slab 101 into which the sub-wavelength grating coupler 200 is defined, the top cover polymer 108 and the top rigid dielectric 109. Rectangular voids etched into the element 200 are indicated by 901. The voids 901 are partially or fully filled with the top cover polymer 108. A void 1071 is etched from the backside into the substrate 107. Light is incident into the sub-wavelength grating coupler from an external light source via the void 1071 in the substrate 107. FIG. 11B is a cross-sectional view of the device in FIG. 5 along the plane B-B', without the top cover polymer layer and the rigid dielectric cover. The cross-section thus shows the layer structure of the device at the location of the sub-wavelength grating coupler 200, showing the substrate 107, the bottom cladding 105, and the slab 101 into which the sub-wavelength grating coupler 200 is defined. When PDMS microfluidic channel molds are used, the polymer layer and rigid dielectric covers are absent.

FIG. 12 is similar to FIG. 1A, except the photonic crystal patterned region comprises a photonic crystal slot waveguide with one or more rectangular voids or slots along the length of the photonic crystal waveguide, the input impedance taper in the photonic crystal waveguide, the output impedance taper in the photonic crystal waveguide and the input and output ridge waveguides from the photonic crystal pattern. Detailed description of FIG. 12 follows:

FIG. 12 presents a top view schematic drawing of a multiplexed photonic crystal slot waveguide device. It comprises a functional MMI 111 with one input arm 1110 which is a ridge waveguide and 4 representative output arms 1111, 1112, 1113, and 1114 which are four ridge waveguides. On each output arm 1111, 1112, 1113, and 1114, the second stage of a functional MMI is made. One skilled in the art will note that the number of output arms, shown as four in the figure can actually be any number n=1, 2, 3, 4, 5 . . . N. A representative second stage MMI on the arm 1112 is denoted as 122. The MMI 122 has four output arms 1221, 1222, 1223, and 1224 which are four ridge waveguides. Elements 1221, 1222, 1223, and 1224 have been shown in detail in FIG. 13 to avoid cluttering in FIG. 12. Only two (2) MMI stages are shown here, but one skilled in the art will note that the number of cascaded MMI stages can be cascaded m times where m=1, 2 . . . M. Crossing waveguides 2001 and 2002 at the input side and on the output side of the photonic crystal patterned regions, respectively, are shown.

Light is coupled into the input arm 1110 of the MMI 111 via a sub-wavelength grating coupler 200. The output light from each output ridge waveguide, in one instance, the output ridge waveguide 2050 is coupled out of the plane of the slab 101 by an output sub-wavelength grating coupler 205. Sub-wavelength grating couplers 201, 202, 203 . . . 216 couple light out from the output ridge waveguides 2010, 2020, 2030 . . . 2160, respectively, out of the plane of the slab 101.

FIG. 13 is an enlarged top view of the input section of the photonic crystal patterned regions 25, 26, 27, and 28 in FIG. 12. Each output arm 1221, 1222, 1223, and 1224 is a ridge waveguide that terminates in functional mode converter sections 1225, 1226, 1227, and 1228, respectively, that transform the optical mode propagating down a conventional ridge waveguide into a slot waveguide or slotted ridge waveguide as defined by 351, 361, 371, and 381, respectively. The slot waveguides or slotted ridge waveguides 351, 361, 371, and 381 are defined by one or more rectangular slots or voids 35, 36, 37, and 38, respectively, etched through the ridge waveguide. The core of the photonic crystal patterned region 26 comprises a functional photonic crystal waveguide 12222, an input impedance taper 12221 between the input slot waveguide 361 and the photonic crystal waveguide 12222, and an output impedance taper 12223 between the output slot waveguide 461 and the photonic crystal waveguide 12222. The one or more rectangular slots or voids 36 for instance extend along the entire length of the functional photonic crystal waveguide 12222, the input impedance taper 12221, and the output impedance taper 12223. An output slot mode converter 12261 converts the propagating optical mode in the slot waveguide 461 to a ridge waveguide optical mode in the output ridge waveguide 2060. A similar description applies to the output slot mode converters 12251, 12271, and 12281.

The photonic crystal patterned regions 25, 26, 27, and 28 include a number of column members 102 etched through or partially into the semiconductor slab 101. Within each photonic crystal patterned region, the waveguide core 141 is defined as the space between the centers of two column members adjacent to the region where the columns are filled with the material of the slab. In one preferred embodiment, the column members 102 are arranged to form a periodic lattice with a lattice constant α. In some embodiments, the width of waveguide core 141 can range from 0.5 times sqrt(3) times the lattice constant or period α to 50 times sqrt(3) times the lattice constant or period α. The cross sections along J4' and J141' of FIG. 13 are the same as those in FIG. 3B and FIG. 3C, respectively. The crossing waveguide regions for instance of the primary waveguide 1221 with the crossing waveguide 2001 are similarly represented by FIG. 2B, FIG. 2C, FIG. 2D, and FIG. 2E. The crossing waveguide regions for instance of the primary waveguide 2050 with the crossing waveguide 2002 are similarly represented by FIG. 2B, FIG. 2C, FIG. 2D, and FIG. 2E. The waveguide crossings 2001, in FIG. 12 and FIG. 13, occur prior to the mode converter (for example 1225) on the input side of the photonic crystal patterned region 25. The waveguide crossings 2002, in FIG. 12 and FIG. 13, occur after the mode converter (for example 12251) on the output side of the photonic crystal patterned region 25.

FIG. 14 is a schematic cross-section of the photonic crystal patterned region in FIG. 13 taken along the plane D-D'. FIG. 14 shows the substrate 107, the bottom cladding 105 disposed on the substrate, the semiconductor slab 101 disposed on the bottom cladding with columnar members 102 etched through the slab. The rectangular slot or void etched in the middle of the photonic crystal waveguide is indicated by 36. A hydrophobic polymer 106 forms the top cladding. One skilled in the art will note that columnar members 102 and rectangular slot 36 can extend through 101 as well as through the bottom cladding 105 to reach the substrate 107. The material of the top cladding 106 can fill the columnar members 102 and the slot 36 either fully or partially during device operation. Although the structure within the slab 101 is substantially uniform in the vertical direction in this embodiment, one skilled in the art will understand that vertically non-uniform structures, such as the columnar members 102 whose radii are varying along the vertical direction, may be used as well.

FIG. 15A is the top view of the packaged device showing the layout of the chip in FIG. 1A in the package or shell 600. The package shell comprises a top portion, a bottom portion, and a side wall portion which together surround an interior volume. The side wall portion of the package shell may comprise four side walls. Alternatively, the side wall portion may comprise one or more side walls. In the case of a single side wall, the resulting shell is cylindrical. Square grooves 601, 602, 603, and 604 are made at the four corners of the package. The package 600 may be ceramic, plastic, or any material which provides toughness and environmental protection to the internal semiconductor chip. The opening in the package 701 on the top side is aligned with the microfluidic channel opening 700 in the semiconductor chip.

FIG. 15B is a top view of the arrayed device within an outer package including the PDMS microfluidic channel mold 108x. The package shell comprises a top portion, a bottom portion, and a side wall portion which together surround an interior volume. The side wall portion of the package shell may comprise four side walls. Alternatively, the side wall portion may comprise one or more side walls. In the case of a single side wall, the resulting shell is cylindrical. Square grooves 601, 602, 603, and 604 are made at the four corners of the package. The package 600 may be ceramic, plastic, or any material which provides toughness and environmental protection to the internal semiconductor chip.

FIG. 16 is the bottom view of the package. Opening 1071 is made in the package aligned with the position of the sub-wavelength grating coupler 200 on the semiconductor chip. The size of the opening 1071 is larger than the size of the sub-wavelength grating coupler 200. Opening 1072 is made in the package aligned with the positions of all the output sub-wavelength grating couplers 201, 202, 203 . . . 216. The size of the opening 1072 is larger than the area covered by all the sub-wavelength grating couplers 201, 202, 203 . . . 216.

FIG. 17A is a cross-sectional view taken along the plane E-E' in FIG. 16 through the input sub-wavelength grating coupler 200. FIG. 17A shows the layout of the semiconductor chip within the package 600. A hole or void is etched into the substrate 107 of the semiconductor chip. The opening 1071 in the bottom of the package aligned with the input sub-wavelength grating coupler 200 is shown. The sub-wavelength grating coupler rests on the bottom cladding 105. The rectangular voids 901 of the sub-wavelength grating coupler in the slab 101 are shown. The top cover polymer 108 and the rigid dielectric cover 109 are also shown. The top cap of the package 600 is finally shown. In some embodiments, the rigid dielectric cover 109 may be absent and the top cap of the package 600 is located on top of the cover polymer 108.

On the input sub-wavelength grating coupler 200, light is incident from an external optical source into the chip via the sub-wavelength grating couplers in the direction as indicated by the broad bold arrow in FIG. 17A. At the output sub-wavelength grating couplers 201, 202, 203 . . . 216, light exits from the sub-wavelength grating couplers in the direction as indicated by the bold dashed arrow in FIG. 17A. Although the arrows have been drawn to achieve normal incidence into and normal emission from sub-wavelength grating couplers, one skilled in the art will note that the sub-wavelength grating couplers can be designed to achieve maximum coupling efficiency into and out of the semiconductor chip by considering an angle of incidence φ from the out-of-plane normal to the sub-wavelength grating where φ can vary continuously from zero to forty degrees and from zero to negative forty degrees.

FIG. 17B is cross-section view of the package with the chip inside along the plane E-E' in FIG. 16, when the cover polymer and rigid dielectric are absent and instead replaced by a PDMS microfluidic channel 108x. Other components are similar to those described in FIG. 17A.

FIG. 18A is the top view of a second embodiment of the packaged optical chip showing the layout of the chip in FIG. 1A in the package 600. Square grooves 601, 602, 603, and 604 are made at the four corners of the package. The package 600 may be ceramic, plastic, or any material which provides toughness and environmental protection to the internal semiconductor chip. The opening in the package 701 on the top side is aligned with the microfluidic channel opening 700 in the semiconductor chip. Openings are made in the package 600 as bordered by the segments 1071 and 1072. The element 109 is also voided in the region bordered by 1071 and 1072 so that the element 108 is exposed. In essence, light is then coupled into the semiconductor chip from the top of the chip from external optical sources and through the top cover polymer cover 108. Similarly, light is coupled out of the semiconductor chip from the top of the chip to external optical detectors and through the top cover polymer cover 108.

FIG. 18B is a top view of the arrayed device within an outer package in a second embodiment in which the light is incident and also exits the chip from the top. Light is incident on the input sub-wavelength grating coupler. Light exits from the output sub-wavelength grating couplers to the detector. In this case, the cover polymer and rigid dielectric are absent, and instead a PDMS microfluidic channel 108x is bonded to the arrayed device. Other components are similar to those described in FIG. 18A.

FIG. 19A is a cross-sectional view taken along the plane F-F' in FIG. 18A through the input sub-wavelength grating coupler 200. FIG. 19A shows the layout of the semiconductor chip within the package 600. A hole or void is made in the package 600 and in the element 109 in the regions bordered by 1071 and 1072. The sub-wavelength grating coupler rests on the bottom cladding 105. The rectangular voids 901 of the sub-wavelength grating coupler in the slab 101 are shown. The top cover polymer 108 and the rigid dielectric cover 109 are also shown. In some embodiments, the rigid dielectric cover 109 may be absent and the top cap of the package 600 is located on top of the cover polymer 108.

FIG. 19B is a cross-section view of the package with the chip inside along the plane F-F' in FIG. 18B for the case of the second embodiment where the light is incident from the top and is also collected from the top of the chip. In this case, the cover polymer and rigid dielectric are absent, and instead a PDMS microfluidic channel 108x is bonded to the arrayed device. Other components are similar to those described in FIG. 19A.

FIG. 20 is the top view of a third embodiment of the packaged optical chip showing the layout of the chip in FIG. 1A in the package 600. Square grooves 601, 602, 603, and 604 are made at the four corners of the package. The package 600 may be ceramic, plastic, or any material which provides toughness and environmental protection to the internal semiconductor chip. The opening in the package 701 on the top side is aligned with the microfluidic channel opening 700 in the semiconductor chip. Openings are made in the package 600 as bordered by the segments 1071 and 1072. The elements 108 and 109 are also voided in the region bordered by 1071 and 1072 so that the input sub-wavelength grating coupler 200 and the output sub-wavelength grating couplers 201, 202, 203 . . . 216 are exposed. In essence, light is then coupled into the semiconductor chip from the top of the chip from external optical sources and directly into the input sub-wavelength grating coupler 200. Similarly, light is coupled out of the semiconductor chip from the top of the chip to external optical detectors and directly from the output sub-wavelength grating couplers 201, 202, 203 . . . 216.

FIG. 21 is a cross-sectional view taken along the plane G-G' in FIG. 20 through the input sub-wavelength grating coupler 200. FIG. 21 shows the layout of the semiconductor chip within the package 600. A hole or void is made in the package 600 and in the elements 108 and 109 in the regions bordered by 1071 and 1072. The opening 1071 in the top of the package aligned with the input sub-wavelength grating coupler 200 is shown. The sub-wavelength grating coupler rests on the bottom cladding 105. The rectangular voids 901 of the sub-wavelength grating coupler in the slab 101 are shown. The top cover polymer 108 and the rigid dielectric cover 109 are also shown. In some embodiments, the rigid dielectric cover 109 may be absent and the top cap of the package 600 is located on top of the cover polymer 108.

FIG. 22 is a bottom view of the packages described by FIG. 18A and FIG. 19A. FIG. 22 is also the bottom view of the package described by FIG. 20 and FIG. 21. Square grooves 601, 602, 603, and 604 made at the four corners of the package can be seen.

FIG. 23A is a view of the package described in FIG. 15A, FIG. 15B, FIG. 16, FIG. 17A, FIG. 17B, FIG. 18A, FIG. 18B, FIG. 19A, FIG. 19B, FIG. 20, and FIG. 21, observing from the end L or L' in FIG. 22. FIG. 23B is a view of the package described in FIG. 15A, FIG. 15B, FIG. 16, FIG. 17A, FIG. 17B, FIG. 18A, FIG. 18B, FIG. 19A, FIG. 19B, FIG. 20, and FIG. 21, observing from the end K or K' in FIG. 22. The positions of the grooves 601, 602, 603, and 604 are also indicated.

FIG. 24A, FIG. 24B, FIG. 24C, and FIG. 24D show the transmission output spectra from the output sub-wavelength grating couplers 205, 206, 207, and 208, respectively. From FIG. 8A, we note that the ridge waveguides that output to the output sub-wavelength grating couplers 205, 206, 207, and 208 are respectively numbered as 2050, 2060, 2070, and 2080. We also note from FIG. 8A that the ridge waveguides 2050, 2060, 2070, and 2080 output from the photonic crystal patterned regions 21, 22, 23, and 24, respectively. From FIG. 8A and FIG. 9A we note that the photonic crystal microcavity in the patterned region 21 is coated with a biomolecule 401, the photonic crystal microcavity in the patterned region 22 is coated with a biomolecule 402, the photonic crystal microcavity in the patterned region 23 is coated with a biomolecule 403, and the two photonic crystal microcavities in the patterned region 24 are coated with biomolecule 404 and biomolecule 401.

Figure 24A:
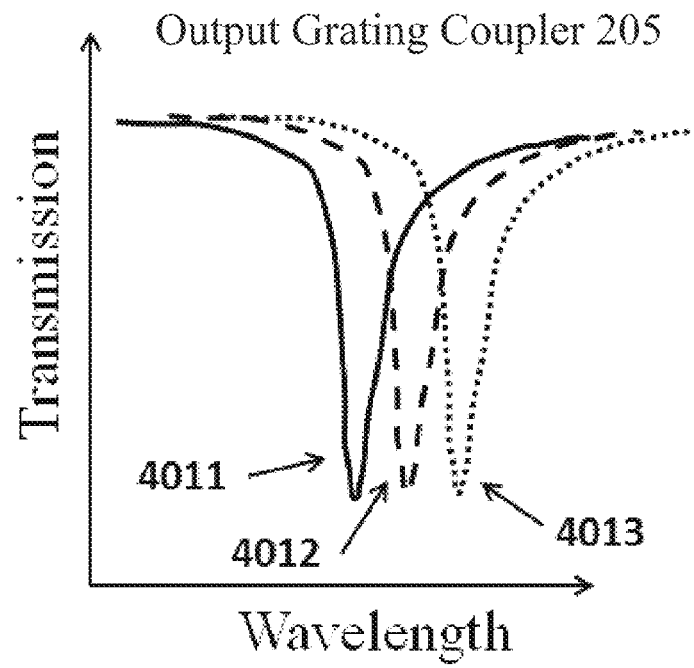
Figure 24B:
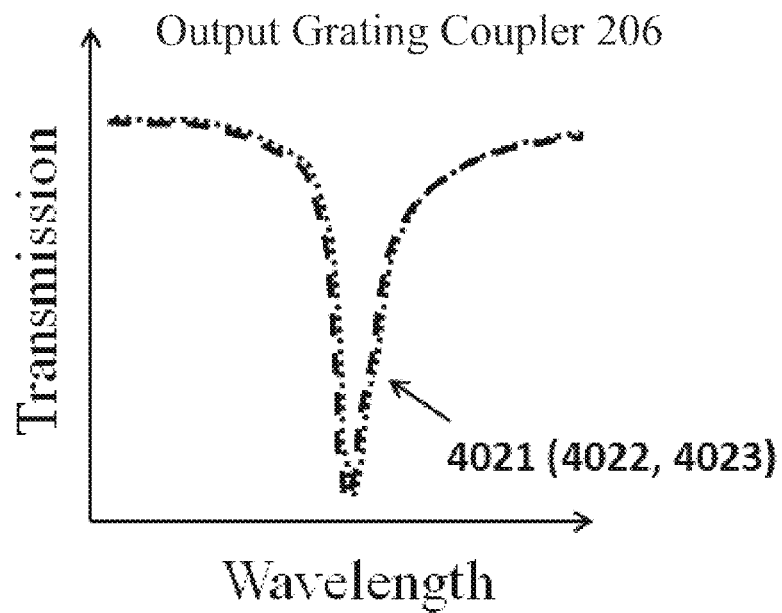
Figure 24C:
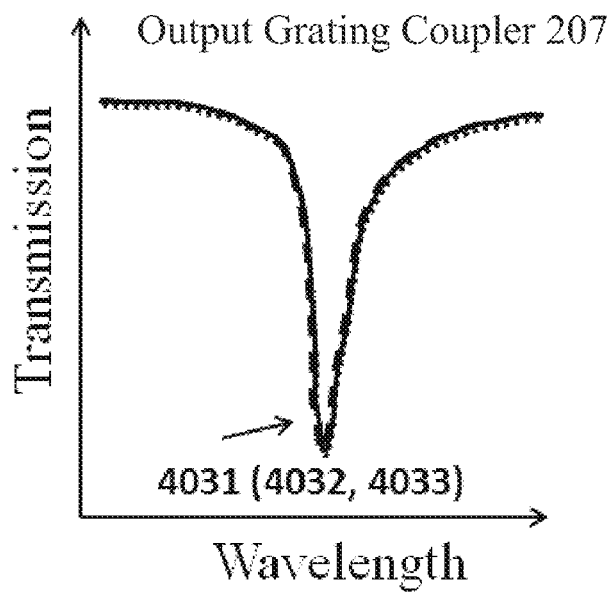
Figure 24D:
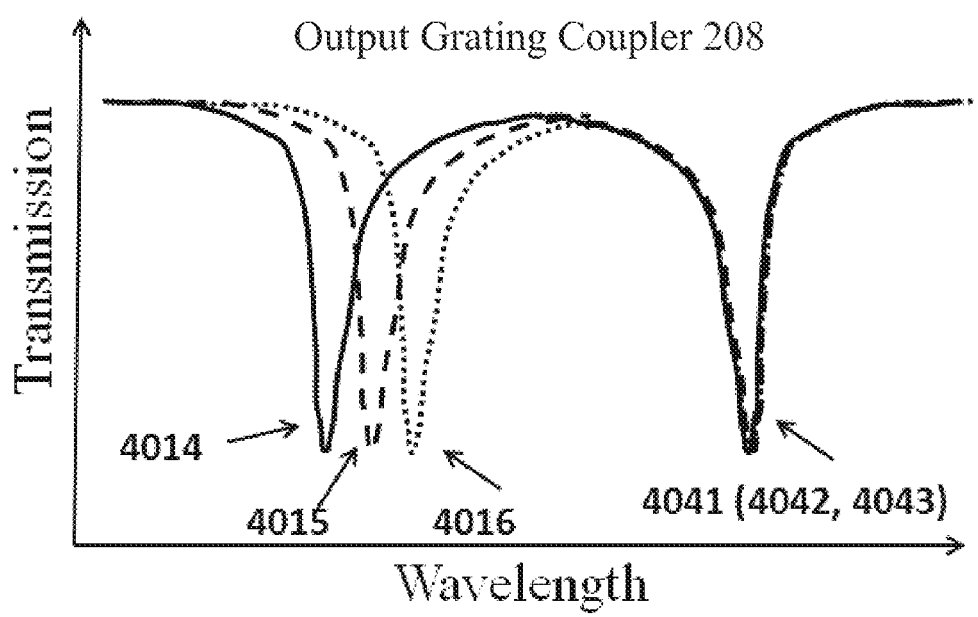

FIG. 24A illustrates a typical transmission spectrum from the 4 output arms of a 1×4 MMI with a photonic crystal waveguide coupled microcavity in each arm. The microcavity sensors in output arms #1, #2, #3, and #4 are coated with unique target receptor biomolecules T1, T2, T3, and T4, respectively. When a sample solution containing only the probe biomolecule P1 which binds specifically to biomolecule T1 and does not bind to any of biomolecules T2 or T3, only the resonance wavelength in arm #1 coated with target receptor biomolecule T1 shifts. Resonances in arms #2, #3, and #4 do not shift. When a sample solution containing the secondary antibody S2 which binds specifically to probe biomolecule P1 and does not bind to any of T2, T3, or T4 is now introduced, a secondary resonance wavelength shift in arm #1 occurs. Resonances in arms #2, #3, and #4 do not shift. Binding specificity is thus confirmed from the multiplexed sandwich detection of the specific probe P1. Control antibodies T2, T3, and T4 also confirm specificity by showing no binding response to the probe biomolecule P1. In FIG. 24A, FIG. 24B, FIG. 24C, and FIG. 24D, the solid black curves represent the baseline transmission spectrum obtained from the output sub-wavelength grating couplers 205, 206, 207, and 208, respectively, when the photonic crystal microcavities in the corresponding photonic crystal patterned regions 21, 22, 23, and 24, respectively are coated with biomolecules 401, 402, 403, and (401 and 404), respectively and the device is immersed in the analyte that fills the area in the microfluidic channel 700 as described before in FIG. 9A. The resonance wavelengths from each of 205, 206, 207, and 208 are denoted by 4011, 4021, 4031, and (4014 and 4041), respectively. When an analyte containing the probe biomolecule P1 which is the specific conjugate of the target biomolecule 401 is introduced, the new positions of the resonance wavelengths in each of FIG. 24A, FIG. 24B, FIG. 24C, and FIG. 24D are denoted by the black dashed curves. The resonance wavelength 4011 shifts to 4012 and the resonance wavelength 4014 shifts to 4015. Other resonance wavelength 4021, 4031, and 4041 do not shift at all and thus 4022, 4032, and 4042 are the same as 4021, 4031, and 4041. To confirm that the biomolecule P1 that bound to 401 is a specific conjugate of 401, an analyte containing the secondary antibody S2 is introduced in the device microfluidic channel, and the corresponding new positions of the resonance wavelengths in each of FIG. 24A, FIG. 24B, FIG. 24C, and FIG. 24D are denoted by the black dotted curves. The resonance wavelengths 4012 and 4015 further shift to 4013 and 4016, respectively, while the resonance wavelengths 4022, 4032, and 4042 remain at the same position as denoted by 4023, 4033, and 4043. The lack of any resonance wavelength shift from the photonic crystal microcavities coated with 402, 403 and 404 and the multiplexed observation of resonance wavelength shift from the photonic crystal microcavities coated with 401 in the same measurement, together with the secondary resonance wavelength shift observed upon the introduction of the secondary antibody S2, validate the method by which binding specificity is achieved by multiplexed experiments in the same measurement. We emphasize "same measurement" because light is incident into the input sub-wavelength grating coupler 200 and is collected from all output sub-wavelength grating couplers 201, 202, 203 . . . 216 at the same time.

While the measurement has been described with respect to biomolecules, one skilled in the art will note that the discussion in FIG. 24A, FIG. 24B, FIG. 24C, and FIG. 24D is applicable to polymer molecules that respond to specific chemical signatures, or ambient conditions such as ion concentration in solution, gas concentration in ambient, temperature, pressure, or humidity.

In FIG. 25, we describe one embodiment of the output waveguide configuration to output light from all the output waveguides 2010, 2020, 2030 . . . 2160 using a single multimode interference power combiner 309. The output from the multimode interference power combiner 309 inputs light via waveguide 3000 into a single output sub-wavelength grating coupler 300.

In FIG. 26, we describe a second embodiment of the output waveguide configuration to output light from all the output waveguides 2010, 2020, 2030 . . . 2160 using cascaded stages of multimode interference power combiners 321, 322, 323, and 324 that finally output to a single multimode interference power combiner 325. The output from the multimode interference power combiner 325 inputs light via waveguide 3000 into a single output sub-wavelength grating coupler 300.

In FIG. 27, we describe a third embodiment of the output waveguide configuration to output light from all the output waveguides 2010, 2020, 2030 . . . 2160 using cascaded stages of Y-junction ridge waveguide power combiners 821, 822, 823 . . . 835 that finally output to a single output sub-wavelength grating coupler 300 via waveguide 3000. A Y-junction ridge waveguide may also be described as two-to-one ridge waveguide junctions. One skilled in the art will also note that cascaded stages of Y-junction ridge waveguide power combiners may also be used at the input end as Y-junction one-to-two ridge waveguide power splitters replacing all the multimode interference power splitters at the input end in order to couple light from the input sub-wavelength grating coupler 200 to each of the sixteen photonic crystal patterned regions in FIG. 1A and FIG. 1B.

FIG. 28A, FIG. 28B, FIG. 28C, and FIG. 28D show characteristic transmission spectra observed on the output sub-wavelength grating couplers 205, 206, 207, and 208 separately when the photonic crystal patterns 21, 22, 23, and 24 on the corresponding arms have the same lattice constant.

FIG. 28E confirms that in the embodiments described by FIG. 3A, when separate photonic crystal patterns 21, 22, 23, and 24 have the same lattice constant, the transmission spectra from all the sub-wavelength grating couplers are measured separately by separate external optical fibers or separate external photodetectors. Thus if all the outputs of FIG. 28A, FIG. 28B, FIG. 28C, and FIG. 28D were combined into a single output, it would not be possible to distinguish the separate resonances of the photonic crystal microcavities from the separate photonic crystal patterns 21, 22, 23, and 24.

FIG. 29A, FIG. 29B, FIG. 29C, and FIG. 29D show characteristic transmission spectra observed on the output sub-wavelength grating couplers 205, 206, 207, and 208 separately when the photonic crystal patterns 21, 22, 23, and 24 on the corresponding arms have different lattice constants. In this way, instead of separate output sub-wavelength grating couplers 201, 202, 203 . . . 216, as shown in FIG. 1A and FIG. 1B, we can have a single output sub-wavelength grating coupler 300, as described in FIG. 25, FIG. 26, and FIG. 27, so that a combined transmission spectrum as shown in FIG. 29E is obtained at the single output sub-wavelength grating coupler 300. In contrast to FIG. 28E, it is possible in FIG. 29E to distinguish the separate resonances of the photonic crystal microcavities from the separate photonic crystal patterns 21, 22, 23, and 24 from the combined output of the single output sub-wavelength grating coupler 300.

In FIG. 30, the external optical fiber 609 at the input sub-wavelength grating coupler is glued to the package 600 via an ultra-violet cured polymer 610 such as epoxy. Although FIG. 30 has been shown for the input sub-wavelength grating coupler, one skilled in the art will note that the configuration described by FIG. 30 is the same for all output sub-wavelength grating couplers as described by FIG. 1A and FIG. 1B, using a separate fiber 609 for each output sub-wavelength coupler 201, 202, 203 . . . 216 or a single fiber for all the output sub-wavelength grating couplers 201, 202, 203 . . . 216. One skilled in the art will also note that the same configuration as FIG. 30 also holds for the cross-section across the single output sub-wavelength grating couplers 300 shown in FIG.

25, FIG. 26, and FIG. 27. The external optical fiber is aligned at an angle φ where φ may vary continuously from zero degrees to forty (40) degrees as determined by the designed angle for maximum optical coupling efficiency with the sub-wavelength grating coupler at both the input and output.

In FIG. 31, the external optical fiber 609 is polished at an angle φ as determined by the angle φ for maximum coupling efficiency in FIG. 30 for incident light into the input sub-wavelength grating coupler or exiting light from the output sub-wavelength grating couplers to the external optical fiber at the output. The dashed arrow shows the direction of light coupling at the input. One skilled in the art will note that the direction of light coupling at the output essentially reverses the direction of the dashed arrow. In one embodiment, a reflecting material such as gold is deposited on the polished facet 611 to enhance the optical coupling efficiency. While FIG. 31 has been drawn for the case of coupling light into and out of the input and output sub-wavelength grating couplers respectively from the bottom of the device, one skilled in the art will note that the method of optical coupling with optical fibers with polished facets and gold deposited on the polished facets for enhanced coupling efficiency is also applicable for coupling in and out of the device from the top of the device as illustrated in FIG. 19A, FIG. 19B, and FIG. 21.

In FIG. 32, the output waveguides 2010, 2020 . . . 2160 are bent by 180 degrees so that the output sub-wavelength grating couplers 201, 202, 203 . . . 216 are on the same side of the photonic crystal pattern as the input sub-wavelength grating coupler 200. In this configuration, a single optical fiber bundle comprises individual optical fibers in which one optical fiber couples light into the input sub-wavelength grating coupler 200 and the other optical fibers receive light from the output sub-wavelength grating couplers 201, 202 . . . 216. In this configuration of FIG. 32, if the center-to-center spacing between the sub-wavelength grating couplers 201, 202 . . . 208, 200, 209, 210 . . . 216 in order is known and the external optical fiber bundle has the same center-to-center spacing between individual cores of the external optical fibers as the center-to-center spacing between the sub-wavelength grating couplers 201, 202 . . . 208, 200, 209, 210 . . . 216 in order, then one needs to perform only one optical alignment, for instance of 201 with one external optical fiber in the bundle to ensure that all optical fibers in the bundle are aligned to the respective sub-wavelength grating couplers on the chip. In contrast, in FIG. 1A and FIG. 1B, one would need two separate optical fiber bundles, one bundle for the input sub-wavelength grating coupler or couplers, and one bundle for the output sub-wavelength grating couplers. Thus, during chip-packaging with external optical fibers, one will need to perform two optical alignments, one with the set of input sub-wavelength grating coupler or couplers only, and the other with the set of output sub-wavelength grating couplers. Chip-packaging difficulty is thus reduced in FIG. 32. One skilled in the art will note, that the output waveguides 3000 in each of FIG. 25, FIG. 26, and FIG. 27 can also be bent around by 180 degrees so that the output sub-wavelength grating coupler 300 in each figure is adjacent to the input sub-wavelength grating coupler 200 so that a single optical fiber bundle with two optical fibers in the bundle can be used to couple light into the input sub-wavelength grating coupler 200 from one fiber and couple light out from the output sub-wavelength grating coupler 300 from the second fiber in the bundle.

Figure 33A:
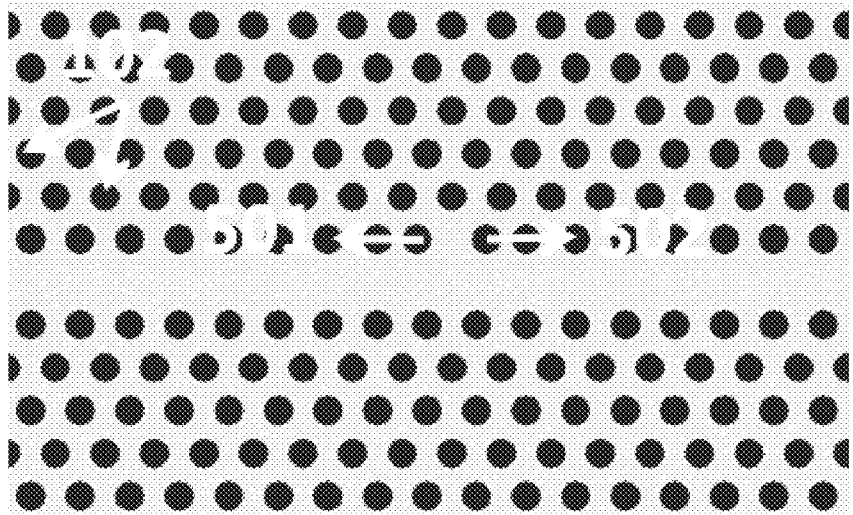
Figure 33B:
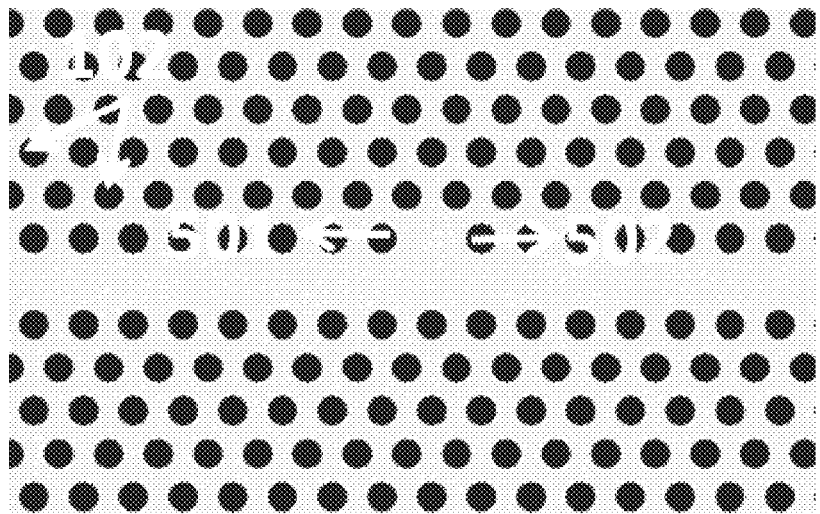
Figure 33C:
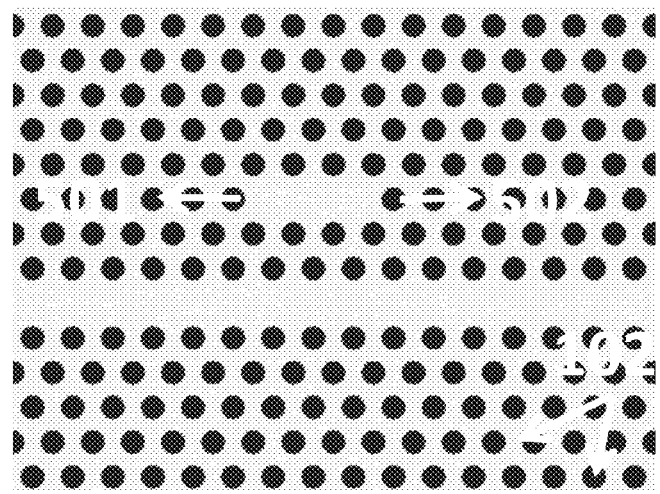
Figure 33D:
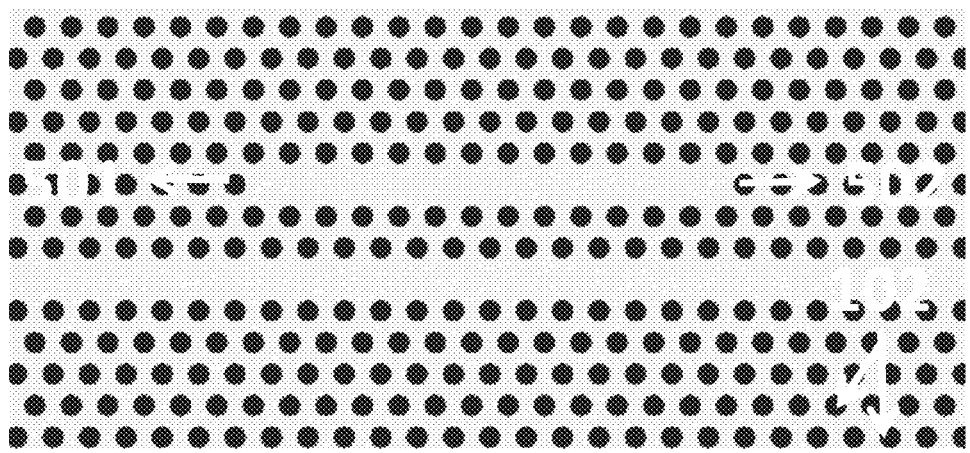
Figure 33E:
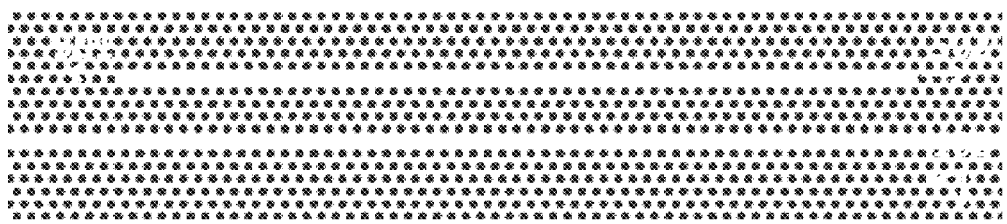
Figure 33F:
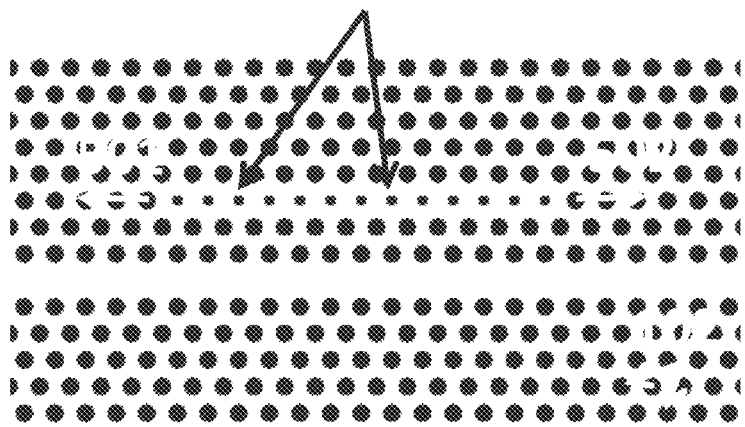
Figure 33G:
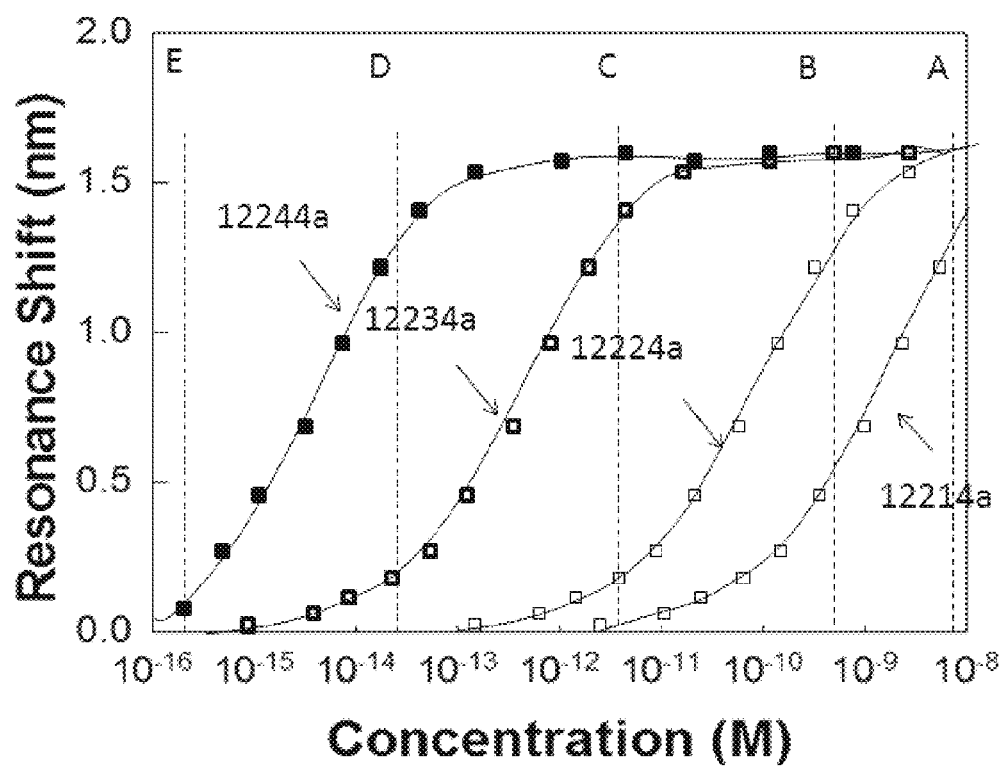

FIG. 33A, FIG. 33B, FIG. 33C, FIG. 33D, FIG. 33E, and FIG. 33F illustrate a 1×4 MMI with a photonic crystal waveguide coupled microcavity in each arm. With reference to FIG. 1A, we assume that the representative 1×4 MMI is 121 and the 4 photonic crystal patterned regions are 21, 22, 23 and 24 (as shown in FIG. 3A). Each optical microcavity geometry is different and all microcavities are coated with the same biomolecule. So in this embodiment, biomolecules 401, 402, 403, and 404, as represented in FIG. 9A, would be the same. The optical microcavity 12214 in arm #1 can be defined by shifting two adjacent holes 501 and 502 in the row next to the photonic crystal waveguide (FIG. 33A). The magnitude of the shift is in the direction shown by arrows in FIG. 33A by x times the lattice constant, where x varies from –0.5 to 0.5. The optical microcavity 12214 in arm #1 can also be defined by removing one hole in the row next to the photonic crystal waveguide (as in FIG. 33B). In this case also, the holes 501 and 502 indicated in FIG. 33B can be shifted in the direction shown by arrows by x times the lattice constant, where x varies from –0.5 to 0.5. The optical microcavity 12214 in arm #1 can be defined by removing 3 holes as shown in FIG. 33C. FIG. 33C is shown representative for 3 missing holes. In this case also, the holes 501 and 502 indicated in FIG. 33C can be shifted in the direction shown by arrows by x times the lattice constant, where x varies from –0.5 to 0.5. The optical microcavity 12224 in arm #2 is defined by removing 13 holes, representatively shown with 13 missing holes in FIG. 33D. The optical microcavity 12234 in arm #3 is defined by removing 55 holes. FIG. 33E is shown representatively for 55 missing holes. In this case also, the holes 501 and 502 indicated in FIG. 33E can be shifted in the direction shown by arrows by x times the lattice constant, where x varies from –0.5 to 0.5. Finally, the optical microcavity 12244 in arm #4 is defined by a structure as shown in FIG. 33F, where instead of missing holes as shown in FIG. 33D for a representative optical microcavity with 13 missing holes, holes that are smaller in diameter than the diameter of the holes 102 are etched in the locations of the previous missing holes. The smaller holes are denoted by 102a. The diameter of the smaller holes 102a is Y times the diameter of the holes 102 where Y is a fraction less than 1. In this case also, the holes 501 and 502 indicated in FIG. 33F can be shifted in the direction shown by arrows by x times the lattice constant, where x varies from –0.5 to 0.5. Smaller holes 102a can be similarly etched for all possible optical microcavity configurations described above in FIG. 33A, FIG. 33B, FIG. 33C, and FIG. 33D. All optical microcavities are coated with the same target receptor biomolecules T. However, depending upon the optical microcavity geometry, each optical microcavity can measure only a certain range of concentration of the analyte molecule or biomolecule binding to the target receptor biomolecules. FIG. 33G shows the resonance wavelength shift versus concentration observed for the 4 separate arms. Representative concentrations are plotted on the horizontal axis. Representative resonance wavelength shifts are plotted on the vertical axis. The resonance wavelength shift versus concentration for all four optical microcavities 12214, 12224, 12234, and 12244 are given by 12214a, 12224a, 12234a, and 12244a, respectively. Discrete points are obtained for discrete concentrations measured. The scatter plot for each optical microcavity is then connected by a line to create a line-scatter plot. The range of concentrations that can be measured by each optical microcavity is determined by the range of the linear section of the S-shaped curves in FIG. 33G. The photonic crystal microcavity geometry in arm #1 is chosen to cover the range of concentration from A to B. The photonic crystal microcavity geometry in arm #2 is chosen to cover the range of concentration from B to C. The photonic crystal microcavity geometry in arm #3 is chosen to cover the range of chosen to cover the range of concentration from D to E. Together, the 4 arms cover the range of concentrations from A to E. Since resonance wavelength shifts from all arms are measured simultaneously, in this way, a device that measures biomolecule concentrations over a wide concentration range or a wide dynamic range is achieved by summing over all the photonic crystal microcavities. One skilled in the art will note that the concept can be extended over all photonic crystal microcavities in all 16 output arms measured by the 16 output sub-wavelength grating couplers in FIG. 1A to cover a large range of concentrations to measure.

In one embodiment, the slab 101 is formed from a material of high refractive index including, but not limited to, silicon, germanium, carbon, gallium nitride, gallium arsenide, gallium phosphide, indium nitride, indium phosphide, indium arsenide, zinc oxide, zinc sulfide, silicon oxide, silicon nitride, alloys thereof, metals, and organic polymer composites. Single crystalline, polycrystalline, amorphous, and other forms of silicon may be used as appropriate. Organic materials with embedded inorganic particles, particularly metal particles, may be used to advantage. In one embodiment, the top cladding 106 and bottom cladding 105 are formed from a material whose refractive index is lower than that of the slab material. Suitable top cladding and bottom cladding materials include, but not limited to, air, silicon oxide, silicon nitride, alumina, organic polymers and alloys thereof. The substrate 107 materials include, but not limited to, silicon, gallium arsenide, indium phosphide, gallium nitride, sapphire, glass, polymer and alloys thereof. In one embodiment, the columnar members 102 are formed from a material whose refractive index is substantially different from that of the slab 101. Suitable materials for the columnar members 102 include, but not limited to, air, silicon oxide, silicon nitride, alumina, organic polymers, or alloys thereof. In one preferred embodiment, the slab 101 is formed from silicon, the columnar members 102 are formed from air, the top cladding 106 is the analyte medium, and the bottom cladding 105 is formed from silicon oxide, while the substrate 107 is silicon. In another embodiment, the slab 101 is formed from germanium. The bottom cladding 105 is a low dielectric constant material with transparency in the near-, mid-, and far-infrared such as but not limited to silicon dioxide or silicon nitride, barium fluoride, yttrium fluoride, ytterbium fluoride, cerium fluoride, or dysprosium fluoride. The substrate 107 is but not limited to silicon, gallium arsenide, indium phosphide, sapphire, barium fluoride. The material for the substrate 107, bottom cladding 105, and the slab 101 are chosen so that they are optically transparent in the wavelength of operation, and the dielectric constant of the bottom cladding 107 is lower than the dielectric constant of the slab 101.

Although the word "biomolecule" is used in the preceding discussions, one skilled in the art will understand that it refers to a general form of biomolecule that includes, but not limited to, proteins, deoxyribonucleic acid (DNA), ribonucleic acid (RNA), genes, antigens, antibodies, small molecules, nucleic acids, bacteria, viruses and any arrayed combination thereof for the specific diagnosis of diseases. "Molecule" can denote any polymer or hydrogel that responds to changes in the ambient medium of the device. Any combination of "molecules" and "biomolecules" can be arrayed on the device to get precise knowledge of process conditions, system conditions, analyte identification and/or binding events for disease identification.

Although the word "analyte" is used in the preceding discussions, one skilled in the art will understand that it refers to a general form of analyte that includes solids, liquids, and gases.

Although the word "light" or "lightwave" is used to denote signals in the preceding discussions, one skilled in the art will understand that it refers to a general form of electromagnetic radiation that includes, and is not limited to, visible light, infrared light, ultra-violet light, radios waves, and microwaves.

In summary, the present invention provides a packaging layout for multiplexing several optical waveguides in the photonic crystal platform using sub-wavelength grating couplers for efficient optical coupling in a compact package.

While the invention has been described in connection with a number of preferred embodiments, it is not intended to limit the scope of the invention to the particular form set forth, but on the contrary, it is intended to cover such alternatives, modifications, and equivalents as may be included within the design concept of the invention as defined by the appended claims.

The invention claimed is:

1. A packaged chip for the integration of arrays of photonic crystal microcavity coupled waveguides with external optical sources and external optical detectors comprising:
   i) a package shell comprising a top portion, a bottom portion, and a side wall portion which together surround an interior volume;
   ii) a substrate disposed on the interior side of the bottom portion of the package shell and bounded by the interior side of the side wall portion of the package shell;
   iii) a bottom cladding disposed on the substrate and bounded by the interior side of the side wall portion of the package shell;
   iv) a slab disposed on the bottom cladding and bounded by the interior side of the side wall portion of the package shell, wherein the refractive index of the bottom cladding is lower than the refractive index of the slab;
   v) a cover polymer disposed on the slab, wherein the cover polymer is capped by the interior side of the top portion of the package shell and bounded by the interior side of the side wall portion of the package shell;
   vi) an input sub-wavelength grating coupler comprising a plurality of void columnar members with rectangular cross-section etched through the slab, wherein the plurality of void columnar members have a periodicity $\beta$ in one direction along the slab and a periodicity $\gamma$ in the direction orthogonal to $\beta$ along the slab;
   vii) a first multimode interference power splitter comprising:
      a) a first input end;
      b) a first output end;
      c) a first rectangular mesa defined in the slab;
      d) wherein the first rectangular mesa is coupled by a first ridge waveguide to the input sub-wavelength grating coupler at the first input end of the first multimode interference power splitter; and
      e) wherein the first rectangular mesa is coupled to one or more ridge waveguides at the first output end of the first multimode interference power splitter;
   viii) a cascade of one or more multimode interference power splitters, wherein each of the one or more multimode interference power splitters comprises:
      a) an input end;
      b) an output end;
      c) a rectangular mesa defined in the slab;
      d) wherein the rectangular mesa at the input end of each of the one or more multimode interference power splitters is coupled to one of the one or more ridge waveguides at the first output end of the first multimode interference power splitter or to the output end of one or more multimode interference powers splitters; and e) wherein the rectangular mesa at the output end of each of the one or more multimode interference power splitters is coupled to one or more primary ridge waveguides;
ix) a cascade of one or more photonic crystal microcavity coupled waveguides, wherein each of the one or more photonic crystal microcavity coupled waveguides comprises:
   a) an input side, wherein the input side comprises an input impedance taper, wherein the input impedance taper is configured to minimize Fresnel reflections;
   b) an output side, wherein the output side comprises an output impedance taper, wherein the output impedance taper is configured to minimize Fresnel reflections;
   c) wherein the input side is coupled to one of the one or more primary ridge waveguides of the output end of one of the one or more multimode interference power splitters or to the output side of one of the one or more photonic crystal microcavity coupled waveguides;
   d) wherein the output side is coupled to the input side of one of the one or more photonic crystal microcavity coupled waveguides or to an output ridge waveguide;
   e) a plurality of void columnar members with circular cross-section etched through the slab;
   f) a core in the slab formed by a row of void columnar members, wherein the row of void columnar members is filled with the material of the slab and wherein the plurality of void columnar members surround the core in the slab and form a periodic triangular or square lattice comprising one or more lattice constants, $\alpha$s; and
   g) one or more optical microcavities formed by a group of columnar members, wherein the group of columnar members is filled completely or partially with the material of the slab and wherein the one or more optical microcavities are separated from each other and the core in the slab by one or more lattice constants;
x) a first crossing waveguide crossing the one or more primary ridge waveguides substantially orthogonal to and in the plane of the one or more primary ridge waveguides between the input side of the cascade of one or more photonic crystal microcavity coupled waveguides and the one or more primary ridge waveguides of the output ends of the one or more multimode interference power splitters; and
xi) a second crossing waveguide crossing the output ridge waveguide of each of the one or more photonic crystal microcavity coupled waveguides substantially orthogonal to and in the plane of the output ridge waveguides of each of the one or more photonic crystal microcavity coupled waveguides;
xii) wherein the one or more photonic crystal microcavity coupled waveguides support one or more guided modes of a broadband source;
xiii) wherein each of the one or more optical microcavities support one or more resonance modes;
xiv) wherein the one or more optical microcavities with one or more target binding molecules coated on the one or more optical microcavities support one or more resonance modes comprising one or more resonant frequencies resulting in minima in a transmission spectrum of the one or more guided modes of the broadband source at the corresponding resonant frequencies of the one or more optical microcavities;
xv) wherein one or more analytes selectively bind to the one or more target binding molecules resulting in shifting the resonance frequencies of the one or more optical microcavities and hence the minima in the transmission spectrum of the one or more guided modes of the broadband source in each photonic crystal waveguide;
xvi) wherein the cover polymer disposed on the slab has void openings above the area of the one or more photonic crystal microcavity coupled waveguides to form one or more microfluidic channels;
xvii) wherein the package shell has void openings aligned with the one or more microfluidic channels; and
xviii) wherein the package shell has void openings aligned with the input sub-wavelength grating coupler.

2. The packaged chip of claim 1, further comprising sub-wavelength nanostructures along both sides of the first crossing waveguide within the slab in the region where the first crossing waveguide crosses the one or more primary ridge waveguides.

3. The packaged chip of claim 2, wherein the first crossing waveguide comprises one or more ridge waveguides.

4. The packaged chip of claim 1, further comprising sub-wavelength nanostructures along both sides of the second crossing waveguide within the slab in the region where the second crossing waveguide crosses the one or more photonic crystal microcavity coupled waveguides.

5. The packaged chip of claim 4, wherein the second crossing waveguide comprises one or more ridge waveguides.

6. The packaged chip of claim 1, wherein each of the one or more primary ridge waveguides in the intersection region with the first crossing waveguide comprises:
   i) an expanding taper from the width of the one or more primary ridge waveguides to an expanded width ridge waveguide prior to the crossing with the first crossing waveguide;
   ii) sub-wavelength nanostructures along both sides of the expanded width ridge waveguide within the slab; and
   iii) a reducing taper from the width of the expanded width ridge waveguide to the width of the one or more primary ridge waveguides after the crossing with the first crossing waveguide.

7. The packaged chip of claim 1, wherein each of the one or more photonic crystal microcavity coupled waveguides in the intersection region with the second crossing waveguide comprises:
   i) an expanding taper from the width of the one or more photonic crystal microcavity coupled waveguides to an expanded width ridge waveguide prior to the crossing with the second crossing waveguide;
   ii) sub-wavelength nanostructures along both sides of the expanded width ridge waveguide within the slab; and
   iii) a reducing taper after the crossing with the second crossing waveguide from the width of the expanded width ridge waveguide to the width of the one or more photonic crystal microcavity coupled waveguides.

8. The packaged chip of claim 1, further comprising:
   i) one or more output sub-wavelength grating couplers coupled to the output ridge waveguide of the output side of the one or more photonic crystal microcavity coupled waveguides after the intersection of the second crossing waveguide with the output ridge waveguide of the output side of the one or more photonic crystal microcavity coupled waveguides;
   ii) wherein the substrate has void openings aligned with the one or more output sub-wavelength grating couplers or the cover polymer disposed on the slab has void openings aligned with the one or more output sub-wavelength grating couplers; and iii) wherein the package shell has void openings aligned with the one or more output sub-wavelength grating couplers.

9. The packaged chip of claim 8, wherein the one or more resonance modes are unique along each of the one or more photonic crystal microcavity coupled waveguides.

10. The packaged chip of claim 1, further comprising one or more multimode interference power combiners comprising:
  i) an input end;
  ii) an output end;
  iii) a rectangular mesa defined in the slab;
  iv) wherein the rectangular mesa at the input end of one of the one or more multimode interference power combiners is coupled to the output ridge waveguide of the output side of the one or more photonic crystal microcavity coupled waveguides or the output end of one of the one or more multimode interference power combiners; and
  v) wherein the rectangular mesa at the output end of the one or more multimode interference power combiners is coupled to one or more output sub-wavelength grating couplers; and
  vi) wherein the package shell has void openings aligned with the one or more output sub-wavelength grating couplers.

11. The packaged chip of claim 10, wherein the one or more resonance modes are unique along each of the one or more photonic crystal microcavity coupled waveguides.

12. The packaged chip of claim 10, wherein the substrate has void openings aligned with the one or more output sub-wavelength grating couplers or the cover polymer disposed on the slab has void openings aligned with the one or more output sub-wavelength grating couplers.

13. The packaged chip of claim 1, further comprising the output ridge waveguide of the output side of the one or more photonic crystal microcavity coupled waveguides coupled to one or more two-to-one ridge waveguide junctions; and one of the one or more two-to-one ridge waveguide junctions coupled to an output sub-wavelength grating coupler; and wherein the package shell has a void opening aligned with the output sub-wavelength grating coupler.

14. The packaged chip of claim 13, wherein the one or more resonance modes are unique along each of the one or more photonic crystal microcavity coupled waveguides.

15. The packaged chip of claim 13, wherein the substrate has a void opening aligned with the output sub-wavelength grating coupler or the cover polymer disposed on the slab has a void opening aligned with the output sub-wavelength grating coupler.

16. The packaged chip of claim 1, further comprising the input side of the one or more photonic crystal microcavity coupled waveguides coupled to one or more one-to-two ridge waveguide junctions; and one of the one or more one-to-two ridge waveguide junctions coupled to the input sub-wavelength grating coupler.

17. The packaged chip of claim 1, further comprising a rigid dielectric cover disposed on the cover polymer between the cover polymer and the interior side of the top portion of the package shell.

18. The packaged chip of claim 1, wherein the substrate has a void opening aligned with the input sub-wavelength grating coupler or the cover polymer disposed on the slab has a void opening aligned with the input sub-wavelength grating coupler.

19. The packaged chip of claim 1, further comprising external optical fiber glued to the void openings aligned with the input sub-wavelength grating coupler with ultraviolet cured polymer.

20. The packaged chip of claim 19, wherein the facet of the external optical fiber is polished at an angle to enhance optical coupling efficiency.

21. The packaged chip of claim 20, wherein the facet of the external optical fiber is coated with a reflecting material.

22. The packaged chip of claim 21, wherein the reflecting material comprises gold.

23. The packaged chip of claim 1, wherein one or more analytes selectively bind to the one or more target binding molecules resulting in shifting the resonance frequencies of the one or more optical microcavities and hence the minima in the transmission spectrum of the one or more guided modes of the broadband source.

24. The packaged chip of claim 1, further comprising the same target binding molecule coated on two or more optical microcavities, wherein the two or more optical microcavities comprise different geometry resulting in two or more unique resonance modes comprising two or more resonant frequencies resulting in minima in the transmission spectrum of the one or more guided modes of the broadband source at the corresponding resonant frequencies of the two or more optical microcavities.

25. The packaged chip of claim 24, wherein the two or more optical microcavities are configured to measure different ranges of concentrations of the same analyte.

26. A packaged chip for the integration of arrays of photonic crystal slot waveguides with external optical sources and external optical detectors comprising:
  i) a package shell comprising a top portion, a bottom portion, and a side wall portion which together surround an interior volume;
  ii) a substrate disposed on the interior side of the bottom portion of the package shell and bounded by the interior side of the side wall portion of the package shell;
  iii) a bottom cladding disposed on the substrate and bounded by the interior side of the side wall portion of the package shell;
  iv) a slab disposed on the bottom cladding and bounded by the interior side of the side wall portion of the package shell, wherein the refractive index of the bottom cladding is lower than the refractive index of the slab;
  v) a cover polymer disposed on the slab, wherein the cover polymer is capped by the interior side of the top portion of the package shell and bounded by the interior side of the side wall portion of the package shell;
  vi) an input sub-wavelength grating coupler comprising a plurality of void columnar members with rectangular cross-section etched through the slab, wherein the plurality of void columnar members have a periodicity $\beta$ in one direction along of the slab and a periodicity $\gamma$ in the direction orthogonal to $\beta$ along the slab;
  vii) a first multimode interference power splitter comprising:
    a) a first input end;
    b) a first output end;
    c) a first rectangular mesa defined in the slab;
    d) wherein the first rectangular mesa is coupled by a first ridge waveguide to the input sub-wavelength grating coupler at the first input end of the first multimode interference power splitter; and
    e) wherein the first rectangular mesa is coupled to one or more ridge waveguides at the first output end of the first multimode interference power splitter;

viii) a cascade of one or more multimode interference power splitters, wherein each of the one or more multimode interference power splitters comprises:
   a) an input end;
   b) an output end;
   c) a rectangular mesa defined in the slab;
   d) wherein the rectangular mesa at the input end of each of the one or more multimode interference power splitters is coupled to one of the one or more ridge waveguides at the first output end of the first multimode interference power splitter or to the output end of one or more multimode interference powers splitters; and
   e) wherein the rectangular mesa at the output end of each of the one or more multimode interference power splitters is coupled to one or more primary ridge waveguides;

ix) one or more mode converters along the slab comprising a slotted ridge waveguide at the output of each mode converter and a primary ridge waveguide at the input of each mode converter, wherein the mode converter transforms the optical mode from the primary ridge waveguide mode to a slotted ridge waveguide mode;

x) one or more photonic crystal slot waveguides comprising:
   a) an input side, wherein the input side is coupled to the output of one of the one or more mode converters;
   b) an output side;
   c) a plurality of void columnar members with circular cross-section etched through the slab;
   d) a core in the slab formed by a row of void columnar members, wherein the row of void columnar members is filled with the material of the slab and wherein the plurality of void columnar members surround the core in the slab and form a periodic triangular or square lattice comprising one or more lattice constants, $\alpha$s; and
   e) one or more void slots within the core, extending the entire length of the core;

xi) a first crossing waveguide crossing the one or more primary ridge waveguides substantially orthogonal to and in the plane of the one or more primary ridge waveguides between the primary ridge waveguide at the input of each mode converter and the one or more primary ridge waveguides of the output ends of the one or more multimode interference power splitters;

xii) one or more output mode converters along the slab comprising a slotted ridge waveguide at the input of each of the one or more output mode converters and a primary ridge waveguide at the output of each of the one or more output mode converters, wherein each of the output mode converters transforms the optical mode from the slotted ridge waveguide mode to the primary ridge waveguide mode;

xiii) the output side of the one or more photonic crystal slot waveguides coupled to the slotted ridge waveguide at the input of each of the one or more output mode converters; and xiv) a second crossing waveguide crossing the primary ridge waveguide at the output of each of the one or more output mode converters substantially orthogonal to and in the plane of the primary ridge waveguide at the output of each of the one or more output mode converters after the primary ridge waveguide at the output of each of the one or more output mode converters;

xv) wherein the one or more photonic crystal slot waveguides support one or more guided modes of a broadband source and further comprises a region where the electric field intensity of the coupled electromagnetic radiation of the broadband source is enhanced and the group velocity of the coupled electromagnetic radiation of the broadband source is lowered;

xvi) wherein an output transmission spectrum intensity of the coupled electromagnetic radiation of the broadband source varies as a function of the absorbance of an analyte within the one or more photonic crystal slot waveguides;

xvii) wherein, the cover polymer disposed on the slab has void openings above the area of the one or more photonic crystal slot waveguides; and xviii) wherein, the package shell has void openings aligned with the input sub-wavelength grating coupler.

27. The packaged chip of claim 26, further comprising sub-wavelength nanostructures along both sides of the first crossing waveguide within the slab in the region where the first crossing waveguide crosses the one or more primary ridge waveguides.

28. The packaged chip of claim 27, wherein the first crossing waveguide comprises one or more ridge waveguides.

29. The packaged chip of claim 26, further comprising sub-wavelength nanostructures along both sides of the second crossing waveguide within the slab in the region where the second crossing waveguide crosses the primary ridge waveguide at the output of each of the one or more output mode converters.

30. The packaged chip of claim 29, wherein the second crossing waveguide comprises one or more ridge waveguides.

31. The packaged chip of claim 29, wherein each of the one or more primary ridge waveguides in the intersection region with the first crossing waveguide comprises:
   i) an expanding taper from the width of the one or more primary ridge waveguides to an expanded width ridge waveguide prior to the crossing with the first crossing waveguide;
   ii) sub-wavelength nanostructures along both sides of the expanded width ridge waveguide within the slab; and
   iii) a reducing taper from the width of the expanded width ridge waveguide to the width of the one or more primary ridge waveguides after the crossing with the first crossing waveguide.

32. The packaged chip of claim 29, wherein each of the primary ridge waveguides at the output of each of the one or more output mode converters in the intersection region with the second crossing waveguide comprises:
   i) an expanding taper from the width of the primary ridge waveguides at the output of each of the one or more output mode converters to an expanded width ridge waveguide prior to the crossing with the second crossing waveguide;
   ii) sub-wavelength nanostructures along both sides of the expanded width ridge waveguide within the slab; and
   iii) a reducing taper after the crossing with the second crossing waveguide from the width of the expanded width ridge waveguide to the width of the primary ridge waveguides at the output of each of the one or more output mode converters.

33. The packaged chip of claim 26, further comprising: one or more output sub-wavelength grating couplers coupled to the primary ridge waveguide at the output of each of the one or more output mode converters after the intersection of the second crossing waveguide with the primary ridge waveguide at the output of each of the one or more output mode converters.

34. The packaged chip of claim 27, wherein the substrate has a void opening aligned with the output sub-wavelength grating coupler or the cover polymer disposed on the slab has a void opening aligned with the output sub-wavelength grating coupler.

35. The packaged chip of claim 26, further comprising one or more multimode interference power combiners comprising:
  i) an input end;
  ii) an output end;
  iii) a rectangular mesa defined in the slab;
  iv) wherein the rectangular mesa at the input end of one of the one or more multimode interference power combiners is coupled by a ridge waveguide to the output side of the one or more photonic crystal slot waveguides or the output end of one of the one or more multimode interference power combiners;
  v) wherein the rectangular mesa at the output end of the one or more multimode interference power combiners is coupled to one or more output sub-wavelength grating couplers; and
  vi) wherein the top of the package shell has void openings aligned with the one or more output sub-wavelength grating couplers.

36. The packaged chip of claim 35, wherein the substrate has voided openings aligned with the one or more output sub-wavelength grating couplers or the cover polymer disposed on the slab has void openings aligned with the one or more output sub-wavelength grating couplers.

37. The packaged chip of claim 26, further comprising the slotted ridge waveguide at the output of each mode converter at the output side of the one or more photonic crystal slot waveguides coupled to one or more two-to-one ridge waveguide junctions; and one of the one or more two-to-one ridge waveguide junctions coupled to an output sub-wavelength grating coupler; and wherein the top of the package shell has a void opening aligned with the output sub-wavelength grating coupler.

38. The packaged chip of claim 37, wherein the substrate has a void opening aligned with the output sub-wavelength grating coupler or the cover polymer disposed on the slab has a void opening aligned with the output sub-wavelength grating coupler.

39. The packaged chip of claim 26, further comprising the ridge waveguide at the input of each mode converter at the input side of the one or more photonic crystal slot waveguides coupled to one or more one-to-two ridge waveguide junctions; and one of the one or more one-to-two ridge waveguide junctions coupled to the input sub-wavelength grating coupler; and wherein the top of the package shell has a void opening aligned with the input sub-wavelength grating coupler.

40. The packaged chip of claim 26, further comprising a rigid dielectric cover disposed between the cover polymer and the interior side of the top portion of the package shell.

41. The packaged chip of claim 26, further comprising external optical fiber glued to the void openings with ultraviolet cured polymer.

42. The packaged chip of claim 41, wherein the facet of the external optical fiber is polished at an angle to enhance optical coupling efficiency.

43. The packaged chip of claim 42, wherein the facet of the external optical fiber is coated with a reflecting material.

44. The packaged chip of claim 43, wherein the reflecting material comprises gold.

45. The packaged chip of claim 26, wherein the one or more photonic crystal slot waveguides are covered with hydrophobic polymer.

* * * * *